United States Patent [19]

Lodzinski

[11] 4,019,819
[45] Apr. 26, 1977

[54] OPTICAL PROPERTY MEASUREMENT AND CONTROL SYSTEM

[75] Inventor: Fred P. Lodzinski, Port Edwards, Wis.

[73] Assignee: Nekoosa Papers Inc., Port Edwards, Wis.

[22] Filed: Jan. 10, 1975

[21] Appl. No.: 540,251

Related U.S. Application Data

[63] Continuation-in-part of Ser. No. 429,637, Dec. 28, 1973, abandoned.

[52] U.S. Cl. .............................. 356/73; 162/263; 235/151.3; 250/559; 356/173; 356/176; 356/200
[51] Int. Cl.² .................. G01N 21/00; G01V 1/28; G01N 21/16
[58] Field of Search ............. 356/72, 73, 173, 176, 356/177, 178, 199, 200, 201, 209; 250/559, 571; 235/151.3; 162/263

[56] References Cited

UNITED STATES PATENTS 3,827,808  8/1974  Cho .................................. 356/199

Primary Examiner—Vincent P. McGraw
Attorney, Agent, or Firm—Hill, Gross, Simpson, Van Santen, Steadman, Chiara & Simpson

[57] ABSTRACT

In an illustrated embodiment, brightness, color, opacity and fluorescent contribution to brightness are measured by an on-line sensing head providing for simultaneous measurement of transmitted and reflected light. By measuring two independent optical parameters, paper optical properties of a partially translucent web are accurately characterized substantially independently of paper grade and weight. The instrument is designed so as to be capable of transverse scanning of a moving paper web on the paper machine, and so as to monitor desired paper optical characteristics with sufficient accuracy to enable on-line control of the optical characteristics of the paper being manufactured.

45 Claims, 23 Drawing Figures

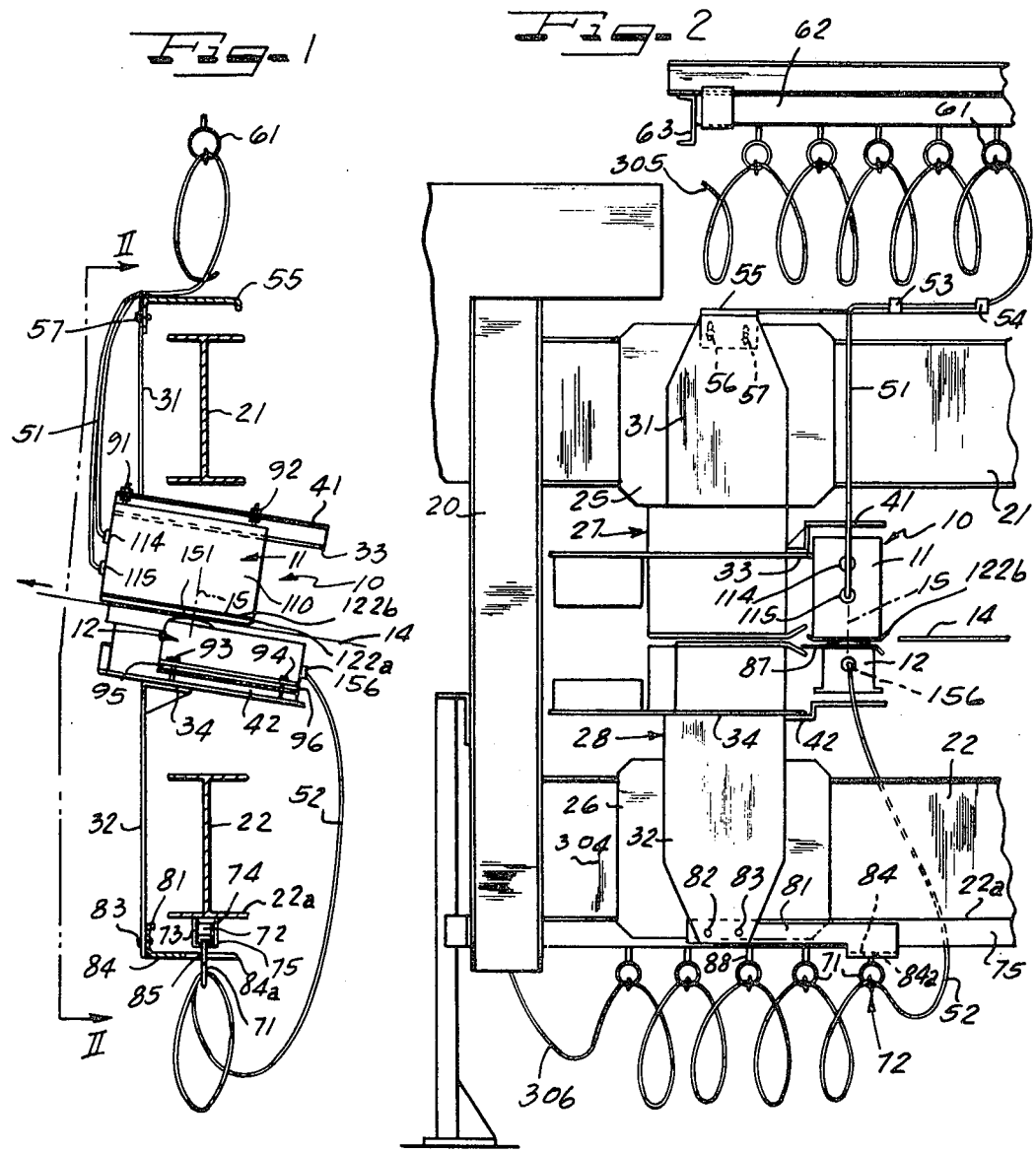

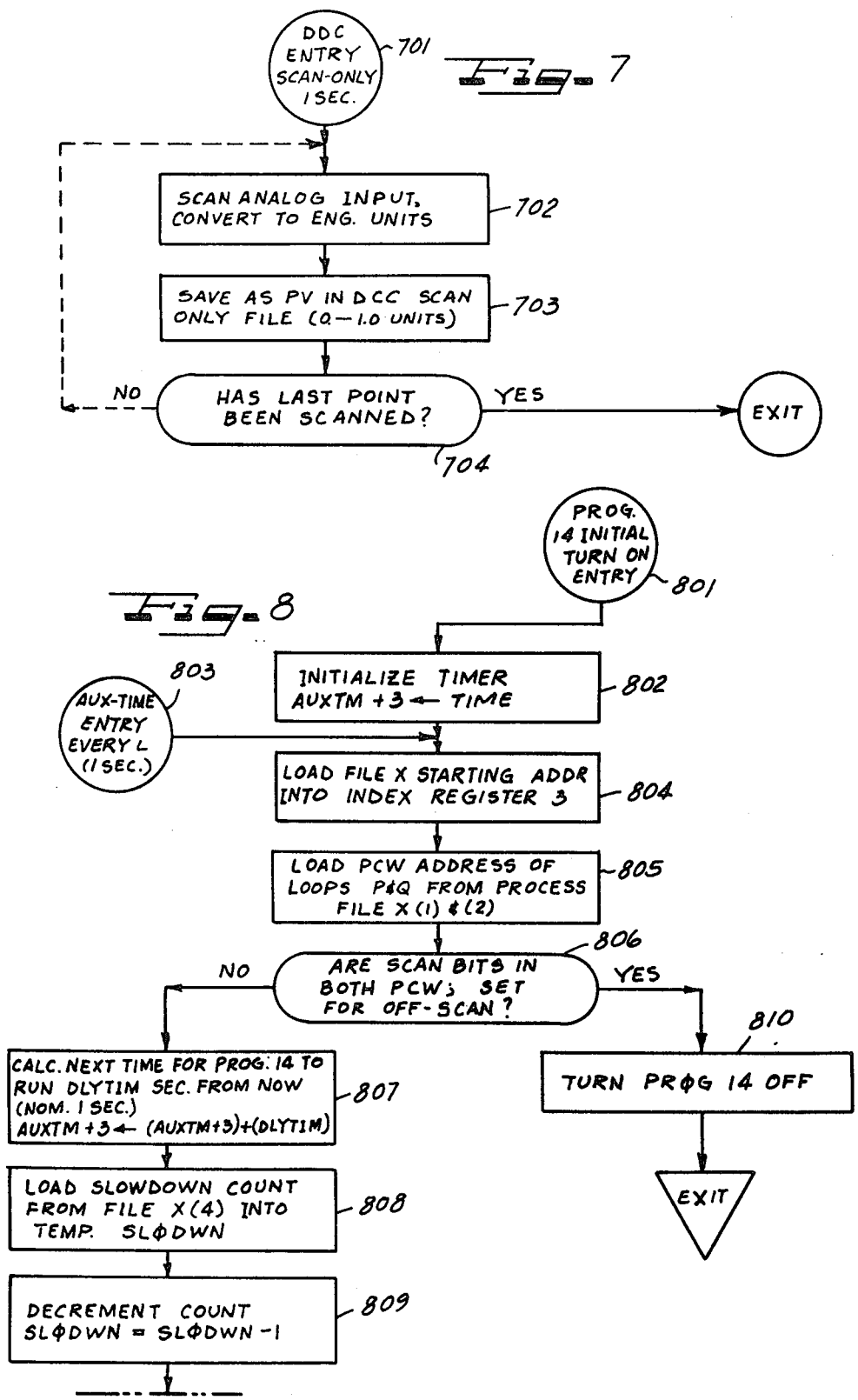

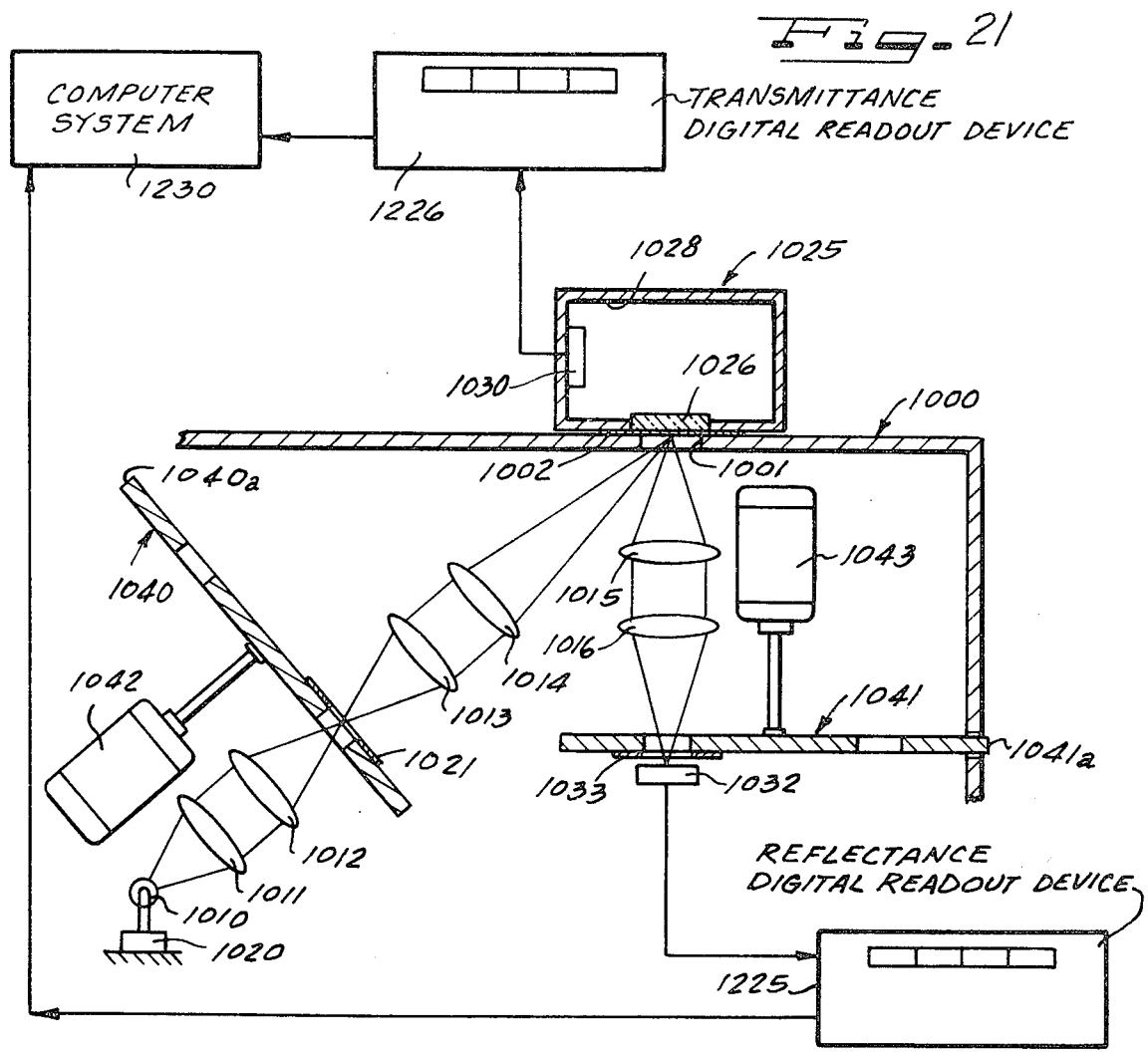
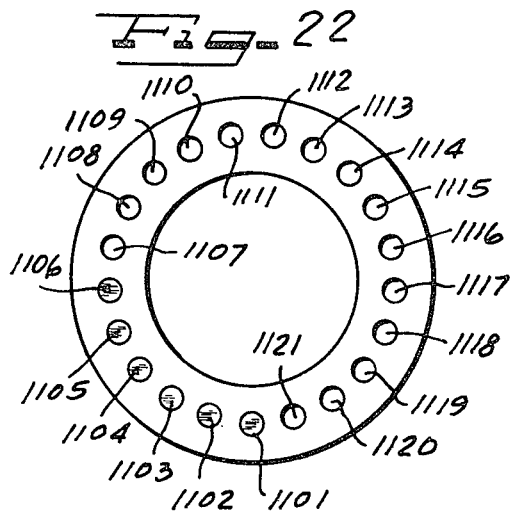
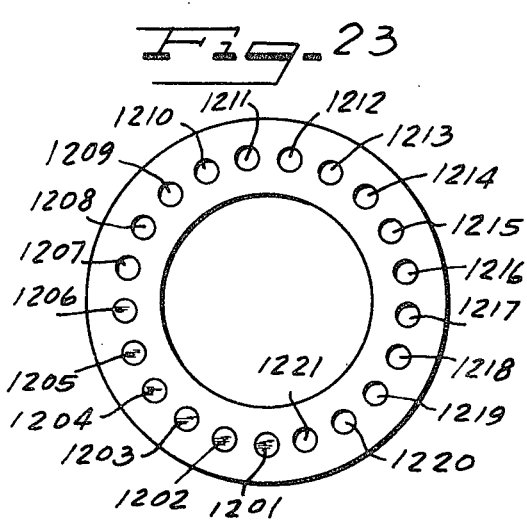

OPTICAL PROPERTY MEASUREMENT AND CONTROL SYSTEM

CROSS-REFERENCES TO RELATED APPLICATIONS

The present application is a continuation-in-part of my copending application Ser. No. 429,637 filed Dec. 28, 1973 (which has now been abandoned in favor of the present case).

Reference is also made to a joint patent application Ser. No. 438,993 filed Feb. 4, 1974, directed to certain improvements which are included in the present disclosure.

BACKGROUND OF THE INVENTION

In the prior art it is known to obtain an indication of color and brightness characteristics of a paper web during manufacture by an on-line measurement of reflectance value (Rg), but this measurement is decidedly different from that necessary for actual color and brightness characterizations. Accordingly, such a measurement must be accompanied by very frequent off-line testng, so as to enable an adequate empirical calibration of the measuring instrument. Further, a separate set of calibration parameters is required for each grade and weight of paper. Off-line instruments which adequately measure these characteristics require that a pad of several thicknesses of paper be exposed to the light source aperture so that a different reflectance value ($R_\infty$) is obtained. Obviously this is impossible with an on-line instrument unless the far more inaccessible reel itself is tested.

Only where the on-line measured reflectance value (Rg) approaches the off-line value ($R_\infty$), as in instances of paper of extremely high opacity such as heavily coated or heavily dyed paper, can the above problems be minimized to the point where accuracy becomes sufficient for control purposes.

SUMMARY OF THE INVENTION

This invention relates to an optical device and method for sensing optical properties of a paper sheet material, and particularly to an on-the-paper-machine device and method for simultaneously sensing both transmitted and reflected light so as to obtain measurements from which the optical properties of interest can be calculated substantially independently of grade and weight of paper involved.

Accordingly it is an object of the present invention to provide an optical monitoring device and method for sensing optical properties based on measurements made on a single thickness of partially translucent paper sheet material and which measurements sufficiently characterize the actual properties of interest that a minimum of empirical calibration is required regardless of changes in grade and weight of paper.

Another object of the invention is to provide such an optical monitoring device and method capable of accurately sensing optical properties such as brightness, color, opacity and/or fluorescent contribution to brightness.

While such an optical monitoring device is useful off-line for sensing optical properties of a single thickness sample, it is a further important object of the present invention to provide such an optical monitoring device which is of sufficiently light weight and compact construction so as to be adapted for on-line monitoring of the desired optical properties.

Another and further object of the invention is to provide an on-the-paper-machine optical monitoring device of sufficient flexibility and accuracy to enable control of desired optical properties during the paper making process.

A unique feature of the on-line optical monitoring device is its ability to simultaneously measure both reflected and transmitted light. By measuring two independent optical parameters it is possible to thoroughly characterize the paper optical properties of a partially translucent web with a minimum of empirical correction for factors such as paper grade and weight.

Other objects, features and advantages of the present invention will become apparent from the following detailed description taken in connection with the accompanying drawings.

ON THE DRAWINGS

FIG. 1 is a fragmentary somewhat diagrammatic longitudinal sectional view of a paper machine showing in outline a side view of an optical monitoring device in accordance with the present invention operatively mounted on line with the machine;

FIG. 2 is a fragmentary somewhat diagrammatic transverse sectional view of the paper machine of FIG. 1 and taken generally as indicated by the line II—II of FIG. 1 and looking in the direction of the arrows (toward the wet end of the paper machine), the view being taken so as to show in outline a direct front view of the optical monitoring device of FIG. 1;

FIG. 7 is a flow chart illustrating an existing direct digital control analog point scan program which as been adapted to allow for the collection and temporary storage of the reflectance and transmittance data acquired from the system of FIGS. 1–6;

Figure 3:
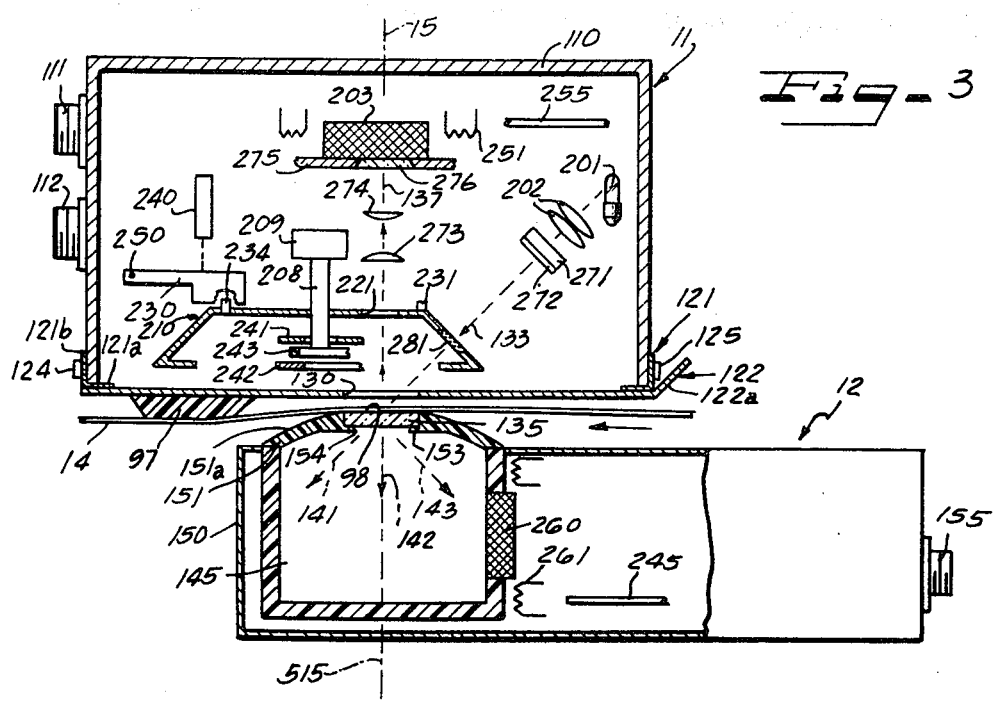
FIG. 3 is a diagrammatic longitudinal sectional view of an on-the-paper-machine optical monitoring device in accordance with the present invention.

FIGS. 8–16 when arranged in a vertical series represent a program fourteen which is designed to read the reflectance and transmittance values stored pursuant to FIG. 7 and generally to control the operation of the system of FIGS. 1–6 and to apply correction factors to the raw reflectance and transmittance data;

FIGS. 17–20 when arranged in a vertical sequence represent data reduction program forty-two whose purpose is to reduce the corrected reflectance and transmittance data as produced by the program of FIGS. 8–16 into terms with which papermakers are familiar and upon which paper optical specifications are based, e.g. brightness, opacity, color and fluorescence;

FIG. 21 is a diagrammatic vertical sectional view showing an off-the-machine instrument for simulating the optical measurements of the embodiment of FIGS. 1–20; and FIGS. 22 and 23 are diagrammatic plan views showing the incident beam filter wheel and the reflected beam filter wheel, respectively, for the instrument of FIG. 21.

DESCRIPTION OF THE PREFERRED EMBODIMENTS

Detailed Description Of The Apparatus Of FIGS. 1 and 2

FIGS. 1 and 2 will serve to illustrate the modifications of an existing paper machine which are required for carrying out a preferred embodiment of the present invention. Referring to FIGS. 1 and 2, an on-the-paper-machine optical monitoring device is diagrammatically indicated at 10 and comprises an upper sensing head 11 and a lower sensing head 12 which are maintained in precise relative alignment and disposed for operative association and transverse scanning movement relative to a paper web located as indicated at 14 in FIGS. 1 and 2. As will be described hereinafter with reference to FIGS. 3 and 4, in a particular design of the optical monitoring device, upper head 11 includes a light source for projecting light onto the web such that a portion of light is reflected parallel to an optical axis indicated at 15, while a further portion of the light is transmitted through the paper web for collection and measurement by means of the lower sensing head 12.

For purposes of illustration, FIGS. 1 and 2 show portions of an existing web scanner construction which is utilized to scan the web 14 for conventional purposes. The conventional scanner construction includes fixed frame components such as 20, 21 and 22 forming what is known as an O type scanner frame. The conventional scanning structure further includes upper and lower slides 25 and 26 for joint horizontal movement along the horizontal beams 21 and 22. Associated with the slides 25 and 26 are movable assemblies 27 and 28 carried by the respective slides 25 and 26 and including vertically disposed plates 31 and 32 and angularly disposed flange members such as indicated at 33 and 34 in FIG. 1. These flange portions 33 and 34 have broad surfaces lying in planes generally parallel to the plane of the web 14 and are utilized for mounting of the monitoring device 10 of the present invention. In particular a top head mounting bracket is indicated at 41 in FIGS. 1 and 2 and is shown as being secured to the existing flange part 33 so as to mount the upper head 11 for scanning movement with the assembly 27. Similarly a lower head mounting bracket is indicated at 42 and is shown as being secured to flange part 34 of the lower movable assembly 28 so as to mount the lower sensing head 12 for scanning movement jointly with the upper sensing head 11.

For the purpose of electrical connection with the monitoring device 10 during its traverse of the web 14, electric cables are indicated at 51 and 52 for electrical connection with the components of the upper sensing head 11 and lower sensing head 12 of the monitoring device 10. The cable 51 is shown as being fastened by means of straps 53 and 54 to a top carrier slide bracket 55. The bracket is shown as being secured by means of fasteners 56 and 57 to the upper portion of vertical plate 31. As indicated in FIG. 2, successive loops of cable 51 are secured to swivel type ball bearing carriers such as indicated at 61. A trolley track 62 is supported from existing channels such as indicated at 63 and mounts the carriers 61 for horizontal movement as required to accommodate the scanning movement of the monitoring device 10 across the width of the web 14. Similarly, successive loops of the cable 52 are fastened to the eyes such as indicated at 71 of a lower series of carriers 72. As seen in FIG. 1 each of the carriers such as 72 includes a pair of rollers such as 73 and 74 riding in the trolley track 75 which is secured directly to the lower flange 22a of beam 22. A lower carrier slide bracket 81 is secured to vertical plate 32 by means of fasteners 82 and 83 and is provided with a horizontally extending flange 84 for engaging with the first of the series of lower carriers 72. In particular, carrier 72 is provided with a shank 85 which extends into a longitudinal slot 84a of flange 84. Thus, the first carrier 72 is interengaged with the bracket 81 and is caused to move with the lower assembly 28 and the lower sensing head 12. The remaining lower carriers such as that indicated at 83 move along the trolley track 74 as necessary to accommodate movement of the monitoring device 10 transversely of the web 14.

While FIGS. 1 and 2 have illustrated the optical monitoring device of the present invention as being mounted on line with the paper machine and have further illustrated the case where the monitoring device is to be scanned tranversely of the web, it is considered that the optical monitoring device of the present invention would also be of great value if redesigned for bench mounting. By placing a single sheet of paper in a sample mount of the device, a technician could simultaneously test the sample for color, brightness, fluorescence, and opacity in a matter of seconds.

In the illustrated embodiment, however, it is contemplated that the monitoring device 10 will be mounted on line with the paper machine and will be capable of movement to a position clear of the edge of the web as indicated in FIG. 2 at the end of each hour of operation, for example. When the end of a production run for a given web 14 has been reached, or when a web break occurs for any other reason (such as accidental severance of the given web), the monitoring device 10 will be moved clear of the edge of the web path as indicated in FIG. 2. Each time the monitoring device 10 is moved to the off-web position shown in FIG. 2 it is preferred that readings be taken of the reflectance and transmittance values (without the web in the optical path) for the purpose of obtaining an updated calibration of the monitoring device. Thus, such updating of calibration may take place automatically (for example under the control of a process control computer controlling the paper manufacturing operation) at hourly intervals and also after web breaks. The monitoring device can, of course, be retracted manually any time desired by the operator for the purpose of checking calibration. By way of example, the monitoring device 10 may be capable of a normal scanning travel over a distance of 115 inches with provision for an additional travel of 16 inches to the position shown in FIG. 2. A flange is indicated at 87 which serves to insure proper re-engagement of the sensing head with the web at the operator's side of the illustrated paper machine (opposite the side indicated in FIG. 2).

The lower head 12 is designed to contact the web 14 during scanning thereof. The design spacing between the upper and lower heads 11 and 12 is 3/16 inch. The optical opening in the upper head 11 is aligned with the optical axis 15 and is to be maintained in alignment with the center of the window in the lower head 12. Four adjusting screws such as those indicated at 91 and 92 are provided for accurate positioning of the upper head 11. Similarly four position adjusting screws such as 93 and 94 serve for the accurate positioning of the lower head in conjunction with set screws such as indicated at 95 and 96. The adjusting screws are located at each corner of mounting brackets 41 and 42.

MODIFICATIONS OF FIGS. 1 AND 2 TO INSURE ACCURATE SCANNING

Where the web is not perfectly horizontal, but instead is curved across, its width, it is desirable to provide a web deflecting guide bar as indicated at 97 in FIG. 3 for insuring stable contact between the web 14 and the web engaging surface 98 of the lower sensing head 12. By way of example the guide bar may protrude from the lower surface of the upper sensing head a distance of 5/16 inch so as to overlap with respect to the vertical direction a distance of ⅛ inch relative to the lower sensing head web contacting surface 98. The guide bar 97 may have a width to force down at least about four inches of the width of the web at a section of web centered with respect to web engaging surface 98 of the lower sensing head relative to the machine direction. This insures a minimum of a ⅛ inch bellying of the sheet as it travels over the lower sensing head in all lateral positions of the sensing head.

In order to minimize changes in the 5/16 inch thickness dimension of the guide bar 97 due to wear, the guide bar is provided with a flat web engaging surface 97a which has a dimension in the direction of web movement of about one inch. By way of example, the guide bar may be made of Teflon.

Since the guide bar 97 is not necessary when the web is fed from the calender stack to the reel in a relatively planar configuration, it has not been shown in FIGS. 1 and 2.

Various modifications may of course be made to adapt the monitoring device of the present invention to various types of paper machinery, and to secure any desired degree of accuracy in the joint scanning movement of the upper and lower sensing heads relative to the paper.

STRUCTURE OF THE OPTICAL MONITORING DEVICE AS SHOWN IN FIGS. 3 AND 4

Referrring to FIG. 3, the upper sensing head 11 is shown as comprising a casing 110 having suitable connectors 111 and 112 for receiving suitable internally threaded fittings 114 and 115, FIG. 1, associated with the electric cable 51. The casing 110 receives a top head shoe 120 including an interior open rectangular frame 121 having a base flange 121a spot welded to shoe plate 122. The upstanding portion 121b engages the adjacent wall of casing 110 along all four sides thereof and is secured to the casing 110 by suitable fastening means such as indicated at 124 and 125 in FIG. 3. An edge 122a of shoe plate 122 is bent up at an angle of 45° at the side of the sensing head 11 facing the wet end of the paper machine, and a similar inclined edge 122b, FIG. 1, is provided at each of the sides of the sensing head so as to present smooth faces to the paper web during scanning movement of the sensing head. The shoe plate 122 is provided with a circular aperture of less than one inch diameter as indicated at 130 centered on the optical axis 15 of the device. In a present embodiment aperture 130 has a diameter of about ⅞ inch. This aperture 130 is preferably of minimum diameter necessary to accommodate the light paths of the instrument. In the illustrated embodiment the light path for the incident light beam as indicated at 133 is directed at an angle of approximately 45° and is focused to impinge on a window 135 at the optical axis 15. A reflected light path as indicated at 137 is normal to the web engaging surface 98 (which is the upper surface of window 135), and is coincident with the optical axis 15, which light transmitted through the web 14 and through the window 135 is directed as indicated by rays 141–143, for example, into an integrating cavity 145 of lower head 12.

The lower head 12 comprises a casing 150 having an annular dished plate 151 secured thereto and providing a geneally segmental spherical web-contacting surface 151a surrounding window 135. The window 135 is preferably formed by a circular disk of translucent diffusing material. In the illustrated embodiment the window 135 is made of a polycrystalline ceramic material available under the trademark "Lucalux" from the General Electric Company. This material has physical properties similar to that of sapphire. The opposite faces of window 135 are flat and parallel and the thickness dimension is 1/16 inch. A lip is indicated at 153 for underlying an annular edge portion of window 135. This lip provides a circular aperture 154 having a diameter of about 15/16 inch so that the effective viewing area for the transmitted light is determined by the diameter of aperture 154. The casing 150 is shown as being provided with an electrical connector terminal 155 for receiving a suitable internally threaded fitting 156, FIG. 1, of cable 52.

Figure 4:
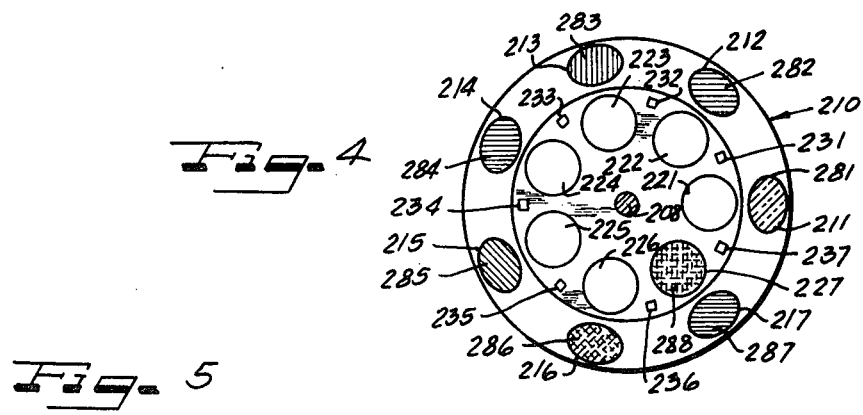
FIG. 4 is a partial diagrammatic plan view of the filter wheel assembly utilized in the monitoring device of FIG. 3.

As diagrammatically indicated in FIGS. 3 and 4, the upper sensing head 11 includes a light source 210, incident optical path means including lenses such as indicated at 202 and a photocell 203 for measuring reflected light returning along the reflected light path 137. A filter wheel 210 is shown diagrammatically as being mounted on a shaft 208 for rotation by means of a low torque motor indicated at 209. As best seen in FIG. 4, the filter wheel includes an outer series of apertures 211–217 for selective registry with the incident light beam path 133, and includes a series of inner apertures 221–227 for selective registry with the reflective light beam path 137. The various apertures may receive suitable filter elements as will hereinafter be explained in detail such that a series of measurements may be taken by successively indexing the filter wheel 210 to successive operating positions. In each operating position one aperture such as 211 is in alignment with the incident beam path 133 and a second aperture such as indicated at 221 is in alignment with the reflected light beam path 137.

By way of example, the motor 209 may be continuously energized during operation of the monitoring device, and the filter wheel may be retained in a selected angular position by engagement of a ratchet arm 230 with one of a series of cooperating lugs 231–237 arranged generally as indicated in FIG. 4 on the filter wheel 210. A solenoid is indicated at 240 as being mechanically coupled with ratchet arm 230 for momentarily lifting the ratchet arm 230 out of engagement with a cooperating lug such as 231 so as to permit the filter wheel to index one position. Immediately upon release of the energization of solenoid 240, the force of gravity returns the ratchet arm 230 to the position shown in FIG. 3 so as to be disposed in the path of the lugs and thus to engage the next lug in succession such as lug 232 as the motor 209 moves the filter wheel 210 into the next operating position.

As will hereafter be explained in greater detail, reed switches are mounted in circles on respective switching boards 241 and 242, FIG. 3, and the filter wheel shaft 208 carries a magnet 243 for actuating a respective pair of the reed switches in each operating position of the filter wheel 210. Thus the position of the filter wheel 210 determines which of the switches on the switching boards 241 and 242 are closed. As will be explained hereinafter, the reed switch on the upper switching board 241 which is closed determines the gain setting of an upper head amplifier at a level appropriate for the set of filters which are in the operating position. The reed switch on the lower switching board 242 which is closed activates a relay on a circuit board 245 in the lower head 12, and such relay in turn sets the lower head amplifier gain at the proper level. As will be explained in connection with the electric circuit diagram for the monitoring device, certain conductors of the cable 51 may be interconnected at a remote location so as to cause an indexing movement of the filter wheel 210. This external command serves to momentarily energize solenoid 240 and lift the ratchet arm 230 about is pivot point 250, allowing the motor 209 to rotate the filter wheel 210. The rachet arm 230 returns to the position shown in FIG. 3 to catch the next lug on the filter wheel stalling the motor 209.

Four heaters such as indicated at 251 are mounted around photocell 204 so as to minimize the temperature variations of the photocell. A circuit board for mounting an amplifier for photocell 203 and for mounting the gain setting resistances associated with the reed switches is indicated at 255 in FIG. 3.

Referring to the lower head 12, FIG. 3 indicates a photocell 260 for receiving light from the integrating cavity 145 and a series of heaters such as 261 mounted around the photocell 260 to minimize the temperature variations of the photocell. Circuit board 245 may mount a suitable amplifier for photocell 260, the gain of which being controlled by the relays previously mentioned.

The heaters 251 and 261 in the prototype unit were Pennsylvania Electronics Technology Type 12T55. (These are positive temperature coefficient thermistors with 55° C. switching temperatures.) These heaters will tend to stabilize the temperature since their ability to provide heat decreases as the ambient temperature increases. Above 55° C., they provide essentially no heat at all.

DISCUSSION OF ILLUSTRATIVE OPERATING DETAILS FOR THE MONITORING DEVICE OF FIGS. 3 AND 4

A basic feature of the illustrated embodiment resides in its ability to measure simultaneously both reflected and transmitted light. While in the illustrated embodiment, the reflected light path 137 and the transmitted light path intersect the web 14 essentially at a common point, reflected light could be obtained from a point on the sample or web offset from the point where light is transmitted through the sample. For example, a backing of some specified reflectance such as a black body of zero or near zero reflectance could be located on the lower sensing head just ahead of or behind the transmitted light receptor compartment (with respect to the machine direction of the sample or the direction of movement of the web). In this case the upper sensing head could contain the light source as well as a reflected light receptor for receiving light reflected from the sample or moving web at a point directly above the backing of specified reflectance. Both the reflected light receptor in the upper sensing head and the transmitted light receptor in the lower sensing head could then supply signals simultaneously and continuosly during measurement operations. Many other variations in the arrangement of the optics for measuring both reflected and transmitted light will occur to those skilled in the art.

Referring to the details of the illustrated embodiment, however, and to the case where it is desired to measure brightness, color, opacity and fluorescent contribution to brightness, light source 201, FIG. 3, may consist of a Model 1962 Quartzline lamp operated at 5.8 volts as measured at the lamp terminals. The 45° incident beam path 133 and the normal reflected beam path 137 correspond to those of a standard brightness testor, and a casting (now shown) from a bench type standard brightness tester was used in constructing a prototype of the illustrated embodiment to give rigid support for the optical components such as indicated at 202 and 271–276 in FIG. 3. In the specific prototype unit, a stock thickness polished Corning tye 4–69 glass filter 271 and a second type 4–69 filter 272 ground and polished to an appropriate thickness were used in the incident beam path to absorb most of the infrared as well as to give proper spectral response.

The reflected light path 137 included a pair of lenses 273 and 274 which focus the light on a ⅜-inch aperture in the plate 275 of the casting. A piece of diffusing glass 276 is located on the ⅜-inch aperture so that the light distribution over the surface of photocell 203 will be reasonably uniform. A Weston model 856 RR Photronic cell was employed.

The filter wheel 210 is designed and located in such a way that either the incident or the reflected beam or both can be filtered as desired. In the prototype, the wheel 201 was driven by a small motor 209 operated at reduced voltage so that it could operate continuously in a stalled condition.

Commercially available color and brightness meters are usually manufactured with the spectral response filters located in the reflected beam. In the prototype device, and in the later on-machine version here illustrated as well, however, the filters which determine the spectral response of the first six filter positions are located in the incident beam. There are two basic reasons for this choice of design.

1. Both the reflected and transmitted light have the same incident intensity and spectral response against which each can be compared. The alternate would necessitate two sets of identical filters, one set located in the reflected beam and another in the transmitted beam—a difficult design to achieve in practice.
2. filters in the incident beam can be used to absorb all ultraviolet light and prevent it from striking the specimen.

Thus, fluorescence, a phenomenon not accounted for by Kubelka-Munk theory is avoided.

For reasons explained shortly, the seventh filter position is an exception to the above in that substantial ultraviolet light is intentionally permitted to exist within the incident beam. Outside of the phenomenon of fluorescence the spectral response is independent of whether such filters are located in the incident or the reflected beams.

The spectral response provided by the respective positions of the filter wheel 210 were as follows: (1) papermaker's brightness (TAPPI brightness), (2) blue portion of the $E_c\bar{x}$ function, (3) red portion of the $E_c\bar{x}$ function, (4) $E_c\bar{z}$ function without fluorescence (5) $E_c\bar{y}$ function, (6) $E_a\bar{y}$ function, and (7) $E_c\bar{z}$ function, with fluorescence.

As is understood in the art, the symbols $E_c\bar{x}$, $E_c\bar{y}$, $E_a\bar{y}$, and $E_c\bar{z}$ refer to tristimulus functions of wavelength as defined by the Commission Internationale c l'Eclairage which is identified by the abbreviation C.I.E. and is also known as the International Committee on Illumination. The subscript a in the function designation $E_a\bar{y}$ indicates that the function is based on a standardized illumination designated as C.I.E. Illuminant A, while the subscript c in the other function designations refers to a somewhat different standardized illumination which is designated as C.I.E. Illuminant C.

Filters for providing the above spectral response characteristics in the respective operating positions of the filter wheel 210 have been indicated in FIG. 4 by reference numeral 281-288. In the specific example under discussion, apertures 221-226 are left open,. Filter 281 is a standard filter for use in measuring TAPPI brightness, TAPPI referring to the Technical Association of the Pulp and Paper Industry. This filter transmits a narrow band of wavelengths in the vicinity of 457 nanometers.

Filters 282-285 are standard filters for a four-filter colorimeter and are conventionally designated X (blue), X (red), Z, and $Y_C$. These filters provide the wavelengths distributions required for the measurement of the C.I.E. X, Y, and Z tristimulus values under Illuminant C.

Filter 286 is conventionally designated as a $Y_A$ filter and is required by the TAPPI standard method for opacity measurements. This is a broad band filter producting the C.I.E. Y wavelength distribution for Illumimnant A, in conjunction with the source 201 previously described in this section. A discussion bearing on the feasibility of this type of measurement is found in a paper by L. R. Dearth, et al entitled "Study of Instruments for the Measurement of Opacity of Paper, V. Comparison of Printing Opacity Determined with Several Selected Instruments," Tappi, volume 53, No, 3 (March, 1970).

With respect to position No. 7 of the filter wheel 210, filters 287 and 288 are conventionally designated as Z (blue) and Z (yellow). As previously indicated, the purpose of the filters is to provide for a determination of the C.I.E. Z tristimulus value with the fluorescence component included. In a filter position No. 4, filter 284 serves to remove the ultraviolet component from the incident beam so that a measure of the Z tristimulus value without fluorescence is obtained. In position No. 7 of the filter wheel, however, filter 287 in the incident beam is designed to transmit the ultraviolet component, so that the fluorescent component if any will be transmitted to photocell 203. The ultraviolet absorbing component of the Z type filter means is located in the reflected beam 137, whereas this component is in the incident beam for the No. 4 position. The fluorescent component is lineally related to the difference between the Z tristimulus values determined in the No. 4 and No. 7 positions of the filter wheel 210.

Filters 281-288 have been shown in FIG. 4 with different types of hatching which have been selected to represent generally the different light transmission properties of the filters. In particular, the hatching for filters 281-288 are those for representing white, blue, red, blue, green, orange, blue and yellow light transmission properties. The selection of hatching is primarily for purposes of graphical illustration and is not, of course, an exact representation of the light transmission properties of the respective filters.

DETAILED DESCRIPTION OF FIGS. 5 AND 6

Figure 5:
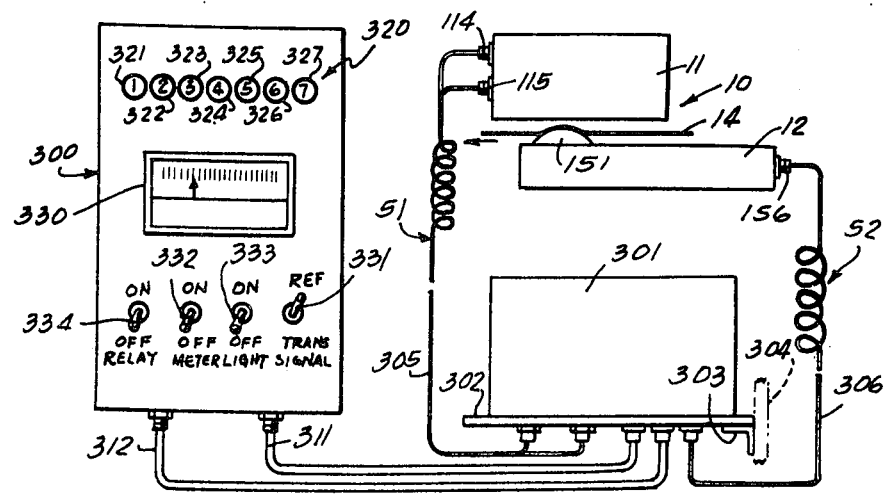
FIG. 5 is a somewhat diagrammatic view illustrating an optical analyzer unit in electrical association with the optical monitoring device of FIGS. 1–4 and with a power supply unit.

FIG. 5 illustrates diagrammatically the optical monitoring device 10 of FIGS. 1-4, and illustrates by way of example an optical analyzer unit 300 which may be electrically associated with the monitoring device and serve as an operator's console to be disposed at a convenient location adjacent the paper machine. By way of example, the optical analyzer unit may be mounted near the dry end of the paper machine, and may receive conventional alternating current power from the paper machine dry end panel. The optical analyzer unit 300 is illustrated as being coupled with the monitoring device 10 via a power supply unit 301 which is mounted adjacent the vertical column 20, FIG. 2, of the O frame along which the monitoring device is to travel in scanning the width of the web. For purposes of diagrammatic illustration, power supply unit 301 is shown as being provided with a mounting plate 302 which is secured by means of a bracket 303 to an end of horizontal beam 22 which has been specifically designated by reference numeral 304 in FIGS. 2 and 5. Referring to FIG. 2, it will be observed that the ends 305 and 306 of cables 51 and 52 are adjacent the end 304 of beam 22 so that this is a convenient location for mounting of the power supply 301. The electrical interconnections between the power supply unit 301 and the optical analyzer unit 300 are indicated as extending via a signal conduit 311 and a control conduit 312. By way of example, the signal conduit 311 may contain shielded electric cables for transmitting millivolt signals from the analogue amplifiers of the upper and lower sensing heads 11 and 12. The control conduit 312 may contain conductors which are respectively energized to represent the angular position of filter wheel 210, and may also contain a conductor for controlling the indexing movement of the filter wheel as will be explained in detail in connection with FIG. 6.

Referring to the optical analyzer unit 300 of FIGS. 5, the front panel of the unit has been diagrammatically indicated at 320 as being provided with a series of lamps 321-327 for indicating the angular position of the filter wheel 210 within the upper sensing head 11. The lamps 321-327 have been numbered 1 through 7 in correspondence with the seven positions of the filter wheel, and the color of the lamps, for example, may be selected so as to signify the characteristics of the filters located in the openings of the filter wheel such as those indicated at 211-217.

In order to provide a visual indication of the amplitude of the millivolt signals supplied from the sensing heads 11 and 12, a suitable meter is indicated at 330 and a selector switch is indicated at 331 for selectively supplying to the meter the analogue signal from the upper sensing head 11 or from the lower sensing head 12. A switch 332 is indicated for controlling the supply of conventional alternating current power to the meter, and a second switch 333 is indicated for controlling the supply of energizing power for the lamps 321–327. Another switch 334 may be momentarily actuated so as to index the filter wheel 210 to a desired station. The switches 331–334 may, of course, take any desired form, and have merely been indicated diagrammatically in FIG. 5.

Figure 6:
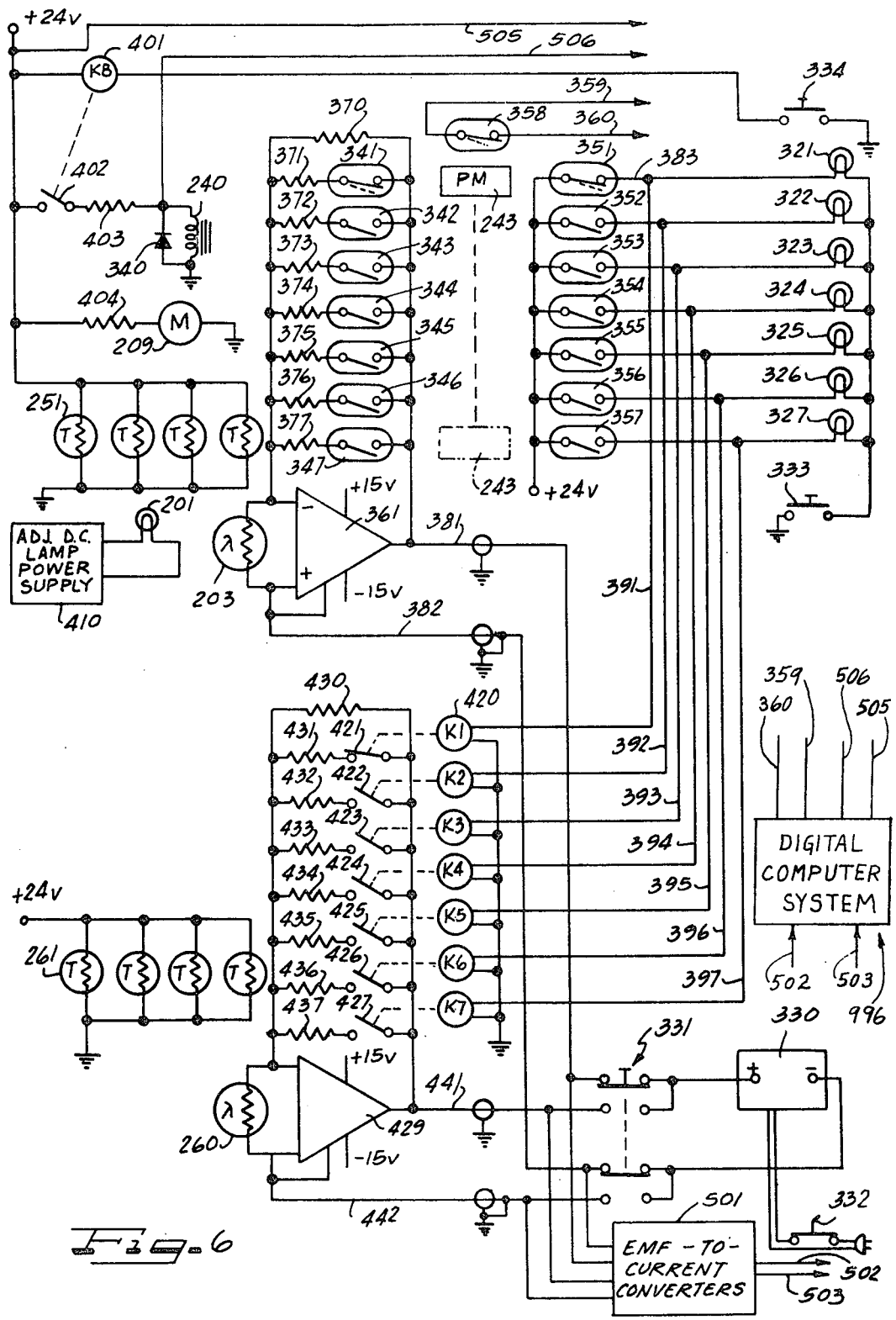
FIG. 6 is an electric circuit diagram illustrating the electrical connections between the various components of FIGS. 1–5.

Referring to FIG. 6, various of the components previously referred to have been indicated by electrical symbols, and for convenience of correlation of FIG. 6 with FIGS. 1 through 5, the same reference characters have been utilized. In particular, FIG. 6 shows symbolically a light source 201, associated photocells, 203 and 260, filter wheel drive motor 209, control solenoid 240, and permanent magnet 243 which rotates with the filter wheel 210 so as to represent the angular position of the filter wheel. Also shown in FIG. 6, are the four heaters 251 associated with photocell 203, and the four heaters 261 associated with the photocell 260. Further lamps 321–327, millivoltmeter 330 and switches 331–334 of the optical analyzer unit 300 have been symbolically indicated in FIG. 6.

Referring first to the components associated with the upper sensing head 11, there is illustrated in the upper left part of FIG. 6 a diode 340 connected across solenoid 240. For diagrammatic purposes, permanent magnet 243 is shown arranged between two series of reed switches 341–347 and 351–357. A further reed switch 358 is indicated for actuation in the number 1 position of the filter wheel 210 along with switches 341 and 351. The conductors 359 and 360 associated with switch 358 may be connected with the optical analyzer unit 300, and may be connected via the optical analyzer unit 300 with a remote computer, where the illustrated apparatus forms part of a computer control system for controlling the associated paper machinery.

The reed switches 341–347 are shown as being associated with an operational amplifier 361, so that switches 341–347 serve to select the desired value of feed back resistance for the amplifier in each position of the filter wheel 210. Thus, switches 341–47 served to selectively connect in parallel with resistance 370, additional resistance values 371–377, respectively, for adjusting the total resistance between the input and output terminals of the amplifier 361. Thus, in the number 1 position of the filter wheel, permanent magnet 243 is in a position to actuate switch 341, and connect resistance value 371 in parallel with resitor 370. As will hereinafter be explained, resistance meand 371–377 may include variable resistors for adjustment so as to provide the desired gain of amplifier 361 in the respective filter positions, or fixed resistance values may be inserted as indicated, once the desired values have been determined for given filter wheel. As indicated in FIG. 6, the output of amplifier 361 may be transmitted by means of shielded cables 381 and 382. These cables form part of the overall cable indicated at 51 in FIG. 5 leading from the upper sensing head 11 to the power supply unit 301.

Also forming part of the cable 51 would be the conductors such as indicated at 383 from the respective reed switches 351–357. These conductors such as 383 would connect with respective conductors 391–397 of cable 52 leading from the power supply 301 to the lower sensing head 12.

Included as part of the power supply unit 301 would be components such as relay actuating coil 401, associated normally open contact 402, and resistors 403 and 404 shown at the upper left in FIG. 6. Further, the power supply would include an adjustable direct current lamp power supply component 410 for supplying a precisely adjusted or controlled electrical energization for light source 201. Further, of course, the power supply would supply the required direct current operating potentials for the upper sensing head as indicated in FIG. 6.

The lower left section of FIG. 6 illustrates the electrical components of the lower sensing head 12. In the lower sensing head, conductors 391–397 control energization of the operating coils of respective relays K1 through K7. With the permanent magnet 243 in the number 1 position, reed switch 351 is closed, and operating coil 420 of relay K1 is energized closing the associated relay contact 421. The remaining relays K2 through K7 are deenergized, so that the respective associated contacts 422–427 remain open. The contacts 421–427 serve to control the resistance in the feed back path of operational amplifier 429 in conjunction with resistor 430 and resistance means 431–437. As explained in reference to the upper sensing head, resistance means 431–437 may include adjustable resistors, or fixed resistors as shown selected to provide the desired gain of amplifier 429 for the respective positions of the filter wheel 210. The shielded cables 441 and 442 from the output of amplifier 429 connect with power supply unit 301 as part of cable 52. The outputs from the amplifiers 361 and 429 are conducted from the power supply unit 301 to the optical analyzer unit 300 via signal conduit 311, and within the optical analyzer unit connect with respective terminals of the selector switch 331 as indicated as the lower part of FIG. 6. Thus, in the upper position of the selector 331, the output of amplifier 361 is connected with the meter 330, while in the lower position of selector 331, the output of amplifier 429 is supplied to the meter 330. Of course, the optical analyzer 300 may further include analogue to digital converters for converting the outputs of the amplifiers 361 and 429 to digital form for transmission to a remote computer, for example. It wil be apparent to those skilled in the art that the remote computer could be programmed to control the sequential actuation of relay 401 during each increment of scanning movement of the monitoring device 10 so as to obtain readings from each desired sampling region of the web 14 for each of the seven positions of the filter wheel 210. The remote computer would then be in a position to correspondingly determine the average optical characteristics of a given length section of the paper web 14, for example, and control suitable inputs to the paper machine so as to maintain desired optical characteristics of the paper being manufactured. Alternatively, of course, the arrangement of FIGS. 1–6 can be utilized simply to take readings from the meter 330 for each filter wheel position during scanning of the web, so as to obtain readings reflecting the optical characteristics of the length sections of the web so scanned. Still further, of course, the circuitry of FIGS. 5 and 6 can be utilized either with the monitoring device located in a fixed position relative to the width of the web (by means of a C-type frame), or with the device off-line from the paper machine, so as to obtain desired readings from the meter 330 for each position of the filter wheel 210 during optical excitation of a single sheet sample of the web held in a sample holder so as to be disposed essentially as indicated for the web 14 in FIG. 3.

EXEMPLARY COMMERCIALLY AVAILABLE COMPONENTS

Commercially available components which are included in the present design of FIGS. 1–6 are as follows.

Main power supply. Lambda Electronics Corporation Model LQS-DA-5124 providing a direct current (DC) output voltage of 24 volts and a maximum current at 40° C of 5 amperes.

Reed switches. For reflectance amplifier gain settings-Model MMRR-2, and for transmittance amplifier gain settings-Model MINI-2, manufactured by Hamlin, Inc. The relays in the lower sensing head of Type 821A of Grigsby-Barton, Inc.

Operational amplifiers, Model 233J chopper stabilized amplifiers of Analog Devices, Inc. Model 904 power supply supplying plus or minus 15 volts with a minimum full load output current of plus or minus 50 milliamperes.

Digital panel meter (used for off-line studies and for on-line operation before being interfaced with the computer). Weston Model 1290.

Filter wheel advance solenoid. Type T 12×13-C-24 volt DC flat plug plunger of Guardian Electric Manufacturing Company. Antibottoming washer made of polyurethane rubber. Operation of the solenoid until interfaced with the computer has been with the use of a time adjusted relay, namely a Model CG 102A6 transistorized repeat cycle timer of G. & W. Eagle Signal Co.

Filter wheel drive motor. Type 1AD3001 Siemens brushless DC motor. The drive belt and pulleys for coupling the motor 209 with the the shaft 208 are specified as positive drive belt FS-80 and positive drive pulleys FC5-20 and FC5-40 of PIC Design Corporation, a Benrus subsidiary. The belt has a stainless steel core and the pulleys have a ¼ inch diameter bore.

COMPUTER INTERFACING

In preparing the monitoring device for on-line operation on the paper machine, the zero to 140 millivolt DC signals from the sensing heads will be supplied to respective emf-to-current converters of component 501, FIG. 6. As an example, Rochester Instrument Systems Model SC-1304 emf-to-current converters may be used. Such a converter will provide an output of 10 to 50 milliamperes DC suitable for driving an analog to digital converter at the computer. The emf-to-current converters will provide an isolated input and output so that grounding will not be a problem.

The converters of component 501, will be housed with optical analyzer 300, FIG. 5, and will connect with respective points thirty one of Groups five hundred and six hundred (not shown) at the control computer analog signal input via conductors such as indicated at 502 and 503 in FIG. 6.

Conductors 505 and 506, FIG. 6, associated with filter wheel indexing solenoid 240, FIGS. 3 and 6, may extend within control conduit 312, FIG. 5, and connect with the control computer output terminals at a location designated Group forty two hundred and six, point nineteen (not shown). (Switch 334 should remain open (off) during computer operation of FIGS. 1–6.)

Conductors 359 and 360, FIG. 6, may connect with an input of the control computer at a location designated Group fourteen hundred, point twenty-three (not shown).

DISCUSSION OF AN EARLIER PROTOTYPE SYSTEM

Structure and Operation of a Prototype Optical Monitoring Device

A prototype optical monitoring device was first constructed so as to test the feasibility of the concepts of the present invention. As a result of the experimental work with the prototype system, a preferred system has been designed and will hereinafter be described in greater detail. Since the operation of the prototype system is somewhat different from that of the later designed system, a description of the prototype system will serve to illustrate alternative features and an alternative method of operation in accordance with the present invention.

In the original setting up of the prototype system, the upper and lower sensing heads should be brought into proper alignment and spacing. The spacing should be just under ¼-inch between the case 110 and the surface of the diffusing glass of window 135. (In the prototype unit, there were no additional parts between the case 110 and window 135 such as the shoe plate 122 shown in FIG. 3.) The lower sensing head should be moved laterally in all directions to locate the point where the maximum reading occurs from photocell 260 as well as the point of least sensitivity to relative movement of the upper and lower sensing heads. In an initial calibration of the prototype monitoring device, potentiometers are included as part of the resistance means 371–377 and 431–437 and are adjusted for the respective positions of the filter wheel 210 to give the correct readings for the reflectance and transmittance of the diffusing glass 135 (in the absence any paper sample between the upper and lower sensing heads). The values which were used in this initial calibration are indicative of percentage absolute reflectance and transmittance on a scale of 100, and are as follows:

Table 1

| Table Showing Exemplary Calibration for the Prototype System- Diffusing Glass Reflectance and Transmittance Values With No Paper Specimen Present | | |
|---|---|---|
| Filter Wheel Position No. | Reflectance Value, RSD (Millivolts) | Transmittance Value, TSD (Millivolts) |
| 1 | 35.4 | 54.0 |
| 2 | 35.0 | 56.1 |
| 3 | 34.4 | 56.9 |
| 4 | 34.6 | 56.6 |
| 5 | 34.7 | 56.4 |
| 6 | 34.5 | 56.6 |
| 7 | 34.8 | 0.6* |

The readings in millivolts can be converted to other desired units by comparing the readings in millivolts for a given paper specimen with the readings obtained with a standard laboratory instrument, measuring the reflectance of the specimen with the laboratory instrument while backin the paper sheet with a piece of Lucalux and a black body. By measuring the reflectance of the single sheet backed with a black body (no fluorescence), the value of transmittance for the specimen can be calculated and this calculated value utilized for calibrating the lower sensing head. If the fluorescent component is included in the laboratory instrument, and if fluorescence is involved, the fluorescence component can be determined by means of a standard reflection meter, and the fluorescent component can then be subtracted from the measured data before making the calculation of transmittance.

The laboratory testing of the prototype system confirmed that a monitoring device such as illustrated in FIGS. 1–4 should have a potential accuracy equal to that of comparable off-line testers provided certain web scanning requirements are met.

Laboratory tests were run on color standard samples of the grades and colors usually run on the paper machine shown in FIGS. 1 and 2. In addition, a variety of opaques, and a variety of colored 50 pound and 70 pound offsets were included in the tests. A four centimeter diameter circle was scribed on each sample to insure that all tests would be done within the same 12 square centimeter section of the sample. Values of $R_o$, $R_{oo}$, and TAPPI opacity measurements were made on the available standard laboratory instruments. All test were made on the felt side of the sample with the grain in the standard direction. For $R_{oo}$ measurements, the samples were backed by piles of tabs cut from the edge of the same sheet of paper. In addition to the TAPPI opacity measured on the standard opacimeter, TAPPI opacity was calculated via Kubelka-Munk theory from data obtained with a standard automatic color-brightness tester.

The same paper samples were clamped into a holder which held the sample under tension with the lower head of the monitoring device bellying ⅛-inch to ¼-inch into the sheet. The grain of the sheet was oriented parallel to the longitudinal axis of the upper sensing head (that is the machine direction of the sheet was in the same orientation as would occur on the paper machine as indicated in FIGS. 1 and 2). The felt side was always up. Care was taken to make sure that the tested area was within the twelve square centimeter circle scribed on the sample.

The transmittance and reflectance readings were taken from a digital volt meter attached to the output terminals of amplifiers 361 and 429. Calibration data was taken off the Lucalux with no sheet present. Test values were taken on all filters with the sheet in place. The transmittance and reflectance values were keyed into a standard calculator with the calibration data. The calculator was programmed to calculate the color (in C.I.E. X, Y, Z, for example), fluorescent component, brightness, TAPPI opacity and printing opacity (based on $Y_c$). By supplying the basis weight, the computer could also be requested to calculate $s$, the scattering coefficient (an index of the effect of pigment efficiency and fiber surface area), and $k$, the absorption coefficient (an index of the effectiveness of dyes in the sheet). The coefficients $s$ and $k$ are essentially independent of basis weight. Kubelka-Munk theory is the basis of the calculations used.

All of the samples were tested without changing the relative position of the two sensing heads. One set of data was obtained with the heads in a variety of positions to determine the effect of geometric variations.

Since fluorescence is not compatible with Kubelka-Munk theory, the prototype system was carefully designed so that all data used for Kubelka-Munk analyses have excluded fluorescence. The prototype system measures fluorescence separately. A fluorescent contribution is determined from the prototype data by subtracting the Z distribution reflectance without fluorescence (filter wheel position No. 4) from the Z distribution reflectance with fluorescence (filter wheel position No. 7), and multiplying by the appropriate factor.

An independent check on fluorescence measurements, a modified brightness tester was utilized which had a filter wheel allowing for standard brightness and Z distribution filters to be put in the reflected beam. In addition, the filter wheel contained brightness and Z distribution filters which had been modified by removing the ultraviolet absorbing component of these filters. A special mount allows the operator to put the appropriate ultraviolet absorbing filter in the incident beam. Thus, measurements of brightness and C.I.E. Z tristimulus, with and without fluorescence, could be made. Fluorescent contributions were calculated by difference. Some measurements were made on single sheets with a standard backing. Most of the samples were measured with an infinite pack of tabs. The incident beam filter of the prototype's No. 7 position was such that it permitted about twice the standard quantity of ultraviolet light to strike the specimen. Consequently, measurements of the fluorescent contribution measured on the modified brightness tester and the prototype system correlated well (correlation coefficient of 0.992) but the modified brightness tester value is only 0.528 as large as that measured by the prototype system. Calculations of prototype data now involve calculation of the fluorescent component by multiplying the difference of filter positions No. 7 and No. 4 by 0.528.

Because only one fluorescent dye (Tinopal) in all of the paper specimens was used, the fluorescent contribution needed to be measured only once. The prototype data provides a basis for measuring the fluorescent component Z. Measurements by an independent laboratory showed that the paper specimens do not fluoresce significantly in the X (red) or Y distributions; therefore, fluorescent contributions need only be determined for the blue colored distributions. A linear regression was run on the independent laboratory data which demonstrated that the fluorescent component for X (blue) can be predicted by multiplying the fluorescent component for Z by1.204. A regression run on fluorescent data from the modified brightness tester shows that the fluorescent contribution for brightness can be calculated by multiplying the fluorescent contribution for Z by 0.864. In summary, fluorescent contributions are calculated by the following formulas:

$F_Z = 0.528$ (Z reflectance with fluorescence minus Z reflectance without fluorescence.)

$F_{X(blue)} = 1.204\ F_Z$ $F_{Brightness} = 0.864\ F_Z$

These fluorescent contributions are added to the respective calculated $R_{oo}$ values when calculating optical properties from prototype data. The test results for fluorescent and non-fluorescent papers agree with values measured on the standard automatic color-brightness tester.

DISCUSSION OF THE RESULTS OF MECHANICAL LIFE TESTING OF THE PROTOTYPE SYSTEM AND DESIGN FEATURES SELECTED FOR THE PREFERRED SYSTEM IN LIGHT OF SUCH LIFE TESTING

The following details concerning the results of life testing of the prototype systems are considered to reflect minor problems of construction and operation which considered individually are readily corrected for by those skilled in the art. In order to minimize the burden of the total number of such minor problems, and thus to expedite practice of the prototype system, solutions to the various problems which were encountered are briefly referred to.

The filter wheel is advanced by a low torque stallable motor. A timing belt links sprockets on the motor and the filter wheel shaft. The original timing belt had a dacron core. The core of the original belt broke in two places resulting in stretching and eventual loss of teeth. Uneven rate of rotation of the filter wheel occurred due to binding of the belt. Eventually, the plastic drive sprocket broke. Both sprockets were replaced with stainless steel sprockets and the timing belt was replaced with a belt containing a steel core. Installation of the steel sprockets and steel core belt revealed that excessive belt tension could stall the motor. The motor mount holes were slotted allowing the motor to pivot slightly around one mounting screw. Belt tension was adjusted by pivoting the motor. It is concluded that future models should include an idler wheel or some other means of adjusting the tension of the timing belt.

Some problems were experienced with respect to indexing of the filter wheel with the ratchet arm sticking on the tooth so that the ratchet arm does not clear the tooth when a command is given to index the filter wheel. The remedy has been to reduce the roughness of the mating surfaces by filing on the tooth, or smoothing the tooth with a stone. In future models, the shapes and/or smoothness of the ratchet arm and the teeth should be altered to minimize sticking. One solution would be to provide the ratchet arm and the teeth with highly polished mating surfaces.

The ratchet arm is lifted by a 24 volt direct current solenoid. After some time, the plunger of the solenoid became magnetized and would stick to the inside of the coil. This "hanging up" would prevent the ratchet arm from catching the next tooth. A resistor was installed in series with the solenoid coil to reduce the strength of the magnetic field. The plunger of the solenoid was coated with a special material. The coated plunger worked well for about three months before it, too, magnetized enough to hang up. The solution adopted was to provide the solenoid with a flat topped plunger which is stopped at the end of its stroke by a bumper of rubber-like material.

The response of a photocell is somewhat temperature sensitive. For this reasons, it is necessary to keep the photocells at a constant temperature. Ambient temperatures on the O-frame of the No. 6 paper machine indicated in FIGS. 1 and 2 have been measured as high as 118° F (48° C.) in the summer. The photocells in both heads are mounted in massive metal blocks. Each metal block has four thermistor heaters mounted in close proximity to the photocell. These thermistors have switching temperatures of 55° C, (that is about 130° F). The intention of this design was to add enough heat to the instrument to hold the temperature steady at about 55° C. During bench studies, this temperature was never reached due to the low capacity of the heaters. At machine room temperatures, however, the instrument temperature may reach 55° C.

During the bench studies, it was found that the heaters did minimize temperature variations. The few degrees of temperature variation that were observed during normal operation usually occurred slowly. Changes in instrument temperature affected the output signal less than acticipated. Based on this experience in the laboratory, the maximum variation in head temperature should be less than 3° F per hour. Temperature variations of this magnitude will not have a significant effect on the output signal. Long term temperature changes would be corrected for by the calibrations each time the head goes off web.

In the laboratory, there was a minimum of dirt problems. On the machine, however, the hole could allow dirt to enter the upper head. Up to a point, dirt on the lenses and filters will be corrected for by the periodic calibration routine. Excessive dirt, however, will reduce the sensitivity of the instrument and may even affect its accuracy. Periodic cleaning of the lenses and filters will be required. If dirt accumulates too rapidly, it may be necessary to attach an air purge to the upper head.

The lower head of the prototype system is completely sealed so that no dirt problem is anticipated inside the lower head. Because the Lucolux window is in contact with the sheet, friction will keep it clean.

Most of the filters consisted of two or three component parts. There have been some problems with dirt getting between the components of the filters.

The case on the lower head as well as the case on the upper head should allow most general maintenance and trouble-shooting to be done without dismounting the head. A completely removable case would be desirable. At a minimum access should be provided for the following: (1) convenient light bulb change, (available on the prototype), (2) cleaning of lenses, (available on the prototype), (3) cleaning of the filters. (Access is presently available to one side of each filter. The side which is most likely to collect dirt is not accessible in the prototype.) (4) The amplifier. The amplifier is a standard plug-in module. In the event of a breakdown it could be replaced in seconds if it is accessible. Furthermore, it is necessary to remove the amplifier to do any trouble-shooting on the gain circuitry. (5) The circuit board holding all of the gain control resistors. The choice of gain circuitry is controlled by reed switches which are not accessible on the prototype without a partial disassembly of the instrument. Malfunctions of the reed switches, however, can easily be diagnosed by removing the amplifier and taking resistance measurements on the gain control circuits. There is also the possibility of mechanical or electrical damage to a resistor or a potentiometer mounted on this circuit board. With proper access a damaged part could be replaced in five to twenty minutes. (6) The photocell. With proper access, the photocell could be replaced quickly and easily. (7) The heater. The heater are adjacent to the photocell and are generally just as easily serviced. (8) Indexing mechanism. The present accessibility to the ratchet teeth, rachet arm and solenoid is adequate but not very convenient on the prototype. A certain amount of access to these parts is needed to correct chronic indexing problems such as sticking and "hanging up."

The filters are presently mounted in the filter wheel of the prototype by spring clips. Most of the filters are compound filters containing as many as four component pieces of glass. During laboratory trials, increases in the optical density of a filter were frequently observed which could not be corrected by cleaning the surfaces of the filter. Upon removing one of the filters, it was discovered that foreign material was collecting between the components of the compound filter. The use of lens cleaning solution on the filters may have accelerated the problem if capillary action drew foreign material between the components. A set of gaskets and some type of threaded mount should be used to mount the filters in such a way as to minimize foreign material (including cleaning solutions) from getting between the components of compound filters.

In mounting the prototype sensing heads on an O-frame, it is necessary to bring the geometric alignment of the heads as close to their optimum relationship as possible. The original intention was to set the gap between the heads with the aid of a spacer; however, flexibility of the sheet metal case of the prototype upper sensing head prevented the use of a spacer for setting the gap. Accordingly, the shoe plate 122 of the new upper sensing head shown in FIG. 3 has been made of a thickness and consequent rigidity so as to enable the use of a spacer gauge to set the gap between the upper and lower heads. (The gap is reduced by 1/16 inch to 3/16 inch because of the thickness of shoe plate 122.)

The gap between the heads is a most critical dimension as far as calibration and reproducability is concerned. In the prototype it was intended to calibrate relative to an average gap, thus correcting the readings for variations in the gap from the average gap.

One of the criteria used in designing the prototype was minimum head length in the machine direction. Unfortunately, the upper head was turned 90° in order to give the prototype unit the same geometry as the General Electric Brightness Meter, Automatic Color-Brightness Tester, and Hunterlab Color Meter. In this new position, the prototype head is 12 ¼ inches long in the machine direction plus 2 ½ inches for cable connectors. Redesign should be possible to reduce the machine direction dimension to about 8 inches and to relocate the position of the cable connections.

The lining of the case for the upper head should be matte as well as black to prevent reflection of ambient light within the case and a possible spurious effect on the photocell reading.

CONCLUSIONS FROM MECHANICAL TESTING OF THE PROTOTYPE SYSTEM

Following the correction of miscellaneous start up problems the prototype system was found to function well mechanically. As a test of its durability, the prototype system was placed in continuous operation for a period of over ten months and no serious mechanical problems resulted except the failure of the solenoid. The solenoid failure was expected and the replacement solenoid is of a design which is expected to give a long service life. The light application of silicone lubricant spray to the indexing control ratchet arm and cooperating teeth corrected a problem of malfunctioning of the filter wheel indexing mechanism (which occurred on two occasions during the ten months). The prototype system was not intended to be a low maintenance instrument; however, the experience during the durability test with the prototype in continuous operation indicates that the prototype system should operate on a paper machine with an acceptably small amount of down time.

DISCUSSION OF LABORATORY TESTING OF FIGS. 3–6

Laboratory Operation of the System of FIGS. 3–6

In the prototype system, potentiometers are included as part of the resistance means 371–377 and 431–437 and are adjusted for the respective positions of the filter wheel 210 to give desired values such as given in the foregoing Table 1. In the preferred system of FIGS. 3–6, these potentiometers for adjusting amplifier gain are omitted and are replaced with fixed resistors 371–377 and 431–437 selected to give scale readings from meter 330 in the respective filter wheel positions which are well above the values given in the preceding Table 1. This is intended to improve the stability and increase the sensitivity of measurement.

In calculating optical parameters from measurements relative to various samples, values were first established for the reflectance RD of the diffuser 135, FIG. 3, in the absence of a paper specimen, for each filter wheel position. Initially calculated values for RD were used in a first computation of optical values, and then the values of RD were adjusted slightly to give the best agreement with the corresponding optical measurements by means of the standard automatic color-brightness tester. The following table shows the reflectance values which were established for certain laboratory testing of the system of FIGS. 3–6.

Table 2

| Table Showing Reflectance of the Diffusing Glass With No Paper Specimen Present in a Laboratory Test of the System of Figs. 1–6 | | |
|---|---|---|
| Filter Wheel Position No. | Symbol | Diffusing Glass Reflectance Value |
| 1 | RD1 | 0.349 |
| 2 | RD2 | 0.347 |
| 3 | RD3 | 0.355 |
| 4 | RD4 | 0.349 |
| 5 | RD5 | 0.354 |
| 6 | RD6 | 0.354 |
| 7 | RD7 | 0.349 |

The transmittance of the diffusing glass 135 need not be known since the ratio of the transmittance of the diffusing glass and paper (in series) to the transmittance of the diffusing glass is employed in calculating the desired optical parameters.

A computer program was developed to process the data collected during laboratory operation of the monitoring device 10 as well as to compare the calculated reflectance value $R_{oo}$ and the calculated fluorescent components with the data collected with the standard automatic color-brightness tester. A listing of the symbols employed in a symbolic statement of the computer program in the Fortran computer language utilized in this laboratory study is set forth in Table 3 on the following pages.

Table 3

| Listing of Symbols (Including Input Data Symbols and Output Data Symbols With a Brief Indication of Their Significance). | |
|---|---|
| Input Data Symbols | |
| RSD | OMOD scale reading for reflectance with no paper specimen in place. (Filters 1 through 6.) |
| RSP | OMOD scale reading for reflectance with paper specimen in position. (Filters 1 through 6.) |
| TSD | OMOD scale reading for transmittance with no paper specimen in place. (Filters 1 through 6.) |
| TSP | OMOD scale reading for transmittance with paper specimen in position. (Filters 1 through 6.) |
| RSD7 | OMOD scale reading for reflectance with no specimen in place. (No. 7 filter.) |
| RSP7 | OMOD scale reading for reflectance with paper specimen in position. (No. 7 filter.) |
| AR$_\alpha$FC | ACBT reflectance including the fluorescent component. |

Table 3-continued

Listing of Symbols (Including Input Data Symbols and Output Data Symbols With a Brief Indication of Their Significance).

Input Data Symbols

| Symbol | Description |
|---|---|
| AFC | ACBT fluorescent component. |
| RSD4 | OMOD scale reading for reflectance with no paper specimen in place. (No. 4 filter.) |
| RSP4 | OMOD scale reading for reflectance with paper specimen in position. (No. 4 filter.) |
| GC | Grade Correction as determined by the difference between $R_xFC$ and $AR_xFC$ for each sample and each filter. |
| $R_o$ | Reflectance of a single sheet backed with a black body (no fluorescence) as calculated from OMOD data. |
| T | Transmittance of a single sheet backed with a black body (no fluorescence) as calculated from OMOD data. |
| $R_x$ | Reflectance of an opaque pad (no fluorescence) as calculated from OMOD data. |
| $R_xFC$ | Reflectance of an opaque pad (including fluorescence) as calculated from OMOD data. |
| $AR_xFC$ | Reflectance of an opaque pad (including fluorescence) ACBT. |
| DIFF | Difference between $R_xFC$ and $AR_xFC$. |
| FC | Fluorescent component OMOD. |
| AFC | Fluorescent component ACBT. |
| GC | Grade Correction as determined by the difference between $R_xFC$ and $AR_xFC$ for each sample and each filter. |

Additional Symbols (Used in the Computation of the Output Data from the Input Data)

| Symbol | Description |
|---|---|
| RK | Reflectance correction factor (assigned a value of 1.000 for laboratory operation). |
| TK | Transmittance correction factor (assigned a value of 1.000 for laboratory operation). |
| RD | Value representing the absolute reflectance of the diffuser (on a scale of zero to 1.000) as adjusted to give best agreement with optical measurements by means of the standard automatic color-brightness tester. (The values given in Table 2 are used for laboratory operation.) |
| RPD | Reflectance of paper specimen when backed with the diffuser, as calculated from current values of RK, RD, RSD, and RSP. |
| TPD | Transmittance of paper specimen and diffuser in series, as calculated from current values of TK, TSD, and TSP. |

In the foregoing listing of symbols, the letters of the symbol OMOD are taken from the phrase on-machine optical device; however, this particular section of the specification refers to a system essentially conforming to the system of FIGS. 3–6 operated to measure optical properties of individual paper sheets under laboratory conditions. (The laboratory work here reported was with an earlier version of the monitoring device designed for on-machine operation, prior to adoption of a thickened shoe plate 122. The standard spacing between the upper and lower sensing heads for the earlier version was ¼ inch, rather than 3/16 inch as with the final version of on-machine device as specifically shown in FIG. 3.) The OMOD scale readings are obtained from the meter 330, FIGS. 5 and 6, with the filter wheel 210, FIGS. 3 and 4, in the respective positions to activate the respective filters 281–286 (indicated as "Filters 1 through 6" in the preceding listing) and to activate filters 287 and 288 (indicated as "No. 7 filter" in the listing), and with switch 331, FIG. 5, in its upper position to measure reflectance, and in its lower position to measure transmittance. As to reflectance measurements, the cavity 145 is considered to form essentially a black body backing for the diffusing glass 135.

The symbol "ACBT" in the foregoing listing of symbols is used to designate a measurement made on the standard commerically available automatic color-brightness tester. The brightness measurement obtained from the ACBT represents a value accepted as standard in the U.S. Paper industry. A further appreciation of the importance of the fact that the OMOD measurements can closely conform to this industry standard is gained from a consideration of the article by L. R. Dearth et al "A Study of Photoelectric Instruments for the Measurement of Color Reflectance, and Transmittance, XVI. Automatic Color-Brightness Tester," *Tappi, The Journal of the Technical Association of the Pulp and Paper Industry*, Vol. 50, No. 2, February 1967, pages 51A through 58A. As explained in this article, the ACBT is photometrically accurate, and the spectral response is correct for the measurement of both color and standard brightness. The spectral response of the ACBT very nearly matches the theoretical CIE functions as indicated by the special technique for determining spectral response. This involves the determination of the tristimulus values for deeply saturated colored glass filters a very rigorous check on the spectral response, especially when it is noted that colored papers are less saturated.

The symbols in the foregoing Listing of Symbols which as shown include lower case characters may also be written exclusively with capital letters. This form of the symbols is convenient for computer printout. The alternate forms of these symbols are as follows: $AR_{oo}FC$ or AROOFC; $R_o$ or RO; $R_{oo}$ or ROO and $R_{oo}$ FC or ROOFC.

Table 4

Symbolic Statement of the Computer Program (Used for Processing the Data Obtained During the Laboratory Operation of the System of Figs. 3–6)

```
6PS FORTRAN D COMPILER
                C OMOD (220)
S.0001          WRITE (6,2001)
S.0002   2001   FORMAT (1H, 'SAMPLE', 6X,'
                RD', 12X,'T', 12X,'ROO',9X,
                'ROOFC',9X, 1'AROOFC', 10X,
                'DIFF', 7X, 'FC', 7X, 'AFC', 7X,
                'GC',/)
S.0003          READ (5,1000) RK, TK, RD1,
                RD2, RD3, RD4, RD5, RD6
S.0004   102    M=0
S.0005          READ (5,1000) RSD4, RSP4
S.0006   1000   FORMAT (10F8.0)
S.0007   100    READ (5,1001) IA, IN, ID, RSD,
                RSP, TSD, TSP, RSD7, RSP7,
                AROOFC, AFC, R
S.0008   1001   FORMAT (I2, I2, A4, 9F8, 0)
S.0009          GO TO (11,12,13,14,15,16), IN
S.0010   11     RD=RD1
S.0011          GO TO 17
S.0012   12     RD=RD2
S.0013          GO TO 17
S.0014   13     RD=RD3
S.0015          GO TO 17
S.0016   14     RD=RD4
S.0017          GO TO 17
S.0018   15     RD=RD5
S.0019          GO TO 17
S.0020   16     RD=RD6
S.0021   17     RPD=((RD*RSP*RK)/RSD)
S.0022          RPD4=RD4*RSP4*RK/RSD4
S.0023          TPDOTD=(TSP*TK)/TSD
S.0024          RO=(RPD-(RD*(TPDOTD**2)))/(1.-
                (RD* TPDOTD)**2)
S.0025          T=(TPDOTD*(1.-(RD*RPD)))/1.-
                (RD*TPDOTD)**2)
S.0026          A=((1.+(RO**2))-(T**2))/RO
S.0027          ROO=(A/2.)-SQR[(((A/2.)**2)-1.)]
S.0028          RPD7=RD4*RSP7*RK/RSD7
S.0029          IF (IN-2)1,2,3
S.0030   3      GO TO (7,7,7,4,7,7), IN
```

Table 4-continued

Symbolic Statement of the Computer Program
(Used for Processing the Data Obtained During the
Laboratory Operation of the System of Figs. 3-6)

```
6PS FORTRAN D COMPILER
        C OMOD (220)
S.0031  1   FC=(RPD7-RPD4)*.450
S.0032      GO TO 6
S.0033  2   FC=(RPD7-RPD4)*.570
S.0034      GO TO 6
S.0035  4   FC=(RPD7-RPD4)*.510
S.0036  6   ROOFC=ROO+FC
S.0037      GO TO 30
S.0038  7   ROOFC=ROO
S.0039      FC=0.0
S.0040  30  IF (IA-2)18,19,19
S.0041  18  ROOFC=ROOFC+R
S.0042      GO TO 20
S.0043  19  ROOFC=ROOFC-1
S.0044  20  DIFF=ROOFC-AROOFC
S.0045      GO TO (21,22), IA
S.0046  21  WRITE (6,2000)ID,RO,T,ROO,
            ROOFC, AROOFC,DIFF,FC,AFC,R
S.0047  2000 FORMAT (IH A4,7X,2(F8.6,4X),4
            (F10.6,4X),2(F5.4,4X),'+',F4.3)
S.0048      TO TO 23
S.0049  22  WRITE (6,2002)ID,RO,T,ROO,
            ROOFC,AROOFC,DIFF,FC,AFC,R
S.0050  2002 FORMAT (IH,A47X,2(F8.6,4X),4
            (F10.6,4X),2(F5.4,4X),'-',F4.3
S.0051  23  M=M+1
S.0052      IF (M-6) 100,102,102
S.0053  END
        SIZE OF COMMON 00000
        PROGRAM 01930
END OF COMPILATION MAIN
```

In the foregoing Table 4, the symbols representing basic mathematical operations were as follows:

| Operation | Symbol | Example |
|---|---|---|
| Addition | + | A+B |
| Subtraction | − | A+B |
| Multiplication | * | A*B |
| Division | / | A/B |
| Exponentiation | ** | $A**B(A^B)$ |
| Equality | = | A=B |

To indicate more concretely the calculations which are performed, the following Table 5 will illustrate exemplary input and output data for a given sample. The meaning of the various symbols will be apparent from the listing of the symbols of Table 3:

Table 5

Table Showing Exemplary Input and Output Data for a Given Sample

Sample No. 1, white Nekoosa Offset-60 pound paper, specimen A RK=1.000, TK=1.000

| Filter Wheel Position No. Input Data | 1 | 2 | 3 | 4 | 5 | 6 |
|---|---|---|---|---|---|---|
| RD | 0.349 | 0.347 | 0.355 | 0.349 | 0.354 | 0.354 |
| RSD | 0.515 | 0.529 | 0.583 | 0.636 | 0.525 | 0.596 |
| RSP | 1.161 | 1.187 | 1.339 | 1.422 | 1.191 | 1.357 |
| TSD | 1.422 | 1.625 | 1.627 | 1.702 | 1.625 | 1.546 |
| TSP | 0.236 | 0.256 | 0.354 | 0.277 | 0.335 | 0.326 |
| RSD7 | 0.568 | 0.568 | 0.568 | 0.568 | 0.568 | 0.568 |
| RSP7 | 1.381 | 1.381 | 1.381 | 1.381 | 1.381 | 1.381 |
| AROOFC | 0.837 | 0.829 | 0.847 | 0.830 | 0.839 | 0.844 |
| AFC | 0.034 | 0.034 | 0.0 | 0.036 | 0.0 | 0.0 |
| RSD4 | 0.636 | 0.636 | 0.636 | 0.636 | 0.636 | 0.636 |
| RSP4 | 1.422 | 1.422 | 1.422 | 1.422 | 1.422 | 1.422 |
| GC | −0.006 | −0.014 | −0.021 | −0.007 | −0.009 | −0.012 |

Table 5

Table Showing Exemplary Input and Output Data for a Given Sample - continued

| Filter Wheel Position No. Output Data | 1 | 2 | 3 | 4 | 5 | 6 |
|---|---|---|---|---|---|---|
| RO | 0.779777 | 0.772313 | 0.803330 | 0.773563 | 0.792249 | 0.794690 |
| T | 0.120798 | 0.115319 | 0.155529 | 0.118812 | 0.148337 | 0.151546 |
| ROO | 0.812093 | 0.800173 | 0.874419 | 0.803542 | 0.849399 | 0.856230 |
| ROOFC | 0.836794 | 0.824838 | 0.853419 | 0.831337 | 0.840399 | 0.844230 |
| AROOFC | 0.837000 | 0.829000 | 0.847000 | 0.830000 | 0.839000 | 0.844000 |
| DIFF | −0.000206 | −0.004162 | 0.006419 | 0.001337 | 0.001399 | 0.000230 |
| FC | .0307 | .0387 | .0 | .0348 | .0 | .0 |
| AFC | .0340 | .0340 | .0 | .0360 | .0 | .0 |
| GC | −.006 | −.014 | −.021 | −.007 | −.009 | −.012 |

In the foregoing table showing exemplary input and output data, the input and output data symbols have been shown as they are actually printed out by the computer with all letters capitalized. In the text, certain of the input and output data symbols are shown in a more conventional manner with subscripts since the symbols are more familiar in such form.

The data such as exemplified in Table 5 are based on a single determination for each specimen. The "grade correction" GC is based on the average difference between $R_{oo}FC$ and $AR_{oo}FC$ for two specimens, specimens A and B.

The data as exemplified in Table 5 show that there is generally good agreement between the calculated $R_{oo}FC$ and $AR_{oo}FC$ values. The spread in values for the duplicate specimens (A and B) is good with the exception of several samples. Some difficulty was experienced in positioning the specimen of the monitoring device 10 to give reproducible results. The difficulty should be minimized when the unit is placed "on-machine." The grad correction GC takes this discrepancy into consideration so the correction should be established "on-machine."

The RD values shown in Table 5 were punched into the first data card along with the values for RK and TK for input to the computer in advance of a desired computation. The factors RK and TK were included as factors in the computations so that the transmittance and reflectance values could be adjusted independently, if desired. In this evaluation, RK and TK were left at 1,000. (Calculated values for RD were used in a first computer run and then the values were adjusted slightly to give the best agreement with the standard automatic colorbrightness tester. The values for RD shown in Table 5 are the slightly adjusted values utilized in obtaining the data discussed in this section of the specification.)

A second set of data for the same fourteen samples was collected using the monitoring device in the same condition as for the collection of the data previously given. All of the variables were left the same to see how closely the data could be reproduced for the identical specimens. The agreement was quite good except for samples 8 and 14. It appears that the paper may not have been lying flat in one or the other tests. The grade correction GC on some of the grades was changed and the second set of data was again calculated for samples 1, 2, 4, 5, 6, 8 and 14. This improved the agreement between the monitoring device and the standard automatic color-brightness tester.

The reflectance head of the monitoring device was then lowered 0.025 inch and another set of data was collected for the same seven samples. The same ACBT data was used. The data show that lowering the reflectance head reduces the reflectance while transmittance remains essentially unchanged. The effects are not as large as was expected and could be corrected through adjustment of RK; however, the variables RK, TK and GC were again held constant.

The reflectance head was then raised to a spacing of 0.050 inch (0.025 inch above the normal position for tests), and another set of data was collected for the same seven samples. The effects were larger than when the reflectance head 11 was lowered. Again, an adjustment of RK would improve the agreement.

It was concluded from these test results that a change of plus or minus 0.025 inch from "normal position" is larger than can be tolerated. An estimate of a resonable tolerance, based on this and earlier work, would be plus or minus 0.010 inch from "normal position."

All of the variables used in calculating the data for samples 1, 2, 4, 5, 6, 8 and 14, after the initial change in the grade correction GC, were held the same to determine the effects of changing the reflectance head position. The same input data for the case of the reflectance head being raised 0.025 inch were processed again but with RK equal to 0.975 instead of 1.000. This reduces the reflectance value to the proper level. The data obtained in this way show good agreement between the monitoring device and the standard automatic color-brightness tester. Apparently the factor RK can be used quite effectively in adjusting for some variation in the geometric relationship of the upper and lower sensing heads. It would be preferred, of course, to maintain proper alignment and spacing.

A second set of samples were evaluated after returning the reflectance head to its normal spacing from the transmittance head. Before calculating new output data, the computer program of Table 4 was corrected in statements S.0022 and S.0028 by changing RD to RD4. The corrected computer program has been shown herein since the error in the previously referred to data was insignificant in most cases. Thus with the corrected computer program, the input data for the second set of samples were processed. The values RK and TK were set to 1.000 and the same corrections were used as for samples 1, 2, 4, 5, 6, 8 and 14 previously referred to.

Conclusions drawn from all of the data are that the grade correction GC will handle resulting from less than ideal characteristics of the monitoring device 10 such as the relatively wide bandwidth of light transmitted in the various filter positions in comparison to the requirements of Kubelka-Munk theory and the fact that this theory applies strictly only to diffuse light rather than collimated light as actually employed in the illustrated monitoring device 10. This correction must be established "on-machine." Use of the diffusing glass 135 to calibrate the monitoring device 10 will handle changes in light level, photocell sensitivity and amplifier gain. The reflectances RD of the diffusing glass 135 for the various filters as established in the present work are set forth in the previous Table 2 entitled "Table Showing Reflectance of the Diffusing Glass With No Paper Specimen Present in a Laboratory Test of the System of FIGS. 1-6."

As previously mentioned, the transmittance of the diffusing glass 135 need not be known as the ratio of the transmittance of the diffusing glass and paper (in series), identified by the symbol TSP, to the transmittance of the diffusing glass 135, identified by the symbol TSD, is employed as will be apparent from the explanation of the calculations employed set forth hereinafter.

The fluorescent component is handled through the difference in reflectance as measured with the number 4 and the number 7 filters (RPD7 minus RPD4). The factors used in the object computations, for filters number 1, 2 and 4, are 0.500, 0.600 and 0.550 respectively. This means of determining the fluorescent contribution FC appears to be successful.

The factor RK whereby the reflectance can be adjusted to account for misalignment or incorrect spacing seems to function better than was expected.

The following examples will serve to explain the calculations of the output data for the different filter positions in greater detail.

Table 6

Table Showing
Exemplary Calculation of Paper
Optical Parameters

Calculation of $R_o$, T, $R_\infty$, FC and $R_\infty$FC from OMOD data with the No. 1 filter in position.
Input: RSD1, RSP1, TSD1, TSP1, RSD7, RSP7, TK, RK, RSD4, RSP4, RD1, RD4, and GC1
Calculation:
$RPD1 = (RD1 \times RSP1 \times RK)/RSD1$
$RPD4 = (RD4 \times RSP4 \times RK)/RSD4$
$RPD7 = (RD4 \times RSP7 \times RK)/RSD7$
$TPD/TD = (TSP1 \times TK)/TSD1$
$R_o = [RPD1-(RD1(TPD/TD)^2]/[1-(RD1(TPD/TD)^2)]$
$T = [(TPD/TD)(1-RD1 \times RPD1))]/[1-(RD1(TPD/TD)^2)]$
$A = (1+R_o^2-T^2)/R_o$ $R_\infty = (A/2) - \sqrt{(A/2)^2 - 1}$
FC = 0.500 (RPD7 - RPD4)
$R_\infty FC = R_\infty + FC + GC1$
Calculation of $R_o$, T, $R_\infty$, FC and $R_\infty$FC from OMOD data with the No. 2 filter in position Table 6-continued Table Showing
Exemplary Calculation of Paper
Optical Parameters Input: RSD2, RSP2, TSD2, TSP2, RSD7, RSP7, TK,
RK, RSD4, RSP4, RD2 and GC2.
Calculation:
$$RPD2=(RD2\times RSP2\times RK)/RSD2$$
$$RPD4=(RD4\times RSP4\times RK)/RSD4$$
$$RPD7=(RD4\times RSP7\times RK)/RSD7$$
$$TPD/TD=(TSP2\times TK)/TSD2$$
$$R_o=[RPD2 - (RD2(TPD/TD)^2)]/[1-(RD2(TPD/TD)^2)]$$
$$T=[(TPD/TD)(1-(RD2\times RPD2))]/[1-(RD2(TPD/TD)^2)]$$
$$A=(1 + R_o^2 - T^2)/R_o$$

$$R_x= (A/2) - \sqrt{(A/2)^2 - 1}$$
$$FC=0.600(RPD7 - RPD4)$$
$$R_xFC=R_x+FC+GC_2$$
Calculation of $R_o, T, R_x, FC$ and $R_xFC$ from OMOD
data with the No. 3 filter in position
Input: RSD3, RSP3, TSD3, TSP3, TK, RK, RD3 and
GC3
Calculation:
$$RPD3=(RD3\times RSP3\times RK)/RSD3$$
$$TPD/TD=(TSP3\times TK)/TSD3$$
$$R_o=[RPD3-(RD3(TPD/TD)^2)]/[1-(RD3(TPD/TD)^2)]$$
$$T=[(TPD/TD)(1-(RD3\times RPD3))]/[1-(RD3(TPD/TD)^2)]$$
$$A=(1+R_o^2-T^2)/R_o$$

$$R_x= (A/2) - \sqrt{(A/2)^2 - 1}$$
$$FC=0.0$$
$$R_xFC=R_x+FC+GC3$$
Note: The calculations for Filters No. 5 and 6 are
carried out in the same manner as for filter No. 3
except that the appropriate filter data are employed.
FC is made equal to zero for filters No. 3, 5 and 6
for all samples.
Calculation of $R_o, T, R_x, FC$ and $R_xFC$ from OMOD
data with the No. 4 filter in position.
Input: RSD4, RSP4, TSD4, TSP4, RSD7, TK, RK,
RD4 and GC4.
Calculation:
$$RPD4=(RD4\times RSP4\times RK)/RSD4$$
$$RPD7=(RD4\times RSP7\times RK)/RSD7$$
$$TPD/TD=(TSP4\times TK)/TSD4$$
$$R_o=[RPD4 - (RD4(TPD/TD)^2)]/[1-(RD4(TPD/TD)^2)]$$
$$T=[(TPD/TD)(1-RD4\times RPD4))]/[1-(RD4(TPD/TD)^2)]$$
$$A=(1+R_o^2 - T^2)/R_o$$

$$R_x= (A/2) - \sqrt{(A/2)^2 - 1}$$
$$FC=0.550(RPD7 - RPD4)$$
$$R_xFC=R_x+FC+GC4$$

On the basis of further experimental data, the factors relating the fluorescent component, as measured on the monitoring device, to the fluorescent component as measured with the standard automatic color-brightness tester, have the following presently preferred values for filter wheel position numbers 1, 2 and 4: 0.528, 0.636, and 0.456, respectively.

DISCUSSION OF THE ON-MACHINE SYSTEM OF FIGS. 1-6

Set Up Procedure For the System of FIGS. 1-6

In the prototype system, potentiometers were included as part of the gain control resistance means and were adjusted for the respective positions of the filter wheel 210 to give values correlated directly with absolute reflectance and transmittance of the diffusing glass, such as given in the foregoing Table 1. In the preferred system of FIGS. 1-6, however, these potentiometers for adjusting amplifier gain are omitted and are replaced with fixed resistors 371-377 and 431-437 selected to give scale readings from meter 330 in the respective filter wheel positions which are well above the values given in Table 1. The higher gain values for the amplifiers 361 and 429 in the preferred system are intended to provide improved stability and increased sensitivity of measurement.

The upper and lower sensing heads are placed at a spacing of 3/16 inch by means of a gauging plate made of 3/16 inch Teflon. The incident beam 133 forms a ligh spot of elliptical configuration on the planar upper surface 98 of the diffusing window 135. The major axis of the elliptical light spot has a length of about 5/8 inch and is parallel to the direction of web movement, i.e. the machine direction, while the minor axis has a length of about 3/8 inch and is at right angles to the machine direction. The reflected beam 137 consists of the total light reflected from a circular spot of approximately 3/8 inch diameter. This viewed area lies substantially within the elliptical illuminated area on surfce 98; however, the two essentially coincide in the direction of the minor axis of the illuminated spot.

Since the effective optical aperture 154, FIG. 3, of the lower sensing head is of a diameter of about 15/16 inch, the system will be insensitive to a certain amount of lateral offset between the optical axis 15 of the upper sensing head and the optical axis 515 of the lower sensing head.

In setting up the system, the position of the lower sensing head may be adjusted laterally so that the spot formed by the incident beam 133 is essentially centered on the surface 98 of window 135.

The optimum relationship between the upper and lower sensing heads can be precisely detected observing the reflectance output from the upper sensing head (in any position of the filter wheel 210) as the head are moved relative to one another while maintaining the spacing of 3/16 inch between the heads. When the correct geometrical relationship is attained between the incident beam 133, the reflected beam path 137 and the plane of the surface 98 of the window 135, the reflectance signal will have a maximum value.

With the upper and lower sensing heads in the optimum geometric relationship, and with the incident beam impinging on the central part of surface 98, it is considered that relative shifting between the upper and lower heads in the plane of surface 98 over a range of plus or minus ⅛ inch in any lateral direction should have an insignificant effect because of the flat planar configuration of surface 98.

DIRECT DIGITAL CONTROL ANALOG POINT SCAN SUBROUTINE OF FIG. 7

The program subroutine of FIG. 7 accepts digital information from the analog to digital converters of component 501, FIG. 6, at one second intervals. Referring to FIG. 7 where the blocks containing the flow chart steps are individually numbered in their operational sequence, the step 701 represents the entry into the subroutine at one second intervals. Step 702 shows the acceptance of an analog input and conversion to engineering units. Step 703 indicates saving such converted input as a process variable in a scan only file of the digital control computer. A type of control computer which has utilized such a scan program for a number of years for collecting data in an overall paper machine direct digital control system is the General Electric Company PAC 4020 Process Control Computer. Minor additions to the existing program routine will allow for the collection of the reflectance and transmittance data by means of the existing computer system. A suitable computer interface between monitoring device 10 and such a control computer has been described previously. Block 702 suggests that valid reflectance and transmittance values might be limited to a range from 0 to 1.0 units, for example. In this event the program could include provision for checking that the collected reflectance and transmittance values were within the range and for printing out a message or the like if invalid data is received.

Block 704 indicates the sequential reading of process data input points in a predetermined order until the last data input point has been scanned, whereupon the computer exits from the subroutine.

PROCESS FILE (FILE X) FOR THE DATA ACQUISITION AND DATA REDUCTION PROGRAMS

The arrangement of FILE X which is utilized during acquisition of data from the system of FIGS. 1–6 and conversion thereof to desired output paper optical quantities can be visualized from the following Table 7. In the first column of Table 7, sequential memory locations of the process file have been assigned sequential numbers beginning with zero. A convenient label has been assigned to certain groups of sequential memory locations, and this is also given in the first column. (The term FILE X is used to designate all of the locations zero through one hundred forty while subsequent labels refer to only the subadjacent group of sixteen locations or less.)

In general the significance of the various stored data will be apparent from the descriptions given in the righthand column of Table 7 and from the use of the stored data as indicated by the flow charts of FIGS. 8–20.

Table 7

| Label and Relative Location of File FILE X | Description of Stored Data |
|---|---|
| 0 | STATUS |
| 1 | PCW ADR LOOP P (REFLECTION CELL) |
| 2 | PCW ADR LOOP Q (TRANSMISSION CELL) |
| 3 | PFA GAGE HEAD POSITION (TAG 129) |
| 4 | SLOW DOWN COUNT |
| 5 | SLOW DOWN INITIAL VALUE COUNT |
| 6 | FILTER WHEEL POSITION INDEX EST. (1) |
| 7 | PFA BASIS WEIGHT AVG. (TAG. BOO) |
| 8 | MINIMUM ON SHEET HEAD POS. |
| 9 | INITIALIZATION INDEX (K) |
| 10 | FILTER WHEEL CYCLE COMPLETION INDEX (CYCLE) |
| 11 | SMOOTHING CONSTANT (ALPHA) |
| CTABL | |
| 12 (0,0) | STANDARDIZATION CORR. FACTOR, CTABLE=(C) |
| 13 (1,0) | |
| 14 (2,0) | |
| 15 (3,0) | |
| 16 (4,0) | |
| 17 (5,0) | |
| 18 (6,0) | |
| 19 (7,0) | SPARE |
| 20 (0,1) | |
| 21 (1,1) | |
| 22 (2,1) | |
| 23 (3,1) | |
| 24 (4,1) | |
| 25 (5,1) | |
| 26 (6,1) | |
| 27 (7,1) | SPARE |
| STTABL | |
| 28 (0,0) | STANDARDIZATION INPUT DATUM, ST=(R*) |
| 20 (1,0) | |
| 30 (2,0) | |
| 31 (3,0) | |
| 32 (4,0) | |
| 33 (5,0) | |
| 34 (6,0) | |

Table 7-continued

| Label and Relative Location of File | Description of Stored Data |
|---|---|
| 35 (7,0) | SPARE |
| 36 (0,1) | ,"=(T*) |
| 37 (1,1) | |
| 38 (2,1) | |
| 39 (3,1) | |
| 40 (4,1) | |
| 41 (5,1) | |
| 42 (6,1) | |
| 43 (7,1) | SPARE |
| RGTABL | |
| 44 (0,0) | NOMINAL BACKING REFLECT., RG =(Rg) |
| 45 (1,0) | |
| 46 (2,0) | |
| 47 (3,0) | |
| 48 (4,0) | |
| 49 (5,0) | |
| 50 (6,0) | |
| 51 (7,0) | SPARE |
| 52 (0,1) | NOMINAL DIFFUSER TRANS. "=(Td) |
| 53 (1,1) | |
| 54 (2,1) | |
| 55 (3,1) | |
| 56 (4,1) | |
| 57 (5,1) | |
| 58 (6,1) | |
| 59 (7,1) | SPARE |
| VTABL | |
| 60 (0,0) | CORRECTED & SMOOTHEED INPUT, NFCELL=R |
| 61 (1,0) | |
| 62 (2,0) | |
| 63 (3,0) | |
| 64 (4,0) | |
| 65 (5,0) | |
| 66 (6,0) | |
| 67 (7,0) | SPARE |
| 68 (0,1) | "=TDP |
| 69 (1,1) | |
| 70 (2,1) | |
| 71 (3,1) | |
| 72 (4,1) | |
| 72 (5,1) | |
| 74 (6,1) | |
| 75 (7,1) | SPARE |
| SGTABL | |
| 76 (0,0) | REFLECTANCE SPECIFIC GRADE CORR., SGCF |
| 77 (1,0) | |
| 78 (2,0) | |
| 79 (3,0) | |
| 80 (4,0) | |
| 81 (5,0) | |
| 82 (6,0) | |
| 83 (7,0) | SPARE |
| 84 (0,1) | TRANSMITTANCE SPECIFIC GRADE CORR. |
| 85 (1,1) | |
| 86 (2,1) | |
| 87 (3,1) | |
| 88 (4,1) | |
| 89 (5,1) | |
| 90 (6,1) | |
| 91 (7,1) | SPARE |
| OUTABL | |
| 92 (0) | PRINTING OPACITY (POPAC) Y REFL=ILLUM.A-. .89 BACKING (YAR89) |
| 94 (2) | TAPPI OPACITY (TOPAC) |
| 95 (3) | X-TRI.STIMULUS (XTRI) |
| 96 (4) | Y-TRISTIMULUS (YTRI) |
| 97 (5) | Z.TRISTIMULUS (ZTRI) |
| 98 (6) | HUNTER L (LH) |
| 99 (7) | HUNTER A (AH) |
| 100 (8) | HUNTER B (BH) |
| 101 (9) | BRIGHTNESS WITH FLUOR.&INF BACKING (BRRINE) |
| STABL | |
| 102 (0) | SCATTER COEFFICIENT (S) |
| 103 (1) | |
| 104 (2) | |
| 105 (3) | |
| 106 (4) | |
| 107 (5) | |
| 108 (6) | |
| 109 (7) | SPARE |
| KTABL | |

Table 7-continued

FILE X (Process File for the Data Acquisition and Data Reduction Programs

| Label and Relative Location of File | Description of Stored Data |
|---|---|
| 110 (0) | ABSORPTION COEFFICIENT (K) |
| 111 (2) | |
| 113 (3) | |
| 114 (4) | |
| 115 (5) | |
| 116 (6) | |
| 117 (7) | SPARE |
| RSTABL | |
| 118 (0,0) | STANDARDIZATION BACKING REFL REFERENCE (Rs) |
| 119 (1,0) | |
| 120 (2,0) | |
| 121 (3,0) | |
| 122 (4,0) | |
| 123 (5,0) | |
| 124 (6,0) | |
| 125 (7,0) | SPARE |
| 126 (0,1) | STANDARDIZATION DIFFUS. TRANS REFERENCE (Ts) |
| 127 (1,1) | |
| 128 (2,1) | |
| 129 (3,1) | |
| 130 (4,1) | |
| 131 (5,1) | |
| 132 (6,1) | |
| 133 (7,1) | SPARE |
| MPAR | |
| 134 (0) | FLUOR SLOPE EMPIRICAL CONSTANT |
| 135 (1) | $X_{lr}$-FLUOR/Z-FLUOR. RATIO FCON |
| 136 (2) | Br-FLUOR/Z-FLUOR RATIO FCON |
| 137 (3) | RESET VALUE OF FILTER CYCLE INDEX ICYCLE |
| 138 (4) | BASIS WT AVG.(FLOATING POINT) BW |
| 139 (5) | EMPIRICAL OVERALL REFL. CORR. FACTOR CORR |
| 140 (6) | EMPIRICAL OVERALL TRANS. CORR. FACTOR CORR |

In referring to locations of FILE X in the program flow charts of FIGS. 8–20, the relative location of FILE X is indicated by the number in parenthesis. Thus FILE X(4) refers to relative location number four of FILE X as given in Table 7. FILE X(138) corresponds to MPAR(4) in Table 7, and both refer to relative location number one hundred and thirty eight. File X(four) is an alternative to FILE X(4), and is used in the text to avoid any possible confusion with drawing reference numerals.

The following general discussion of successive locations or groups of locations of FILE X, taken in numerical order, will serve as an introduction of the description of the program routines of FIGS. 8–20. Contemplated modifications of the programs and of FILE X will be discussed in a later section.

In location O of FILE X, the Status word includes a bit number 23 which is set to a logical one when conditions are met for making standardizing calculations. For example, the OMOD should be off sheet and the data gauge with which the OMOD is mounted for scanning movement should be in its standardizing mode. The set condition of bit 23 is responded to by the program to bypass data smoothing and to store data in a special table STTABLE at locations 28–34 and 36–42 of Table 7. The condition of bit 23 is reset to logical zero when the filter wheel has indexed through seven positions or if the beta gauge completes standardization before the complete set of OMOD standardization data is collected.

Locations 1 and 2 of FILE X may store the PCW (process control word) addresses for Loops P and Q. Loop P is a subroutine for controlling the processing of reflectance data and Loop Q is concerned with the processing of transmittance data. These loops begin at FIG. 13 of Program Fourteen.

Location three of FILE X, contains the address of the DDC scanner file containing the position of the sensing head 10 along its path of traverse of the web. This position is monitored by the Scan-Only (DDC) routine of FIG. 7 and is stored in the scan system file identified by TAG one hundred twenty nine. A current value of sensing head position is transferred from the referenced DDC file into location three of FILE X periodically.

Location four of FILE X stores a SLOWDOWN COUNT index value which is used to cause a specified number of dummy readings at each filter wheel position to be made after each advance of the filter wheel to allow time for the OMOD electronics to reach steady state, and to allow for any transient error in synchronization between the DDC Scan-Only routine of FIG. 7 and the Data Reduction routine (Program Fourteen) of FIGS. 8–16 which runs at one second intervals under the control of the RTMOS Scheduler (a computer real time operating system of the General Electric Co.).

Location five of FILE X stores a SLOWDOWN INITIAL VALUE COUNT which is used when a processing cycle is being initiated.

Location six of FILE X of Table 7 stores an index value I which represents the estimated filter wheel position, based on the number of actuations of the filter wheel indexing solenoid, since the initial filter wheel position wherein reed switch 358, FIG. 6, is closed in response to the proximity of permanent magnet 243, FIGS. 3 and 6. In the computer program, the successive filter wheel positions are designated O, 1, 2, 3, 4, 5 and 6, and result in spectral response distributions designated $B_R$ (brightness), $X_B$ (blue portion of the $E_c\bar{x}$ function), $X_R$ (red portion of the $E_c\bar{x}$ function), Z ($E_c\bar{z}$ function without fluorescence), $Y_C$ ($E_c\bar{y}$ function), $Y_A$($E_a\bar{y}$ function), and $Z_{FL}$($E_c\bar{z}$ function, with fluorescence).

Location seven of FILE X serves to store the address of the DDC file for basis weight average. TAG BOO, which is used by Program Fourteen to access the basis weight data and store it in location MPAR (4) in floating point format. This will be used by Program Forty-Two during the reduction of data.

Location eight of FILE X stores a value for the minimum on-sheet head position. When the head position is less than such minimum value, a standardization cycle may be set in motion by Program Fourteen.

Location nine of FILE X contains the value of an initialization index K which is used to determine when all seven smoothed input values have been initialized to equal the latest unsmoothed input for each of the reflectance and transmittance channels.

Location ten of FILE X stores a filter wheel cycle completion index designated CYCLE that can be used to determine when a specified number of filter wheel cycles have been completed through the last filter wheel position (position six in the programming notation). This prevents the data reduction program (Program Forty-Two) of FIGS. 17–20 from running until a specified number of data sets have been collected since the last time it ran or the unit was standardized.

Figure 14:
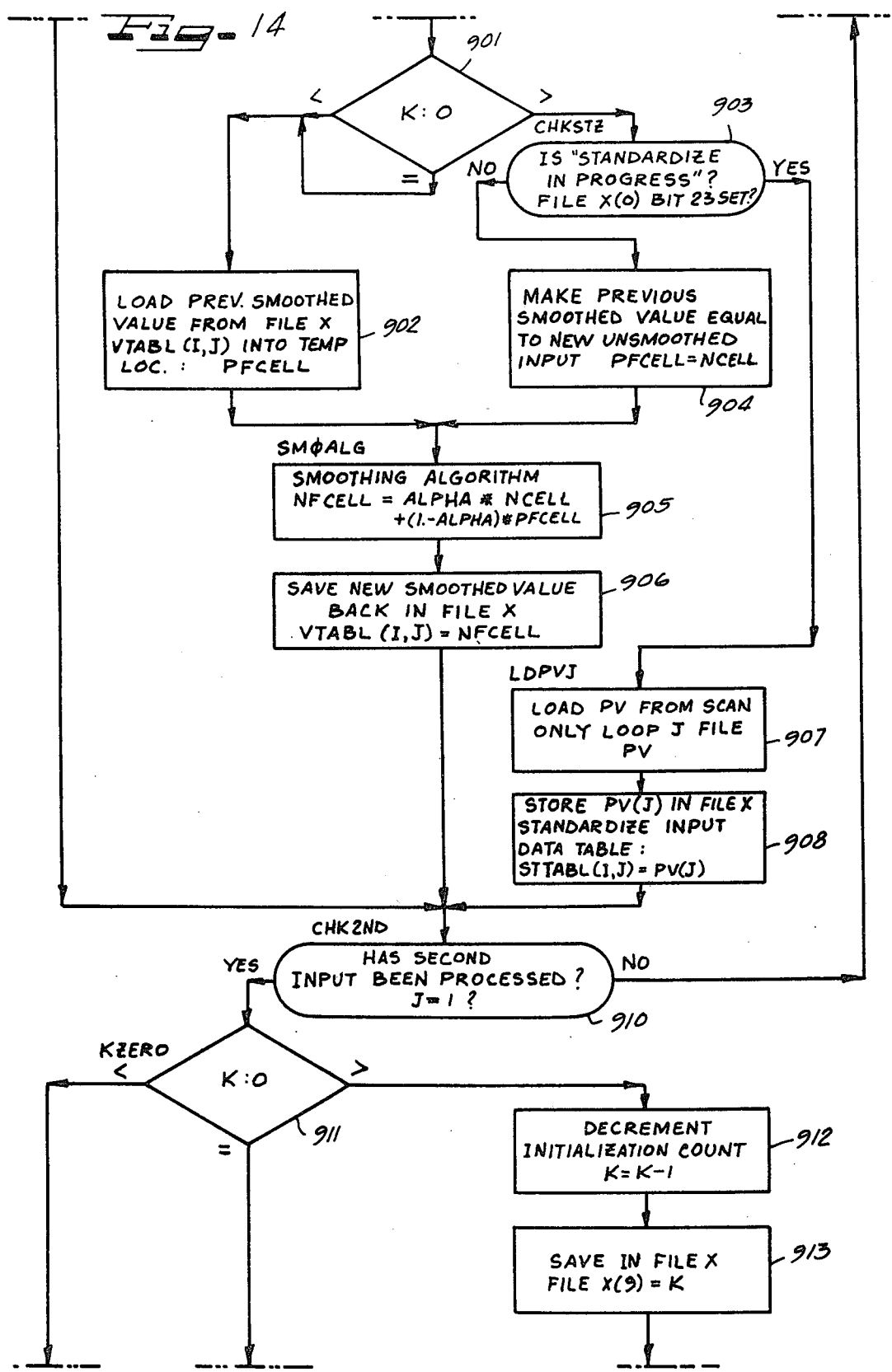

Location eleven of FILE X stores a smoothing constant ALPHA which is used in smoothing the input data from FIGS. 1–6 by Program Fourteen, as indicated in FIG. 14.

A temporary location index J is used to point to either the reflectance vector tables or the transmittance vector tables. J is equal to zero to indicate reflectance, and is equal to one to designate transmittance. Each of the tables such as CTABL of table 7 has a first set of loctions (e.g. 12 through 18) which can become active while J is equal to zero and a second set of locations (e.g. 20 through 26) which can be selected when J is equal to one. Thus the sets of two numerals in parenthesis at locations 12 through 133 represent respectively the value of the filter wheel position index I and the J index value corresponding to the location.

The table CTABL at locations 12–18 and 20–26 of the process file of Table 7 is used to store a standardization correction factor C. The reflection values of the factor C for the respective filter wheel positions are stored in locations 12–18 and are active when J=0, and I=0, 1, 2, 3, 4, 5 and 6, respectively. Similarly the transmission values for the lower sensing head and the respective filter wheel positions are stored in locations 20–26, which are selected when J=1 and I=0, 1, 2, 3, 4, 5 and 6, respectively.

The table STTABL, stores data from the OMOD system of FIGS. 1–6 in the standardization mode with the heads in the off-sheet position.

The table RG TABL stores the value RG, the nominal reflectance of the backing for the web in the off-sheet position, for the respective filter wheel positions, and also the value TD, the nominal transmittance of the diffusing window 135 in the off-sheet position. These values may be experimentally determined as previously explained and inserted into table RG TABL at start up of the system.

Table VTABL serves to store input data after it has been processed by Program Fourteen of FIGS. 8–16. The raw data is corrected on the basis of the most recent standardization values from table ST TABL and, multiplied by the correction factors C from table CTABL, and exponentially smoothed by means of the subroutine of FIG. 14 before being stored in the VTABL locations.

The SG TABL table of the process file of Table 7 stores the specific grade correction factors SGCF.

The OUTABL locations store the output quantities as computed under the control of the Data Reduction Program Forty Two of FIGS. 17–20.

The tables STABL and KTABL store the scatter coefficient S and the absorption coefficient K which together serve to characterize the paper web being monitored.

OPTICAL PROPERTY DATA ACQUISITION SUBROUTINE OF FIGS. 8-16 (PROGRAM FOURTEEN)

The subroutine of FIGS. 8–16 is referred to as Program Fourteen (or Program 14) and is designed to perform various data acquisition functions as indicated in the flow chart.

It is believed that the flow chart of FIGS. 8–16 will be self-explanatory given the foregoing comments concerning Table 7. The following Tables 8–16 are a tabulation of the blocks of the subroutine with supplementary comments to indicate the meaning of any abbreviations, or to paraphrase any possibly cryptic statements. (Arabic numerals within the blocks in FIGS. 8–20 do not refer to reference numerals of FIGS. 1–6. This is indicated in the following tabulation spelling of such numerals so far as feasible).

Table 8

Supplementary Explanation of the Program Steps of FIG. 8

| Program Step | Comment |
|---|---|
| 801 | Program Fourteen initial point at start up. |
| 802 | The timer location designated AUXTM +3 receives an initial value. (Equal to the present time). |
| 803 | The point of entry each time the timer location AUX-TIME reaches a value L, i.e. every one second. |
| 804 | Load the starting address of File X into index register three. |
| 805 | Load PCW (process control word) addresses of loops P and Q from locations one and two of FILE X. (See Table 7.) |
| 806 | Are scan bits in both of the process control words referred to in block 805 set for off-scan? |
| 807 | If decision at block 806 is no, calculate the next time for Program Fourteen to run DLYTIM (delay time) seconds from the present time. (The value of DLYTIM is nominally one second). Add DLYTIM to the present value of AUXTM+3 to register a new time AUXTM+3. |
| 808 | Load value of SLOWDOWN COUNT from location four of FILE X into the temporary register SLODWN. |
| 809 | Decrement the count in SLODWN by one. |
| 810 | If answer to decision of block 806 is yes, turn Program Fourteen off and exit from the program. |

Table 9

Figure 9:
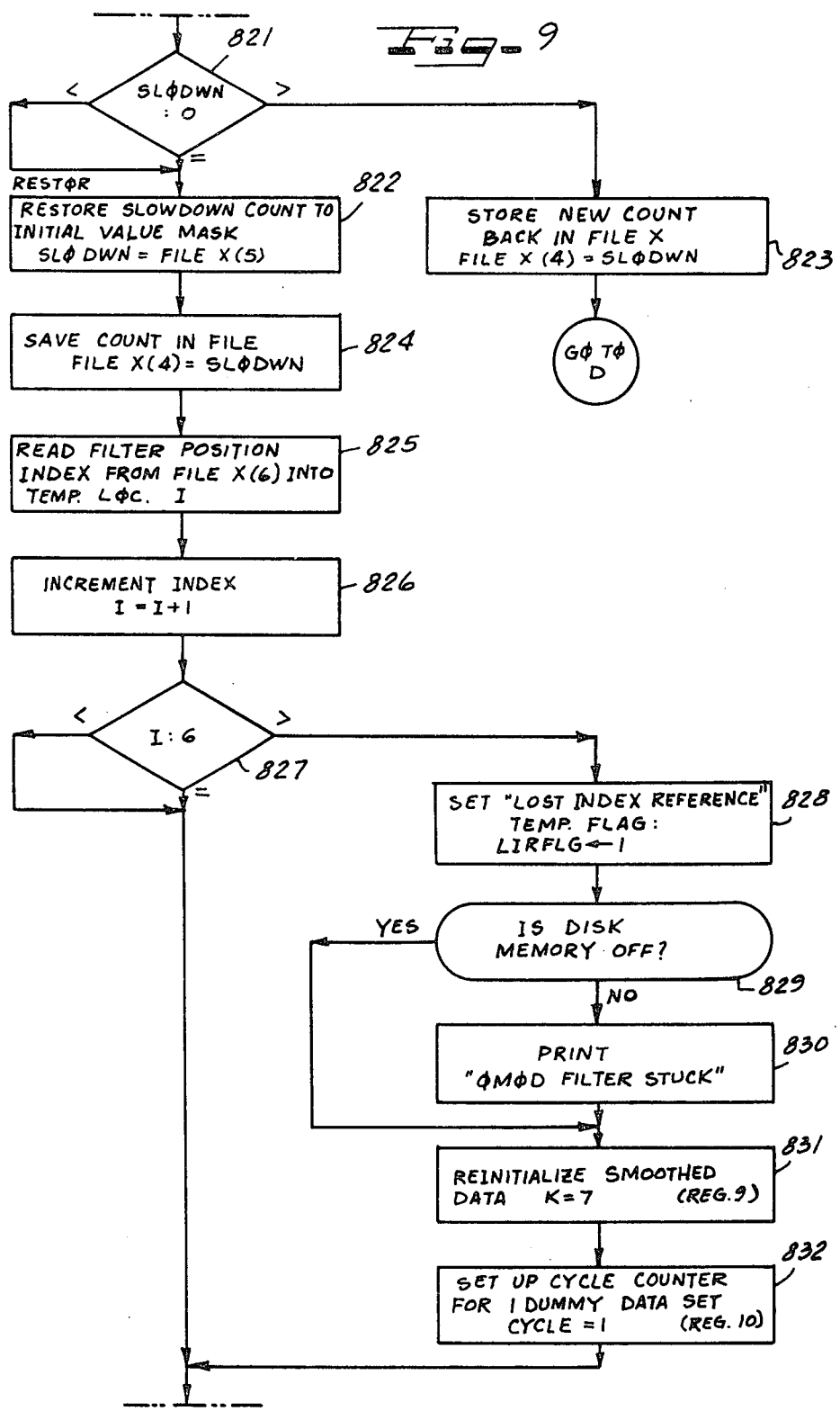

Supplementary Explanation of the Program Steps of FIG. 9

| Program Step | Comment |
|---|---|
| 821 | Compare the count value in SLODWN with zero, If SLODWN is equal to or less than xero, go to block 822. If SLODWN is greater than zero, go to block 823. |
| 822 | Insert SLOW DOWN INITIAL VALUE COUNT from FILE X(five) into the SLODWN register. |
| 823 | Store the decremented count value in SLODWN in SLOW DOWN COUNT at FILE X(four), and go to point D of the program, shown in FIG. 16. |
| 824 | Place the count transferred from FILE X(five) at block 822 into FILE X(four) labeled SLOW DOWN COUNT. |
| 825 | Read content of FILE X(six) into temporary location I. |
| 826 | Add one to temporary location I. |
| 827 | Compare I and six; if I equal to or less than six, go to LDDIDG, block 841 of FIG. 10; if I is greater than six, go to block 828. |
| 828 | Put a one in temporary flag location LIRFLG. |
| 829,830 | If disk memory is operating print out that the indicated message. |
| 831 | Set the K value in location nine of FILE X to seven. |
| 832 | Set CYCLE value in location ten of FILE X to one, and go to LDDIDG, block 841, FIG. 10. |

Table 10

Figure 10:
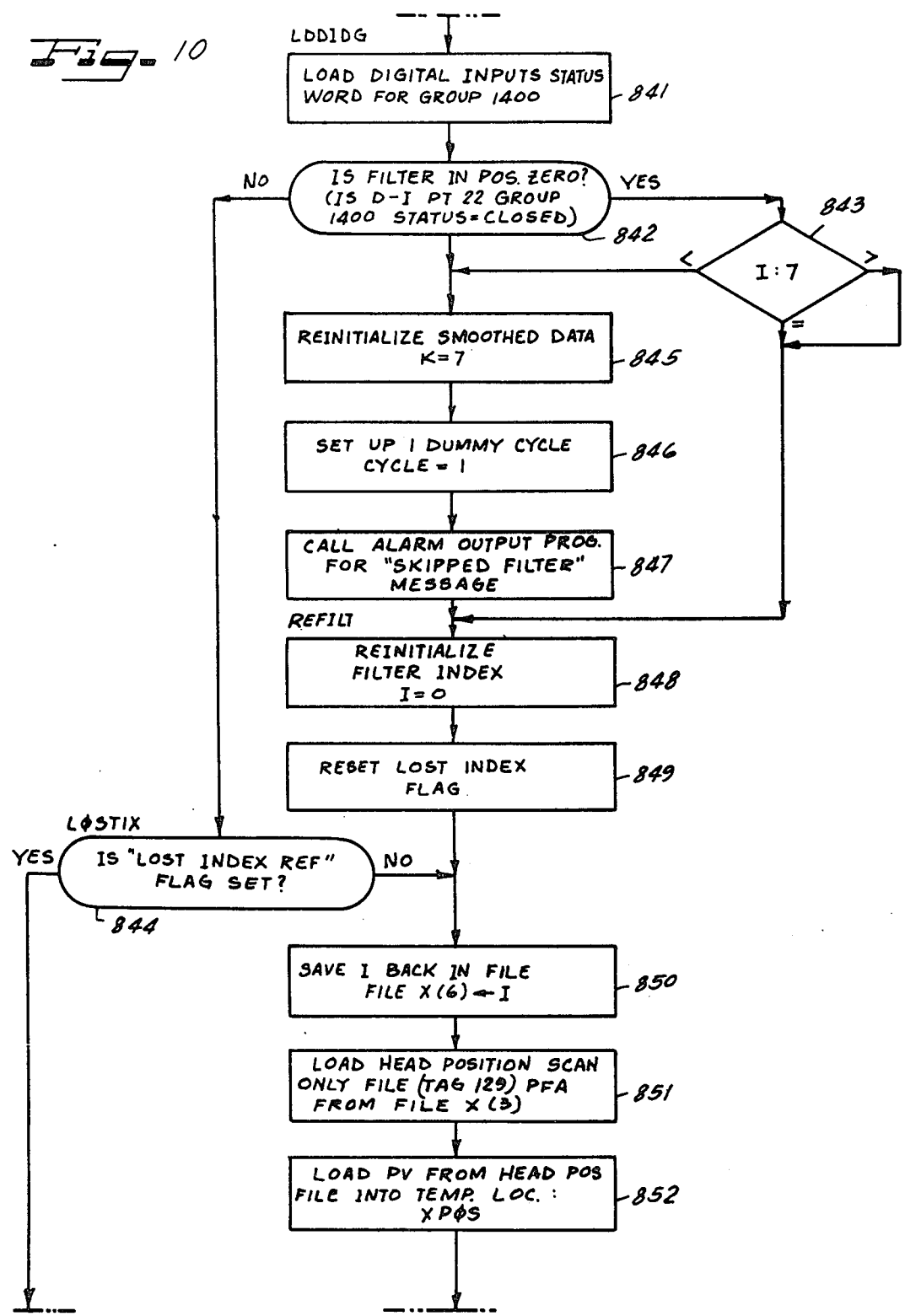

Supplementary Explanation of the Program Steps of FIG. 10

| Program Step | Comment |
|---|---|
| 841 | Load the contents of the memory location that indentifies the status of the digital input group (Group 1400) to which the zero position filter contacts 358, FIG. 6, are connected. |
| 842 | Is the filter wheel in position zero, i.e. the position shown in FIG. 3 This is determined from bit position twenty-two of the STATUS word loaded in step 841. If bit position twenty-two indicates that the contacts of reed switch 358, FIG. 6, are closed, then go to block 843. If the contacts are open, go to LOSTIX, block 844. |
| 843 | If value in temporary location I is less than seven, go to block 845. If I is equal to or greater than seven go to REFILT, block 848. |
| 844 | Is a value one in the temporary flag location LIRFLG?(See block 828, FIG. 9.) |
| 845 | Set FILE X (nine) to seven. |
| 846 | Set FILE X (ten) to one. |
| 847 | If the filter wheel is indexing properly, the I value will be incremented by the step of block 826, FIG. 9, so that I will equal seven at block 843. Since I was less than seven, apparently the filter wheel has failed to index each time it was commanded to do so. Block 847 provides for the print out by means of an alarm output program under these conditions. |
| 848 | Set location six of FILE X to zero. |
| 849 | Set LIRFLG to zero. |
| 850 | Insert current value of I in FILE X (six). |
| 851 | Load the head traverse position File Address from FILE X(three). |
| 852 | Load the process variable (PV) of block 851 into the temporary location XPOS. |

Table 11

Figure 11:
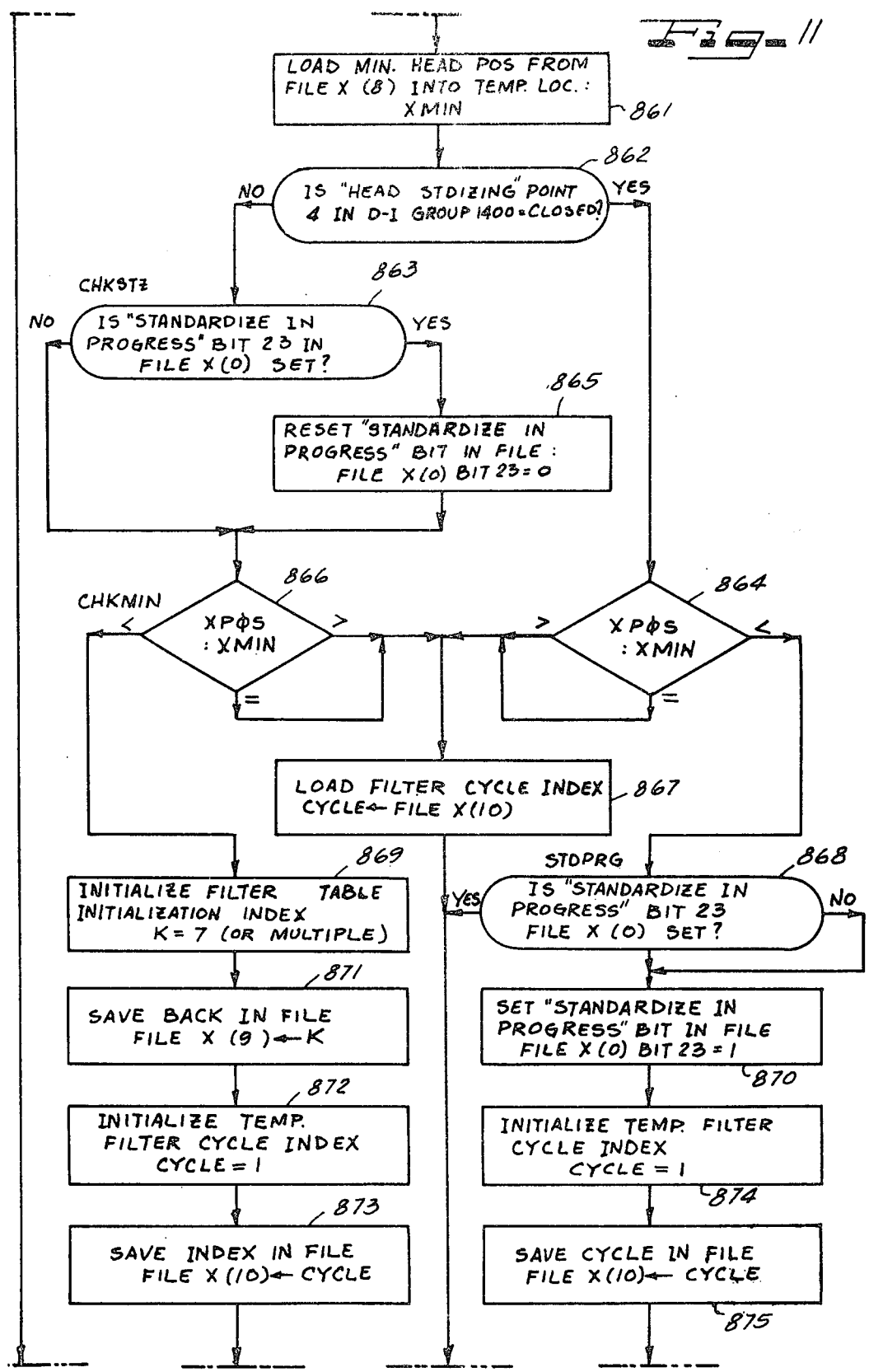

Supplementary Explanation of the Program Steps of FIG. 11

| Program Step | Comment |
|---|---|
| 861 | Load the content of FILE X(eight) into the temporary location XMIN. |
| 862 | Is the beta gauge in a standardizing mode as indicated by point four in the digital input status word for group fourteen hundred?Point four refers to the bit four position of the status word. If the beta gauge is not in standardizing mode, go to CHKSTZ at block 863. If beta gauge is in standardizing mode, go to block 864. |
| 863 | Is the OMOD shown to be in standardizing mode by bit position twenty three of FILE X (zero). If the OMOD is being standardized, go to block 865. If standardization is not in progress go to block 866. |
| 864 | Compare the value of XPOS(See block 852 FIG. 10) with the value of XMIN (See block 861). If XPOS is equal to or greater than XMIN, go to block 867. If XPOS is less than XMIN, go to block 868. |
| 865 | Reset bit position twenty three of FILE X(zero) to zero. |
| 866 | Compare XPOS and XMIN. |
| 867 | Load content of FILE X(ten) into the temporary register CYCLE. |
| 868 | Is bit position twenty three of FILE X(zero set?If yes, go to comparison block 881, FIG. 12, If not, proceed with standardization beginning at block 870. |
| 869 | Set temporary register K to seven or a multiple of seven. |
| 870 | Set bit position twenty three of FILE X(zero) to the logical one state. |
| 871 | Put the value of K (see block 869) into FILE X(nine). |
| 872 | Set temporary register CYCLE to logical one state. |
| 873 | Place content of CYCLE in FILE X (ten). |
| 874 | Same as block 872. |
| 875 | Same as block 873. |

Table 12

Figure 12:
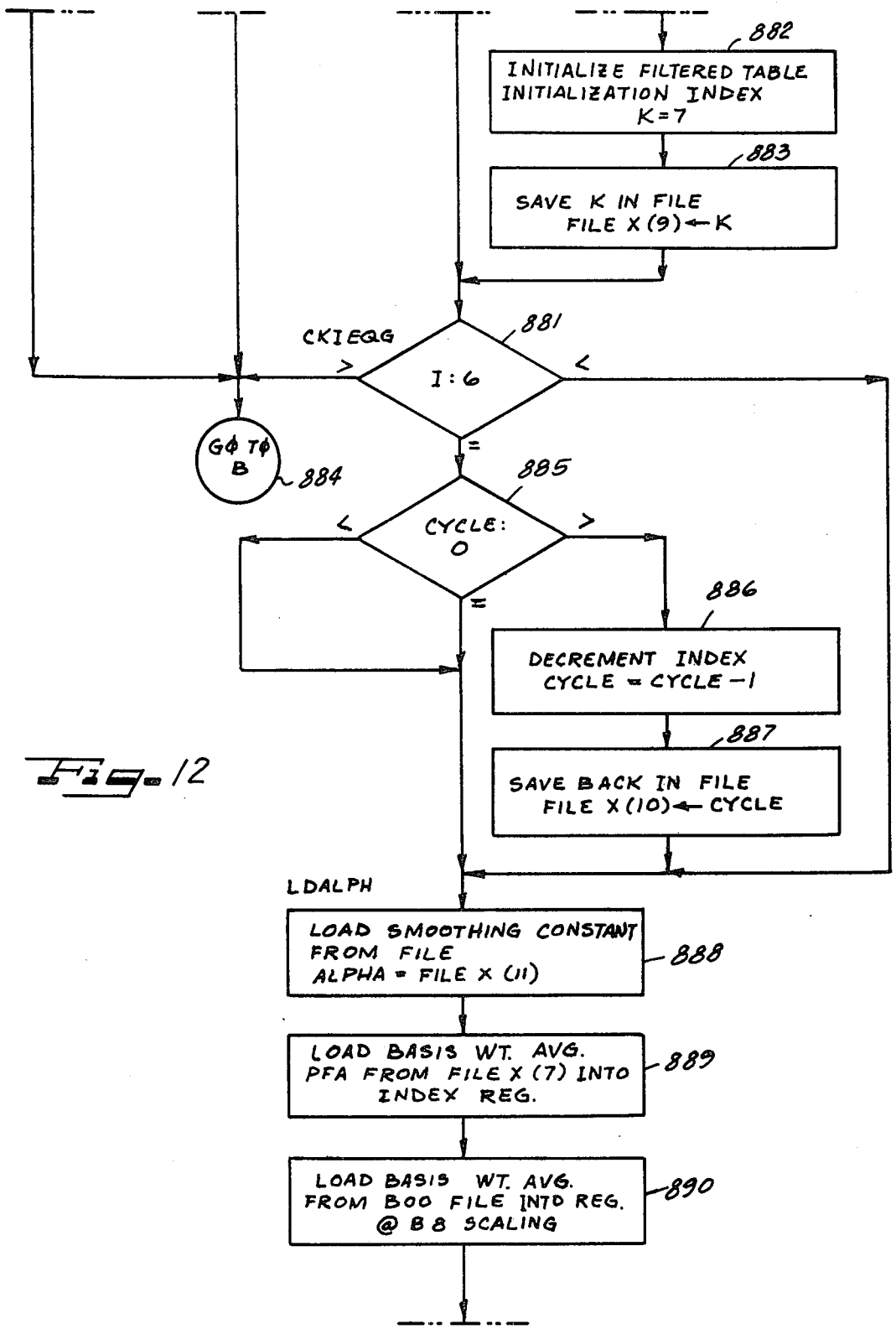

Supplementary Explanation of the Program Steps of FIG. 12

| Program Step | Comment |
|---|---|
| 881 | Compare value in temporary register I with six. |
| 882 | Continuation from block 875, FIG. 11. Same comment as for block 869. |
| 883 | Same as block 871. |
| 884 | Go to BENTER location, FIG. 16, after an affirmative decision at block 844, FIG. 10; or after execution of step 873, FIG. 11; or if I is greater than six at block 881. |
| 885 | Compare CYCLE and zero. |
| 886 | Decrement CYCLE by one if CYCLE was greater than one at block 885. |
| 887 | Same as 873. |
| 888 | Load content of FILE X(eleven) into temporary register ALPHA. |
| 889 | Load content of FILE X(seven) into the index register (BOO File Address) |
| 890 | Load BOO process variable into A-register with fixed point scaling of B8. |

Table 13

Figure 13:
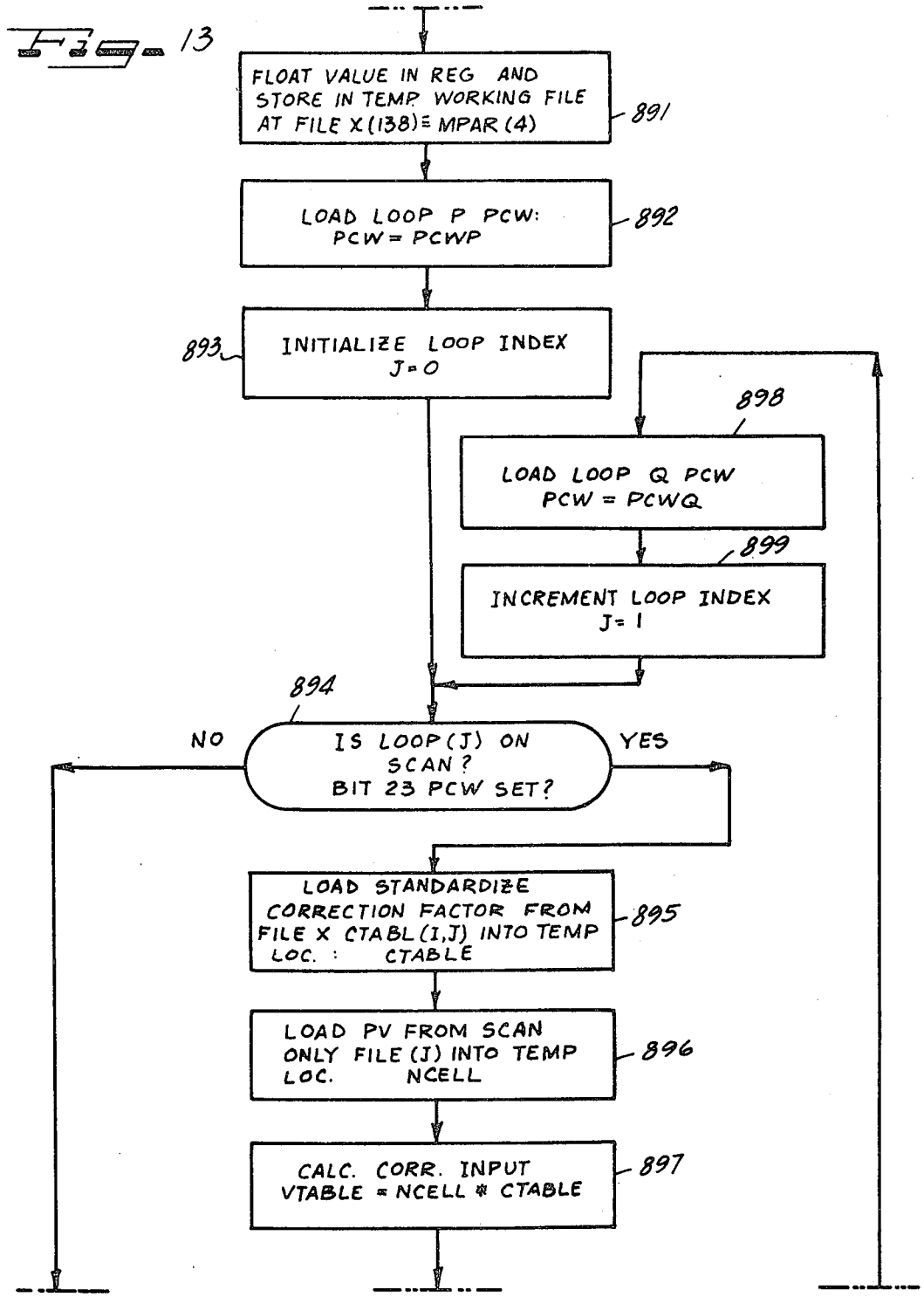

Supplementary Explanation of the Program Steps of FIG. 13

| Program Step | Comment |
|---|---|
| 891. | convert content at B8 SCALING (See block 890, FIG. 12) to floating point notation and store converted value in FILE X(one hundred thirty eight), which is also designated MPAR, location four in Table 7. |
| 892 | Load the process control word PCWP at the address given at FILE X(one) into the register PCW. |
| 893 | Set regiter J to zero. |
| 894 | Is bit position twenty three of the process control word (PCW) of LOOP(J) set?If not, go to block 910, FIG. 14. If yes, go to block 895. |
| 895 | Load the content of CTABL of FILE X for the location corresponding to the current values of I and J into temporary location CTABLE. |
| 896 | Load the process variable (PV) from the Scan Only File PF(J) into the temporary location NCELL. |
| 897 | Calculate the corrected input value by multiplying the content of NCELL by the content of CTABLE, and store in the table VTABLE of FILE X(See Table 14) in the location corresponding to current values of I and J. Go to block 901, FIG. 14. |
| 898 | After a negative decision at block 910, FIG. 14, the loop P subroutine is initiated by loading the process control word PCWQ whose address is given at FILE X(two) into the temporary register PCW. |

Table 13-continued

Supplementary Explanation of the Program Steps of FIG. 13

| Program Step | Comment |
|---|---|
| 899 | Increment the value stored in location J to one. |

Table 14

Supplementary Explanation of the Program Steps of FIG. 14

| Program Step | Comment |
|---|---|
| 901 | Compare the value in temporary location K with zero. If K is equal to or less than zero, go to block 902. If K is greater than zero, go to CHKSTZ, block 903. |
| 902 | Load content of current location of VTABL (I,J) from FILE X into the temporary location PFCELL. |
| 903 | Is bit twenty three of the status word in FILE X (zero) set |
| 904 | Transfer content of NCELL (see block 896, FIG. 13) into the temporary loction PFCELL. |
| 905 | Apply the smoothing algorithm by calculating the sum of ALPHA times NCELL and (one minus ALPHA) times PFCELL, and store the result in NFCELL. |
| 906 | Transfer the content of NFCELL to the appropriate location of VTABL (I,J) in FILE X, (See Table 7.) |
| 907 | Load the PV from Scan Only LOOP J, i.e. Process FILE PF (J) into temporary register PV (J). |
| 908 | Store the content of PV (J) in table STTABL (I,J) of FILE X at a location corresponding to the current values of I and J. See Table 7. |
| 910 | Has loop Q been processed?If not, enter loop Q at block 898, FIG. 13. If the content of temporary location J is equal to one, go to block 911. |
| 911 | Compare the content of temporary location K with zero. If K is less than zero, go to the B entry location BENTER, FIG. 16. If K equals zero, go to block 921, FIG. 15. If K is greater than zero, go to block 912. |
| 912 | Decrement the count in K by one |
| 913 | Store the content of K in FILE X(nine). Go to BENTER location in FIG. 16. |

Table 15

Figure 15:
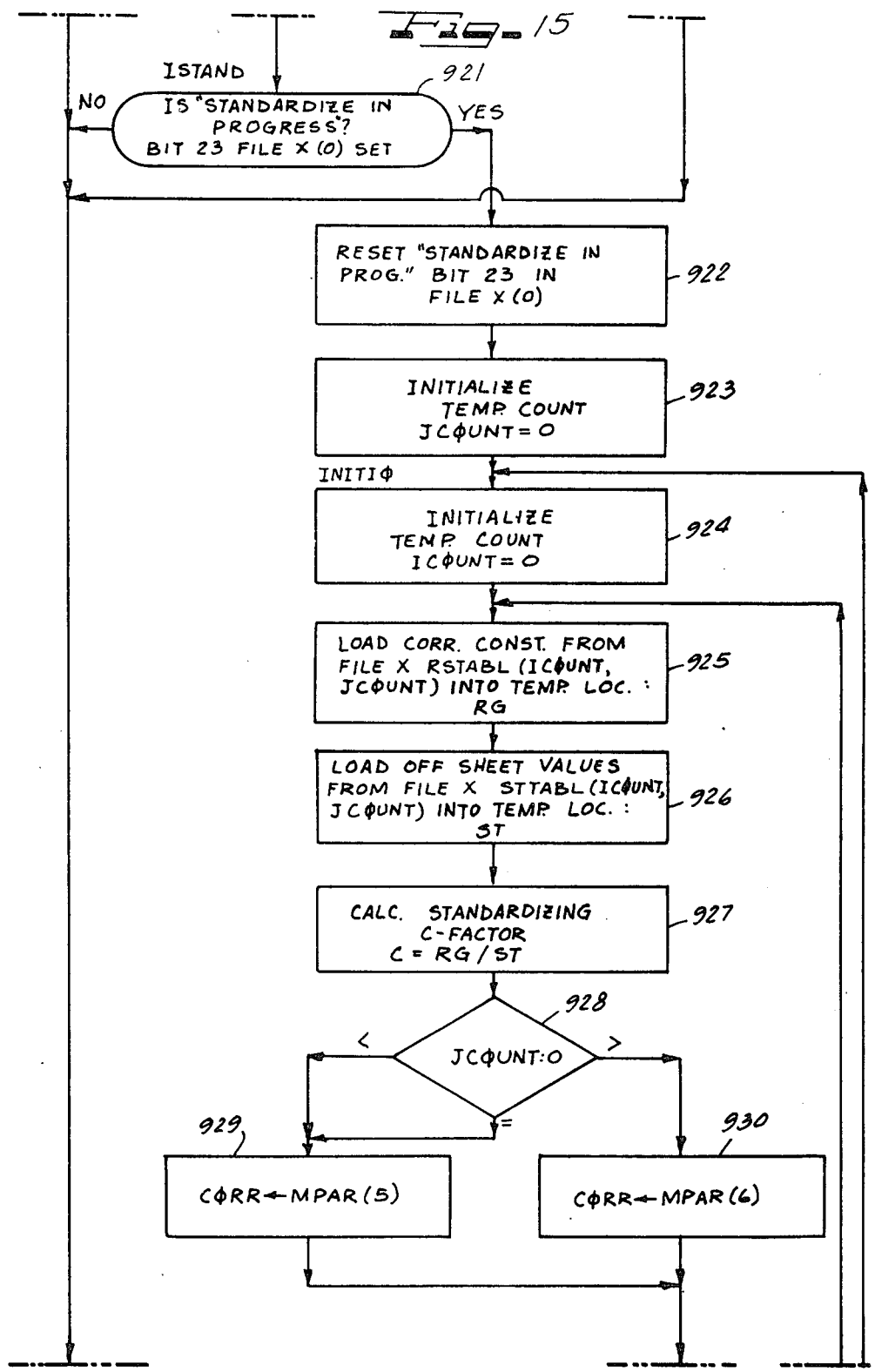

Supplementary Explanation of the Program Steps of FIG. 15

Figure 16:
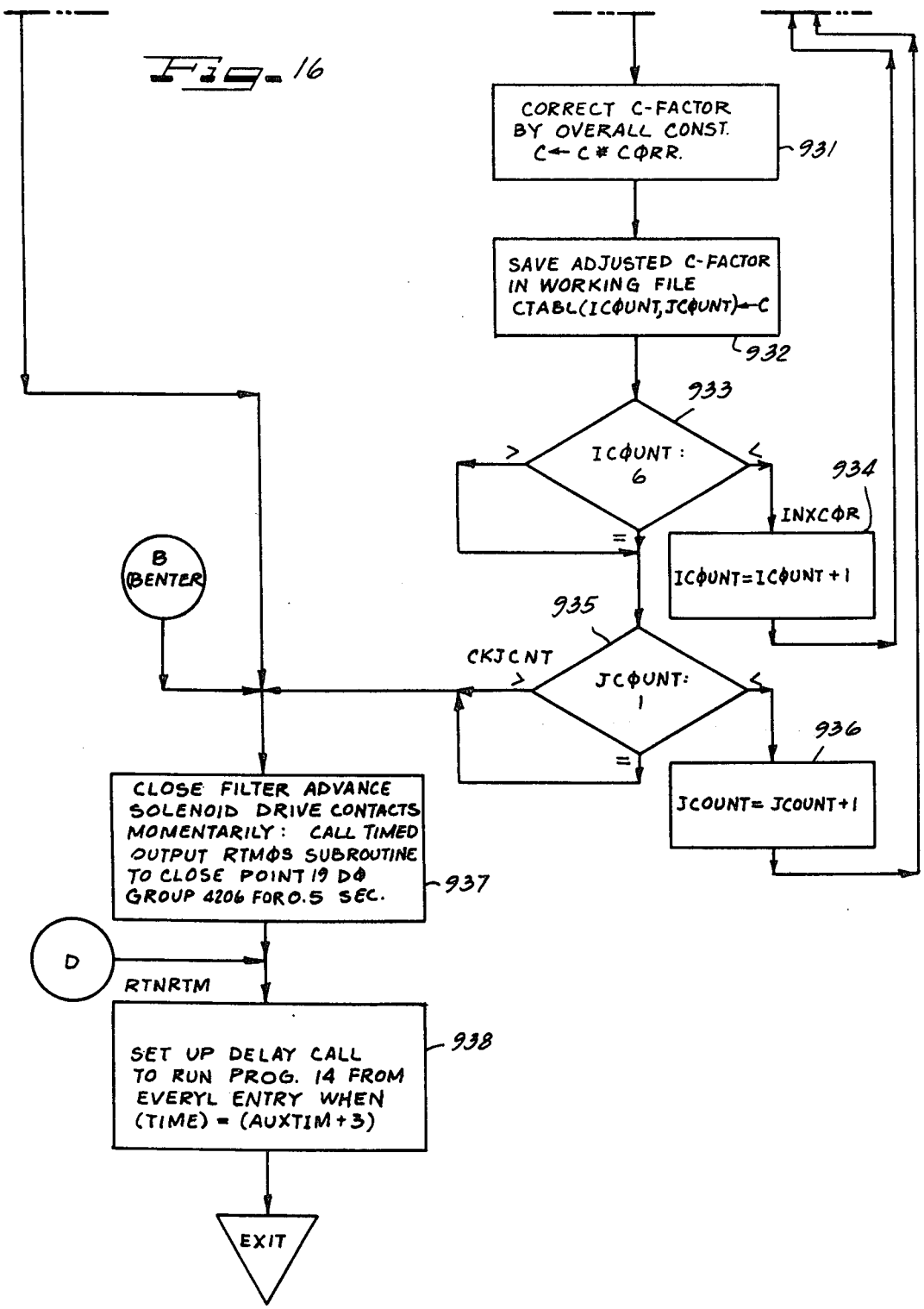

| Program Step | Comment |
|---|---|
| 921 | Is bit position twenty three of the STATUS word from FILE X(zero) set If not, go to BENTER location of FIG. 16. If affirmative, go to block 922. |
| 922 | Reset bit position twenty three of FILE X(zero). |
| 923 | Set temporary register J COUNT to zero. |
| 924 | Set temporary register I COUNT to zero. |
| 925 | Load the correction constant from the appropriate location of RSTABL, Table 7, into the temporary location RG. |
| 926 | Load the standardization value from the appropriate location of STTABL, Table 7, into the temporary location ST. |
| 927 | Calculate the standardizing C factor by dividing RG by ST and store in temporary location C. |
| 928 | If J COUNT is less than or equal to zero, go to block 929; otherwise go to block 930. |
| 929 | Transfer the value stored at FILE X (one hundred thirty nine) to temporary location CORR. |
| 930 | Transfer the value stored at FILE X (one hundred forty) to temporary location CORR. |

Table 16

Supplementary Explanation of the Program Steps of FIG. 16

| Program Step | Comment |
|---|---|
| 931 | Multiply the value in temporary location C (see block 927) by the value in CORR and store the adjusted C factor in C. |
| 932 | Store value in C in FILE X at CTABL at current values of I COUNT and J COUNT. |
| 933 | Compare I COUNT to six. If I COUNT is less than six, go to block 934. |
| 934 | Increment I COUNT by one and reenter at block 925, FIG. 15. |
| 935 | Compare J COUNT and one. If less than one, go to block 936. |
| 936 | Increment J COUNT by one and reenter at block 924, FIG. 15. |
| 937 | The computer output contact at point nineteen of digital output (DO)Group forty two hundred and six (not shown) is closed by the computer in response to this program step to energize solenoid 240, FIGS. 3 and 6, from the plus 24 volt supply and conductors 505 and 506. |
| 938 | Program Fourteen reschedules itself to run again in aproximately one second. |

COMMENTS REGARDING PROGRAM FOURTEEN

1. The values stored under RSTABL (118–133) will be identical to the values stored under RGTABL (44–59) and, therefore, the former table will be eliminated when the necessary program changes are also made. The RK and TK correction factor approach allows this simplification of the calculations.

2. Program Fourteen can be further revised to eliminate the need for the nominal diffusor transmittance, $T_d$, completely. Manipulation of the terms of the equations involved permits this elimination. Note referring to Table 4, S.0023, that TPDOTD, the ratio of TPD/TD, is equal to (TSP* TK)/TSD, eliminating the need to know the absolute value of TD. TD is the computer symbol representing $T_d$, the transmittance of the diffuser. Refer also to the paragraph following Table 2.

3. Program Fourteen also calls for the re-initialization of the algorithm which smooths the "raw" reflectance and transmittance after each standardization. It is presently considered that this re-initialization will not only be unnecessary, but would add to control problems. Consequently, this will likely be changed so that this smoothing goes on indefinitely after a run start-up. (Note: Do not confuse the smoothing of the "raw" data from the paper with the correction factors acquired during standardization--The latter will not and likely should not be smoothed at all.)

4. Program Fourteen has not as yet been debugged. Debugging can only be accomplished after connecting the computer to the system of FIGS. 1–6 via an A to D converter. It is considered that such debugging is a routine matter well within the skill of the art. It may be noted that the OMOD is now on line as shown in FIGS. 1–6 and data collection has begun.

SUMMARY OF OPERATION OF PROGRAM FOURTEEN

Program Fourteen is designed to perform various functions described as follows:

1. Sequentially read the reflectance and transmittance values stored in the Process File until both values for each of the seven OMOD filter positions are obtained.

It takes about two seconds from the time the filter wheel is advanced until the photocell readings reach a near equilibrium condition. Program Fourteen is, however, linked timewise to the DDC scan program and is programmed to run every second also. Consequently, any data acquired before the photocells reach a near equilibrium condition, will be liable to intolerable error. Program Fourteen solves this problem by processing data on a multisecond interval basis only, e.g., every 2, 3, 4, etc., seconds depending upon the choice of the value of the term SLOWDOWN which inserted in File X(five).

2. Check the OMOD to see if it is operating properly and issue alarms if it is not. "OMOD Filter Stuck" and "Skipped Filter" alarm messages were made available.

The upper OMOD head is designed with an extra reed switch 358, FIG. 6, which closes when the brightness filter is in the optical train pathway. (Previous description herein refers to the brightness filter as the first position; however, Program Fourteen refers to it as the zero position.) The computer program checks the status of this switch as being open or closed by means of Point 22-Group1400. The filter index is initialized back to zero each time the status of Point 22-Group 1400 is closed. Discrepancies, should they occur between the expected filter index based on the incremented count and the actual filter position can be readily recognized by this program. This serves as the basis for the alarms previously mentioned.

3. Determine when and how often the optical property Data Reduction Program, No. Forty Two, (see FIGS. 17–20) is to be run. This is controlled by the value chosen for the term "Cycle."

4. Read the OMOD head position and the average basis weight of the paper being produced and store for use in subsequent calculations or program logic tests. This information is readily available from a basis weight control program which has been in use for several years.

5. Correct the "raw" reflectance and transmittance data by multiplying each of the fourteen values by the appropriate correction factor. The values of these correction factors are updated by the last standardization sequence which occurred prior to their actual use (see 7 below).

6. Exponentially smooth each of the corrected reflectance and transmittance values and store for subsequent calculations.

Exponential smoothing requires a previous value to act upon; however, such previous value is not available for run startup, etc. An initialization technique involving an initialization index, $k$, is employed to solve this problem. The degree of smoothing is determined by the value chosen for $\alpha$ (ALPHA).

7. Initialize and control the automatic standardization of the OMOD.

The OMOD heads are mounted next to an Electronic Automation Inc. (EA) basis weight gauge in a piggyback fashion. This EA system utilizes an O frame to permit scanning the full web width. It is also designed to automatically retract the carriage 25, 26, FIG. 2, of the scanning Mechanism upon which the basis weight gauge and OMOD are mounted, to an offsheet position (FIG. 2) at 1-hour intervals. Program Fourteen takes advantage of this schedule to standardize the OMOD at the same time that the basis weight gauge is being standardized. When offsheet, the very durable Lucalux backing 135, FIG. 3, is always in position to permit checks of its reflectance and transmittance. Due to its durability and inertness, the latter should remain unchanged for long periods of time. In addition, the moving web will insure its cleanliness prior to each standardization occurrence. Consequently, this standardization procedure will allow for accurate updating of the correction factors for each filter position. In so doing, it compensates for any changes which may inadvertently occur in the light source, filters, photocells, lenses, electronic amplification, etc.

Two overall geometrical correction factors are also employed at this point of the program to adjust for any relative head spacing or alignment change that may also inadvertently occur. Experimental data has shown that the same geometrical correction can be used for each reflectance measurement. The values of these two factors are, however, not determined automatically, but must be determined by external means involving offline audit testing by comparing OMOD readings with those of off-line standard laboratory instruments before being fed into the proper computer storage. Initial values of these two factors will be unity; in which case, the relative head geometry will be assumed to be in standard condition and no geometrical correction factor required.

The alternative to using these geometrical correction factors is to realign and/or respace the heads when needed. In the case of minor adjustments, the former approach is clearly the more desirable where the heads are in an inaccessible location and functioning on a high-speed paper machine with little downtime available for such mechanical readjustments.

Program fourteen as presently devised, does not call for the exponential smoothing of the correction factors updated upon each standardization. This could be easily changed should on-line experience indicate that such smoothing is desirable.

8. Control the advance of the OMOD filter wheel 210, FIG. 4, to the next filter position at the desired time interval. This is accomplished by the computer 996, FIG. 6, directing the closure of a loop 505, 506, FIG. 6, which energizes the solenoid. The energized solenoid lifts the rachet arm 230, FIG. 3, clear of the lug against which it was previously braced. The filter wheel shaft is under a continuous torque, tending to rotate it at all times. Thus, it begins to rotate when freed of the holding ratchet arm; but it is stopped again at the next lug, since by then the solenoid attached to the ratchet arm is once again de-energized by computer command. The low torque motor 209, FIG. 6, designed to be stalled indefinitely without harm provides the necessary filter wheel torque.

9. Program fourteen reschedules itself to run again in approximately 1 second.

OPTICAL PROPERTY DATA REDUCTION SUBROUTINE OF FIGS. 17–20 (PROGRAM FORTY TWO)

The purpose of this program is to reduce the corrected reflectance and transmittance data into terms with which papermakers are familiar and upon which paper optical specifications are based; e.g., brightness, opacity, color and fluorescence. A description of this program follows.

The following Tables will serve to supplement the labels applied to the blocks of the flow chart illustrating this program.

Table 17

Figure 17:
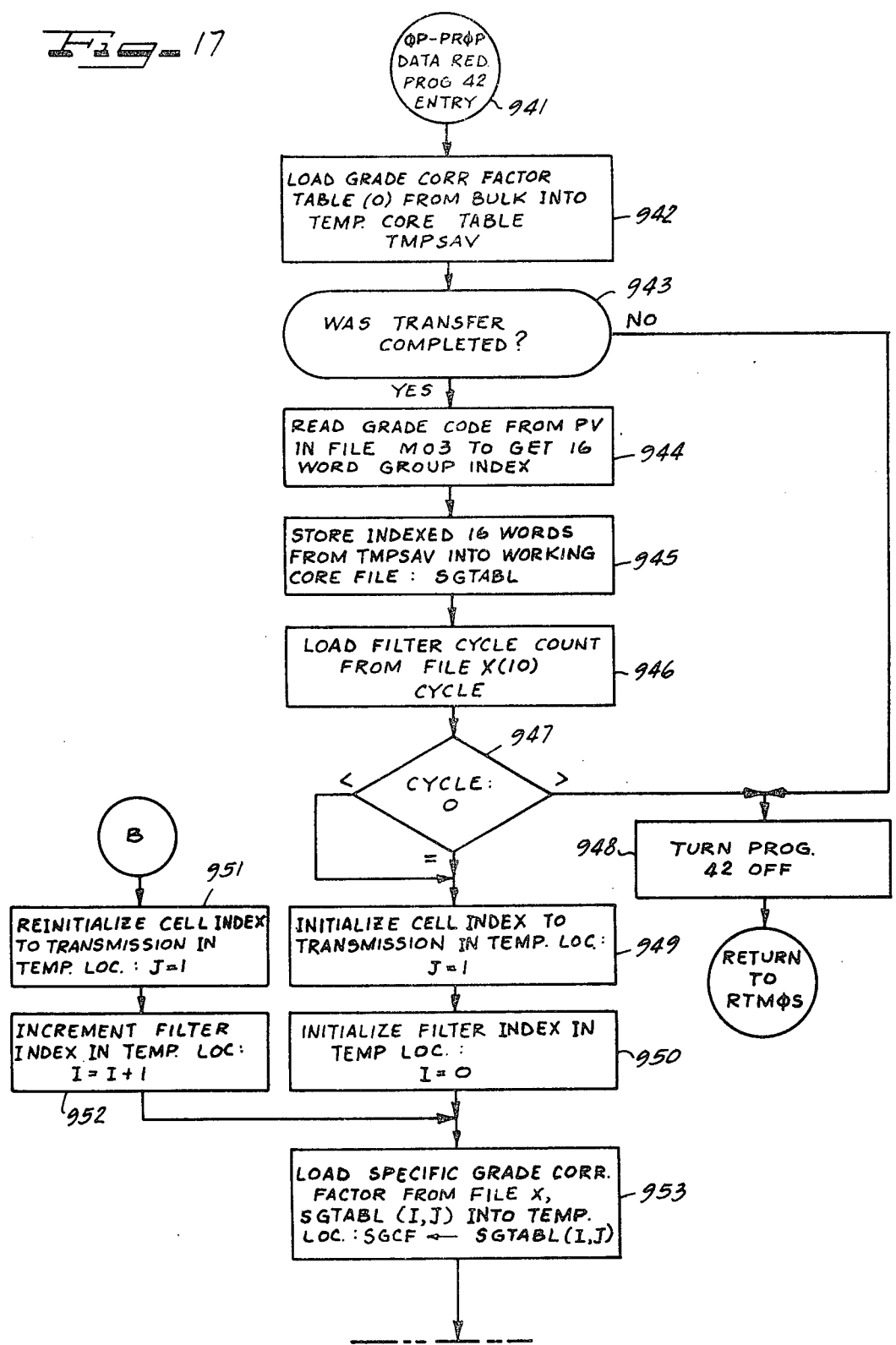

Supplementary Explanation of the Program Steps of FIG. 17

| Program Step | Comment |
|---|---|
| 941 | Entry to Program Forty Two |
| 942 | Load grade correction factor table from bulk storage into the temporary core storage table TMPSAV. |
| 943 | Was transfer to TMPSAV completed? |
| 944 | Read the grade code from the process variable input file MO3 to obtain a sixteen word group index. |
| 945 | Transfer TMPSAV into the working core file SGTABL. |
| 946 | Load content of FILE X (ten) into CYCLE. This register is decremented during operation of Program Fourteen. |
| 947 | Compare CYCLE and zero. |
| 948 | If cycle is greater than zero, turn Program Forty Two off and return to RTMOS. |
| 949 | Set location J to one. |
| 950 | Set location I to zero. |
| 951 | On entry at B, set location J to one. |
| 952 | Increment the value in location I by one. |
| 953 | Load value from SGTABL of FILE X (See Table 7) for current values of I and J into SGCF. |

Table 18

Figure 18:
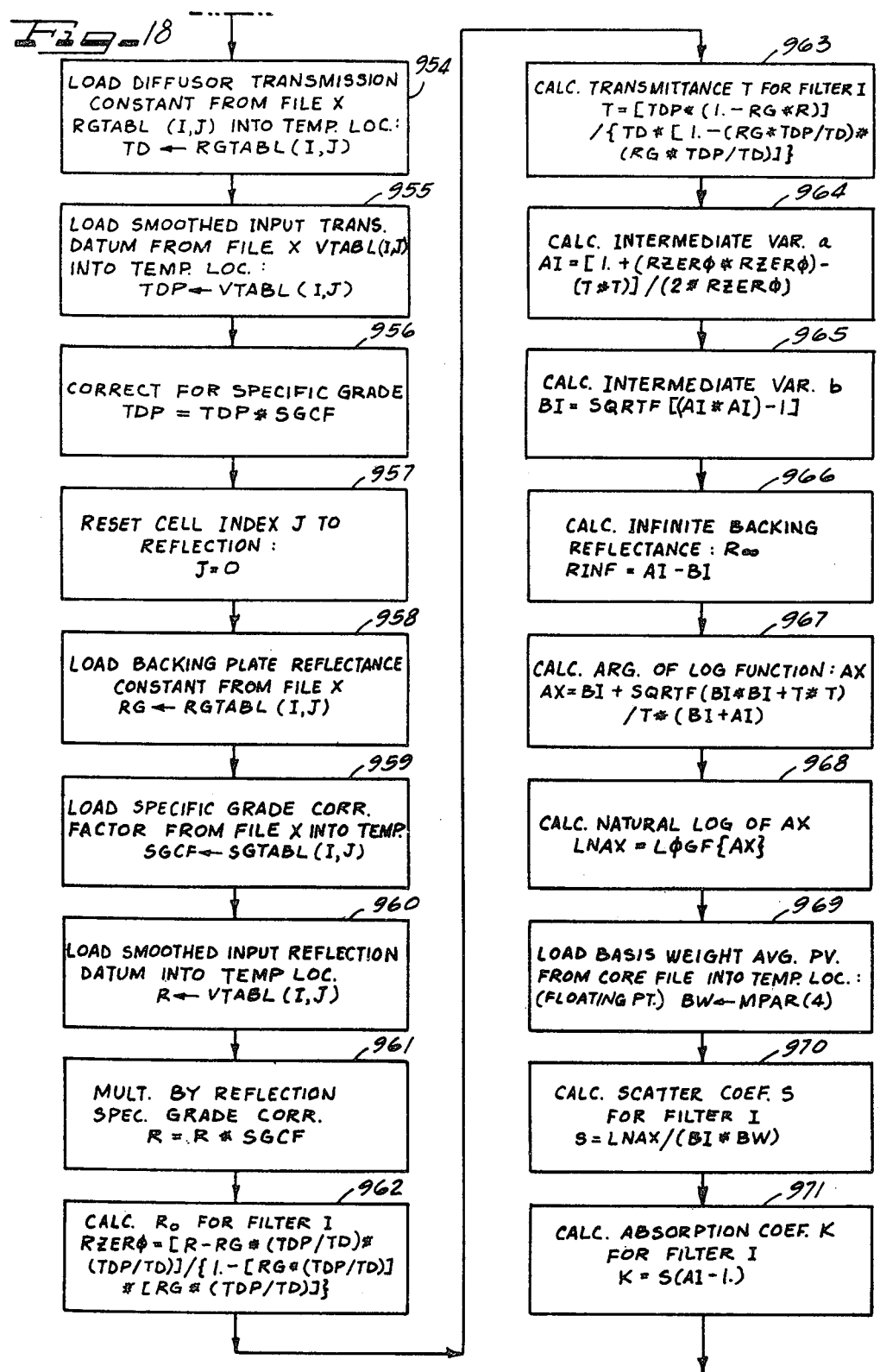

Supplementary Explanation of the Program Steps of FIG. 18

| Program Step | Comment |
|---|---|
| 954 | Load pertinent value from RGTABL into TD. |
| 955 | Load indexed content of VTABL into TDP. |
| 956 | Multiply by SGCF (See block 953, FIG. 17). |
| 957 | Set J to zero. |
| 958 | Load indexed value from RGTABL of FILE X into RG. |
| 959 | Load desired value from SGTABL of FILE X into SGCF. |
| 960 | Load indexed value from VTABL of FILE X into R. |
| 961 | Multiply R and SGCF and store product in R. |
| 962 | Calculate $R_o$ using the equation given in Table 6 in conventional form. |
| 963 | Calculate transmittance T using the equation of Table 6. |
| 964 | Calculate the value A/2 where A is given in Table 6. |
| 965 | See the equation for $R_\infty$ in Table 6. |
| 966 | See the equation for $R_\infty$ in Table 6. |
| 967– 970 | The scattering coefficient S is also calculated using Kubelka-Munk Theory on the basis of the equation: |

Table 18-continued

Supplementary Explanation of the Program Steps of FIG. 18

| Program Step | Comment |
|---|---|
| | $S = \dfrac{1}{b \times \text{Basis Weight}} \times$ [Arc Sinh $(b/T)$ − Arc Sinh $b$] where $b = \sqrt{a^2 - 1}$ and $a = (1 + R_o^2 - T^2)/2 R_o$ |
| 971 | The absorption coefficient K is found from the equation: K = S (a − 1). |

Table 19

Figure 19:
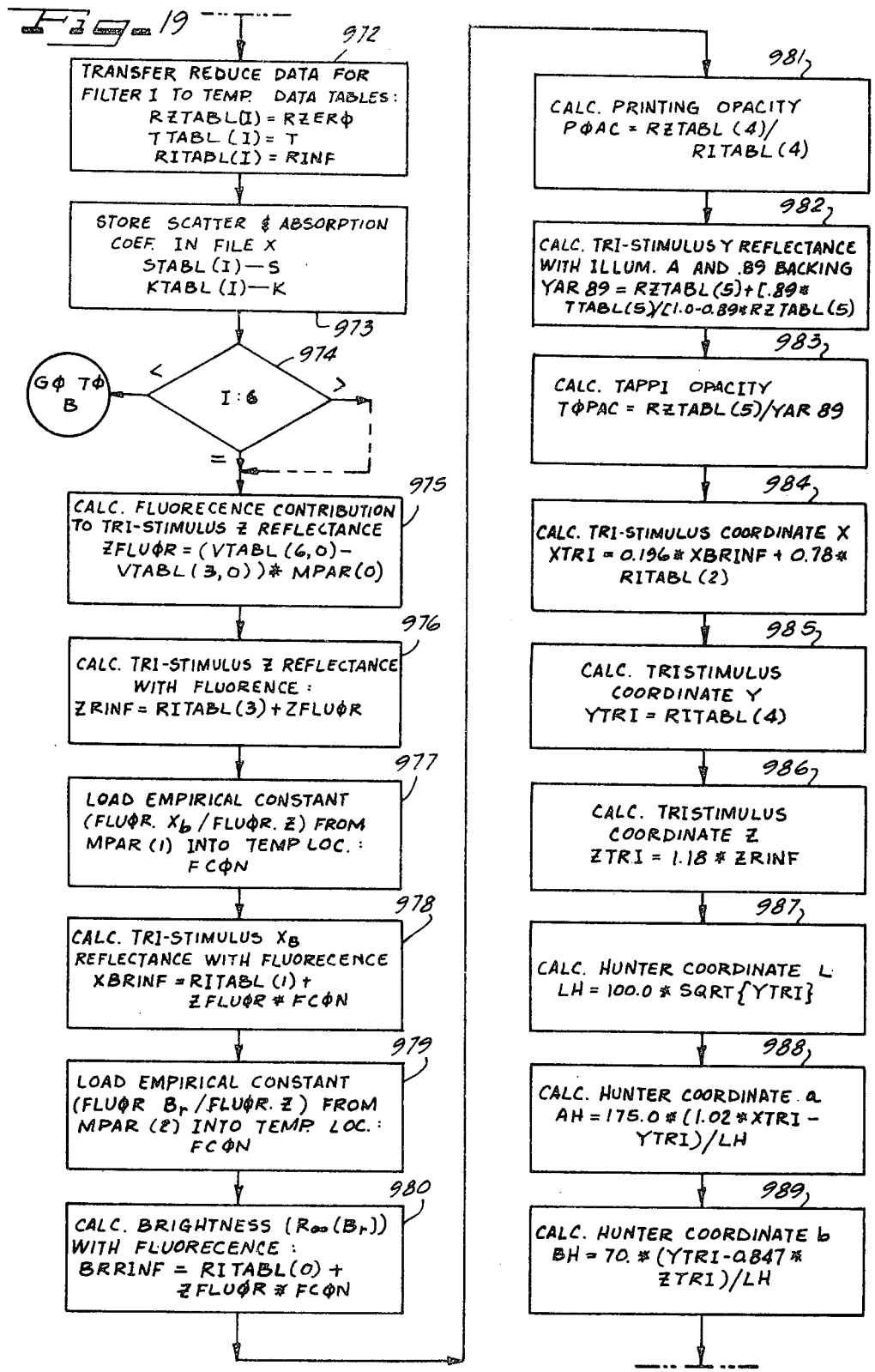

Supplementary Explanation of the Program Steps of FIG. 19

| Program Step | Comment |
|---|---|
| 972 | Transfer the calculated data to the temporary data tables at the locations corresponding to the current value of I. |
| 973 | Store calculated scattering coefficient S and absorption coefficient K in FILE X. |
| 974 | Go to entry B at block 951, FIG. 17, to repeat the calculations for the other filter wheel positions if I is less than six. |
| 975 | See the calculation of $F_Z$ in the section of this specification entitled "Structure and Operation of a Prototype Optical Monitoring Device". |
| 976 | Calculate $R_\infty$ including fluorescence contribution and store at ZRINF. |
| 977– 978 | For example $F_{X(Blue)}$ may equal 1.204 $F_Z$ where $F_Z$ is found at step 975, and $R_\infty$ ($X_{Blue}$) plus $F_{X(Blue)}$ gives the desired value for BRINF. |
| 979– 980 | For example $F_{Brightness}$ may equal 0.864 $F_Z$. Thus $R_\infty$ (Brightness with fluorescense) plus $F_{Brightness}$, and this sum is stored at BRRINF. |
| 981 | Printing opacity R.89 is calculated by dividing $R_o$ by $R_\infty$ (both from the Yc filter wheel position. |
| 982– 983 | For TAPPI opacity, obtain the ratio of $R_o$ to R.89 using the $Y_A$ filter wheel position. |
| 984 | The C.I.E. X tristimulus value is calculated as follows: X = 0.196 $R_\infty$ ($X_{Blue}$) + .78 $R_\infty$ (X Red) |
| 985 | C.I.E. tristimulus value Y = $R_\infty$ ($Y_c$) |
| 986 | C.I.E. tristimulus value Z = 1.18 $R_\infty$ (Z) |
| 987 | Compare block 985. |
| 988 | See blocks 984, 985 and 987. |
| 989 | See blocks 985, 986 and 987. |

Table 20

Figure 20:
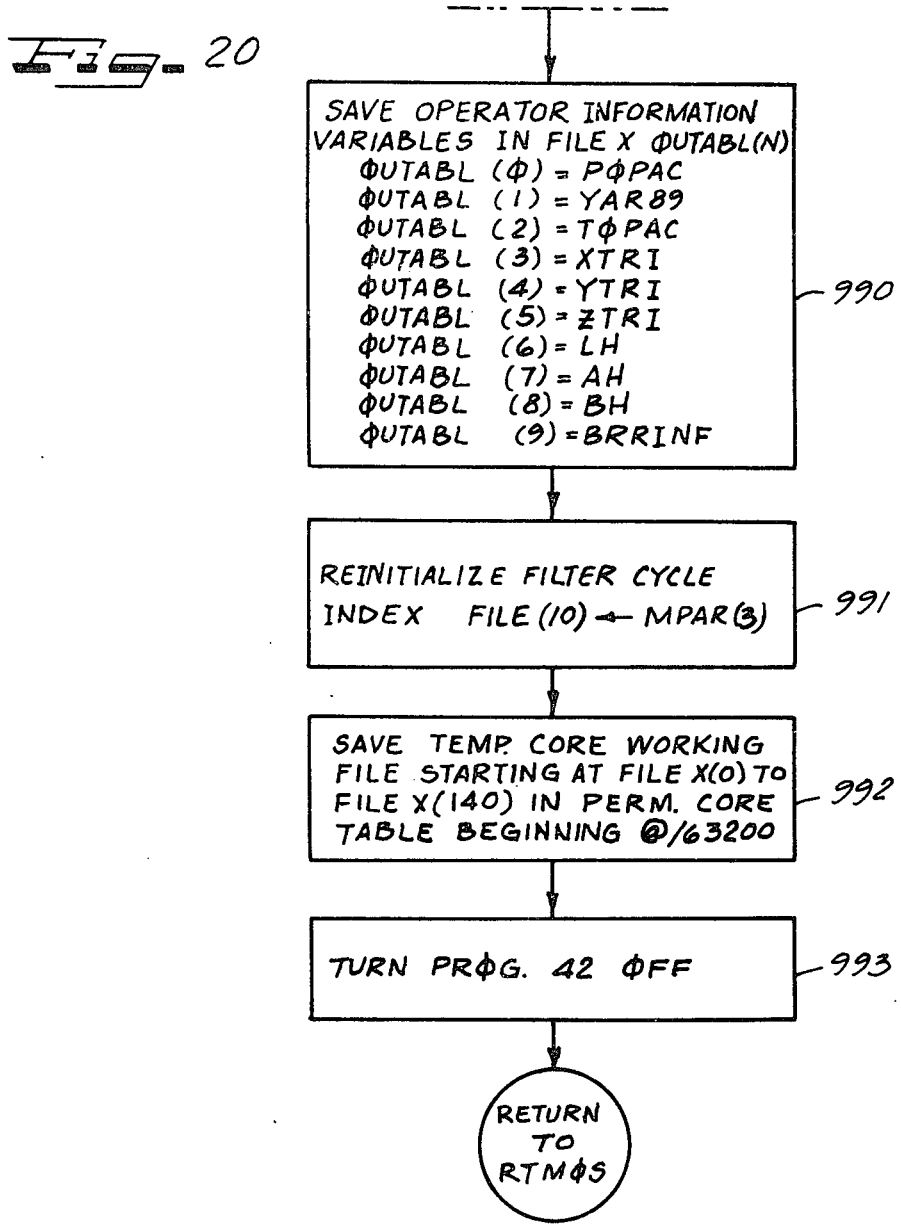

Supplementary Explanation of the Program Steps of FIG. 20

| Program Step | Comment |
|---|---|
| 990 | See Table 7 for a showing of OUTABL. The data in OUTABL is available for print out on demand. |
| 991 | The reset value at FILE X (one hundred thirty seven) is placed at FILE X(ten). See Table 7. |
| 992 | Save FILE X in the permanent core table beginning at location 63200. |
| 993 | Turn Program Forty Two off and |

Table 20-continued

Supplementary Explanation of the Program Steps of FIG. 20

| Program Step | Comment |
|---|---|
| | return to RTMOS. |

COMMENTS REGARDING PROGRAM FORTY-TWO

1. Although not indicated as yet, the output of the fluorescent contribution to TAPPI brightness will be part of the computer output when the programs are finalized.

2. Program Forty-Two has been checked out against a currently operating program used on a research Hewlett-Packard computer and both give the same results.

3. It is planned to study means of determining and using the Specific Grade Correction Factor other than that described in Program Forty-Two. It may be decided to apply such correction directly to $R_{\infty}$ rather than to the smoothed values of $T_{pd}$ and $R_g$. The transmittance of the paper, T, may not need any Specific Grade Correction and could then be used along with the corrected $R_{\infty}$ to compute the scattering and absorption coefficients $s$ and $k$. The later will be very useful and may represent preferred parameters for closed loop control.

SUMMARY OF OPERATION OF PROGRAM FORTY-TWO

The purpose of this program is to reduce the corrected reflectance and transmittance data into terms with which papermakers are familiar and upon which paper optical specifications are based; e.g., brightness, opacity, color and fluorescence. A description of this program follows.

1. The data reduction steps of this program are performed only if the term "CYCLE" which is decremented in Program Fourteen, is zero or negative. Otherwise, this data reduction routine is by-passed completely.

2. The exponentially smoothed reflectance and transmittance data acquired by Program Fourteen are first corrected by multiplying each of the fourteen values by an appropriate Specific Grade Correction Factor (SGCF). With a few exceptions the SGCF'S provide only small corrections, if any at all. The SGCF'S serve two purposes.

a. They compensate for the small errors resulting from the use of the Kubelka-Munk or energy balance equations when the latter do not apply exactly.

b. They allow the reduced data values to precisely correspond to any one of several possible off-line instruments. Existing off-line instruments do not agree among themselves. Thus, the choice of the off-line instrument for performing the audit testing will affect the values of the SGCF'S.

3. The next part of Program Forty-Two computes and stores the values of $R_o$, T, $R_\infty$, S and K of the paper being measured for each of the first six of the seven OMOD filter positions. Kubelka-Munk and IPC derived energy balance equations are used for this purpose. Note that prior to these calculations, the reflectance values were those of the single ply of paper when backed by the Lucalux and were symbolized by $R_g$. Similarly, the former transmittance values were those of the single ply of paper in series with the Lucalux, now serving as a diffusing window. This was symbolized by $T_{pd}$.

The phenomenon of fluorescence is not accounted for by Kubelka-Munk theory. For this reason the OMOD optical geometry was chosen to exclude fluorescence by eliminating ultra violet (U.V.) light from the incident light beam of the first six filter positions. For reasons explained later, the seventh filter position permits the reflectance of the Z function with ultra violet energy present in the incident beam.

4. The degree of fluorescence as measured by the "Fluorescent Contribution" is determined next. Fluorescence occurs as a result of excitation of special dyes (optical brightness or fluorescent dyes) by ultra violet energy contained within the incident light beam(s). The "Fluorescent Contribution" is defined here to be in the increase of the reflected light flux that occurs as a result of the existence of some standard quantity of ultra violet energy in the incident light beam.

Such U.V. energy is rapidly absorbed by the outer layers of most conventional papers. Consequently, fluorescence is primarily a characteristic of the surface of the paper being viewed. Thus, for practical purposes, the value of $[R_g$ (with fluor.) - $R_g$ (without fluor)] = $[R_{\infty}$ (with fluor.) - $R_{\infty}$ (without fluor.)] when the same incident light beam containing the same U.V. energy is used in both cases. The right side of this equation is by the definition above, the Fluorescent Contribution provided the standard quantity of U.V. light is employed in the incident beam. The left side of this equation is a quantity measureable on a single ply of the moving paper web. In the case of the OMOD a measure of the fluorescent contribution to the Z function reflectance is obtained from the term, [g (Filter No. 7) - $R_g$ (Filter No. 4)]. The filter arrangement existing in the No. 7 OMOD filter position permits about twice the standard quantity of U.V. energy to strike the paper. (The U.V. energy in the incident beam of the Standard TAPPI Brightness Tester is considered to be the standard quantity here). This increases the sensitivity of this measurement by two-fold. It also necessitates the use of a proportionality constant of approximately one-half to compute the value of the standard Fluorescent Contribution to the Z function reflectance.

The Fluorescent Contribution to the reflectance of the $X_B$ and Brightness functions can be computed directly from the Z function Fluorescent Contribution. The multiplication factors involved are constant for a given optical brightner and need to be changed only if the type of optical brightner is changed. The Fluorescent Contributor to the $Y_C$, $Y_A$ and $X_R$ functions can be ignored as being inconsequential for the typical optical brightner used in the paper industry today.

5. Defining equations are used to compute and store for accessible putout values of the following:

a. Standard TAPPI Brightness
    b. Printing opacity based on illuminant C
    c. $R_{89}$ based on illuminant A
    d. TAPPI opacity based on illuminant A
    e. X Tristimulus value
    f. Y Tristimulus value
    g. Z Tristimulus value
    h. Hunter Coordinate, L
    i. Hunter Coordinate, a J. Hunter Coordinate, b k. Fluorescent Contribution to TAPPI Brightness

DISCUSSION RELATING TO THE PRESENT INVENTION BASED ON A PAPER PUBLISHED IN 1974

The following pages 107-138 are excerpts based on a paper prepared for the American Paper Institute, which paper is dated Jan. 10, 1974 and has been published in 1974. The paper was prepared by an author who is a joint contributor to certain improvements described but not claimed herein. The paper exists in printed form, and is incorporated herein by reference except as included in the excerpts at pages 107-138. The incorporated paper is identified as "REPORT NO. 58, TO: American Paper Institute Instrumentation Program," "SUBJECT: An Analysis of On-Machine Optical Instrumentation," "DATE: Jan. 10, 1974" and is submitted by the Institute of Paper Chemistry, Appleton, Wisconsin. For the sake of further identification, a copy of pages 3 through 28 of the paper as printed is included as pages 106a – 106z herein.

The Institute of Paper Chemistry was retained to evaluate an early conception of an on-the paper-machine optical monitoring device for simultaneous measurement of relfected and transmitted light, and to assist in the optimum implementation of such conception. Accordingly, a substantial portion of the work reported in the following excerpts appears to inure as part of the original conception.

The following discussion is presented as constituting a description bearing on the background of the invention and as clarifying and amplifying on the nature of such invention, even through the paper may also include subject matter which is based on work entirely independent of the project sponsored by the assignee of the present invention. Further, the paper will indicate the range of equivalents to the illustrated embodiment with respect to matters such as spectrum and geometry of illumination.

Summary

Various aspects of the on-machine measurement of the optical properties of paper for the control of opacity, standard brightness, and color have been examined. Whereas many optical property specifications are based on reflectances determined on opaque pads of paper, on-machine measurements are limited to the various optical values which can be determined on single thicknesses of a moving web. Thus, one must either control to the optical property which can be measured on-machine or strive to develop reliable correlations between the on-machine and off-machine measurements. The latter approach is more desirable. For this purpose, it is advantageous to adopt the design features of the off-machine testing apparatus to the fullest extent possible for on-machine use. Fortunately, the important factors in optical instrument design related to spectral characteristics, geometry, and photometric linearity can be translated to on-machine use with considerable exactness.

A large number of different approaches are possible in the measurement of optical properties of single sheets for purposes of control. Of these, however, distinctions can be made between single measurements, of reflectance, for example, and the measurement of two optical parameters for the same sampled area. The latter approach permits calculation of thick pad reflectivity values using appropriate theory with an essential independence of basis weight, whereas single reflectance data are functions of basis weight requiring empirical compensation. Although various possible pairs of optical measurements can be made on the same specimen area, among the most satisfactory for the use of theory are reflectance with black body backing and transmittance. The Kubelka-Munk theory, though not rigorously applicable in practice, has been shown to be rather successful in predicting thick pad reflectivity from such data in laboratory tests for white papers of reasonable homogeneity. It is less successful for deeply colored papers and for sheets of very low basis weight.

The sensitivity of spacing of white backings from paper specimens was measured with respect to the color of various commercial papers. At a central spacing of 0.32 cm, it was determined that a variation in spacing of about 0.020 inches (0.05 cm) is possible for most papers without noticeable color difference.

Optical measurements would be made on-machine on webs of varying moisture content and at elevated temperatures compared to a controlled laboratory testing environment. An experimental study of the effect of changing moisture content (R.H. range of 5 to 84%) on color showed small effects for most white papers, which were attributed to differences in surface structure. Somewhat larger effects were noted using directional illumination compared to diffuse illumination. The largest effects, for some colored papers, were attributed to changing spectral absorption characteristics of the dyestuff. Sheet moisture content effects on optical properties were judged to be within tolerable limits over a range corresponding to relative humidities between 5 and 50%.

The effect of temperature on the color of various commercial papers was studied over a range of 23° to 62° C. Important effects were found only for two colored papers. It was noted that significant elevations of specimen surface temperature can occur in optical apparatus employing high-intensity illumination.

Most other variables involving paper properties, machine operation, and mill environmental conditions are unlikely to be eliminated through instrument design or through the development of appropriate compensating factors. For these remaining factors empirical correlations would be required to establish agreement between optical data or obtained on and off machine.

INTRODUCTION

Specifications for the various optical properties of paper are presently based on measurements made with laboratory instruments. Considerable standardization of optical instrumentation and testing methods have been developed, but now instruments and analytical methods are often introduced to the industry as well. Changes are welcome when they provide advantages in such areas as the utility of the measurement, improved accuracy, better agreement between laboratories, and in overall testing costs. The well-established advantages of industry-wide standardization in the measurement of the optical properties, however, must always receive serious consideration.

In recent years, the control of paper quality on the paper machine has grown in importance, and, for optical properties, on-line control is a very practical objective. Good control strategy requires that the properties of the sheet be determined rapidly on the moving web, but it is usually not possible to duplicate laboratory instrumentation for on-machine use. Whereas on-machine measurements are limited to such data as can be acquired on a single thickness of paper, optical properties such as brightness and color are determined on multiple thicknesses. Too often, optical instrumentation is developed for on-machine use with emphasis on the control function, but without serious consideration given to the further problem of conforming to off-machine optical property standards. The implied assumption is that a good reliable correlation will exist between the on-machine and off-machine optical measurements. Perhaps the most logical approach to the development of on-machine optical instrumentation is to design for maximum conformance with laboratory instrumentation in such factors as instrument geometry and spectral characteristics, to employ existing theory as far as possible to inter-relate single-sheet versus multiple-sheet optical measurements and to employ empirical correlations to the minimum extent required.

As on-machine optical instrumentation becomes more widely adopted, the advantages of continuously monitoring the optical properties of paper in real-time compared to the intermittent and few data which can be acquired by off-machine testing could lead to the use of specifications in the buying and selling of paper which are based on the on-machine instrumentation. Should this ever occur, it is particularly desirable that such on-machine specifications bear the highest possible degree of correlation with the off-machine specifications in current use.

In this report, many of the factors involved in the optical characterization of a moving web in a paper machine environment are discussed relative to the off-machine properties of brightness, color and opacity.

OPTICAL PROPERTY MEASUREMENT AND SPECIFICATION

Brightness

Papermaker's brightness, sometimes called G.E. brightness and now "standard brightness" was first established in the early 1930's as the particular reflectivity ($R_{\infty}$) of paper determined with an instrument having a specified spectral response, specified geometry, and good photometric accuracy (1). At the same time, a system of calibration was developed whereby opal glass and paper standards are furnished periodically for each instrument.

In the early days, the scale was based on "smoked" magnesium oxide but, because of difficulty in arriving at a reproducible reflecting surface, a technique for measuring the absolute reflectance of magnesium oxide was developed (2). Thus, a total system (3) was made available so that this particular reflectivity could be measured industry-wide with an accuracy of about ± 0.3 reflectivity units. TAPPI standards T217 and T452 give the detailed specifications for the measurement of standard brightness for pulp and for paper and paperboard respectively. The following specifications are involved.

Spectral Response

The effective wavelength of an instrument for the measurement of standard brightness is 457 nm. Although the effective wavelength is the most important parameter described the spectral response, wavelength bandwidth and shape of the function also influence the result and are specified. The standardized overall spectral response of the brightness instrument which includes the spectral power distribution of the light source, the spectral transmittance of the glass lenses and filters, and the spectral response of the phototube is given in Table I.

Table I

Spectral Response of an Instrument for the Measurement of Standard Brightness

| Wavelength, nm | Spectral Response Arbitrary Units |
|---|---|
| 400 | 1.0 |
| 405 | 2.9 |
| 410 | 6.7 |
| 415 | 12.1 |
| 420 | 18.2 |
| 425 | 25.8 |
| 430 | 34.5 |
| 435 | 44.9 |
| 440 | 57.6 |
| 445 | 70.0 |
| 450 | 82.5 |
| 455 | 94.1 |
| 460 | 100.0 |
| 465 | 99.3 |
| 470 | 88.7 |
| 475 | 72.5 |
| 480 | 53.1 |
| 485 | 34.0 |
| 490 | 20.3 |
| 495 | 11.1 |
| 500 | 5.6 |
| 505 | 2.2 |
| 510 | 0.3 |

The prescribed spectral response precludes use of a spectrophotometer employing a narrow bandwidth at 457 nm for the accurate measurement of standard brightness.

The spectral response function was chosen in the blue region of the spectrum for maximum sensitivity to changes in bleaching and the fading of paper with time. Once specified, however, the spectral response of different instruments must be maintained to close tolerances for reproducibility in measurement on an industry-wide basis.

When papers exhibit fluorescence, whether naturally or because of the addition of fluorescent dyes, the spectral power distribution of the light incident on the specimen must be specified. For standard brightness, the specified spectral power distribution of the light incident on the specimen is given in Table II. Thus, adherence to the spectral specifications of Tables I and II permits the accurate determination of standard brightness of fluorescent as well as nonfluorescent papers.

Table II

| Wavelengths, nm | Spectral Power Distribution of the Light Incident on the Specimen Arbitrary Units |
|---|---|
| 320 | 0.0 |
| 330 | 0.7 |
| 340 | 9.7 |
| 360 | 9.7 |
| 380 | 17.1 |
| 400 | 26.0 |
| 420 | 37.2 |
| 440 | 50.3 |
| 460 | 64.1 |
| 480 | 80.0 |
| 500 | 100.0 |

In addition, the spectral transmittance of the filters and the phototube response are selected such that the instrument has negligible response to near-infrared radiant energy whether reflected from the specimen or as a result of speciment infrared fluorescence (4). It is important to note that some colored glass filters with essentially no transmittance in the red region of the spectrum will transmit substantially in the near infrared.

Geometry

The geometry employed for the measurement of brightness is illumination at 45° and normal viewing with the incident and reflected beam cone half-angles specified at 11.5° and 22.5° respectively. The angles of illumination and viewing are critical as paper surfaces are not ideal diffusers, and the numerical values obtained are a function of the particular geometry employed. Paper surfaces also exhibit directional effects. The light reflected when the specimen is illuminated in the "machine direction" is generally less than if the specimen is illuminated in the "across-machine direction." The brightness measurement is usually performed with the specimen illuminated in the "machine direction" and on the felt or top side. A sufficient number of sheets are required to form an opaque pad.

In the more translucent papers, and appreciable penetration of light into the sample occurs. As a result of internal light scattering, the illuminated area may differ significantly from the area of reflectance or light emergence. When this condition exists, the relative dimensions of the areas illuminated and viewed, the distribution of light on the illuminated spot, the alignment of the illuminated and viewed areas and their shapes can influence the result. In the instrument employed for the brightness measurement, the viewed area and the size and position of the illuminated spot are adjusted to pdescribed standards. Conformance with the standard is ensured through use of the calibration standards. Properly adjusted, the instrument can be used to measure standard brightness of strongly translucent as well as opaque material.

Photometry

The photometric accuracy of an instrument for the measurement of brightness should be better than 0.1 point on a 0–100 scale (5). The overall error introduced through discrepancies in spectral response, geometry and the basis of standardization must total less than 0.3 point.

TAPPI OPACITY

Opacity has long been defined in the paper industry at 100 times the ratio of the diffuse reflectance of a single sheet backed with a black body to its diffuse reflectance backed by a white body having an effective absolute reflectance of 0.89. An instrument designed and built in the early 1930's and has formed the basis of a system for determining TAPPI Opacity (6).

SPECTRAL RESPONSE

The overall spectral response of the instrument including the spectral power distribution of the light source, spectral transmittance of the glass lenses and filter, spectral reflectivity of the integrating cavity lining and spectral response of the photocell is that the $E_a y$ function (visibility function, Illuminant A) of the CIE system (7). The effective wavelength is 572 nm and the function extends over the entire visible spectrum. The specified broad-band spectral function makes the use of narrow-band instruments inappropriate for the measurement of opacity even though the effective wavelength is proper.

Fluorescent dyes, known in industry as optical brighteners, have a rather small, if not negligible, influence on opacity as the spectral response of the instrument in the usual fluorescent region (blue) of the spectrum is quite low. Also, the fluorescent radiation from a single sheet probably would not be too different when backed by a black or white body.

The spectral reflectivity of the integrating cavity lining does influence the overall spectral response of the instrument (3) and, because it is difficult to maintain a constant lining reflectance, a system for checking and maintaining the lining reflectance is essential to good accuracy.

Geometry

The geometry employed for the measurement of opacity is illumination at 20° and diffuse viewing. The photodetector receives light that is both diffusely and specularly reflected from the specimen and, because there is no baffle, the photodetector also views the light directly reflected from the specimen. The ratio of diffusely to directly reflected light depends upon the level of reflectance of the integrating cavity lining (physical dimensions also are influencing factors but remain constant) and, as this ratio changes, significant changes in measured opacity can occur (8).

The illuminated area is about 10 mm in diameter with a specimen aperture of about 14.3 mm in diameter. If translucent papers or standards are to be evaluated or used, the ratio of the viewed to the illuminated area is important (8). The state of focus and alignment of the optical system particularly influences the values obtained for translucent materials.

Stray light caused by a dirty or misaligned optical system can be a source of error. The optical system should be cleaned and aligned such that the difference in scale reading with the black body over the specimen opening when the light is blocked off before entering the cavity and with the light passing through the cavity into the black body should not be over 0.5 (0–100 scale). The reflectance of the black body should not be more than about 0.1%. The instrument scale is adjusted to read zero when the stray light is included.

Photometry

The photometric accuracy of different original instruments, employing a photocell-galvanometer system, varied from near perfect linearity to diviations as much as several points, depending upon the components. More recently, with the addition of solid state amplifiers and digital readouts, the photometric accuracy can be better than 0.1 (0–100 scale). Calibration Standardization In the measurement of the ratio $R_o/R_{0.89}$, it is necessary that the white body have an effective reflectance of 0.89. The instrument is equipped with a rotatable tube, one end of which contains a black cavity and the other the white body. A sheet of paper is placed over the specimen opening and, alternately, the black and white bodies are brought into position. The usual white body consists of a plug of appropriately surfaced magnesium carbonate within a protective glass cover. Changing the spacing between the surface of the magnesium carbonate and the specimen permits adjustment of the effective reflectance of the white body. There are two generally accepted means for arriving at the proper white body effective reflectance. One is to employ properly calibrated opal glass standards. While convenient, unless the instrument is properly adjusted with respect to translucency effects, substantial error can result. As constructed originally, the specimen supporting surface often departed from the intended plane. Thus, while the paper could follow a particular contour, the rigid glass standards will not, resulting in further error. After correcting these potential defects, it is possible to use opal glass standards and take advantage of their great convenience.

A second more basic method consists of determining $R_o$ and $R_{oo}$ for a particular paper specimen on the absolute scale and, through use of the relationship sometimes known as the "balance of energy" equation (9) or the Kubekla-Munk theory (10, 11, 12), to calculate $R_{0.89}$ for that specimen. The white body can then be adjusted so that this value is obtained instrumentally. Care should be exercised so that all reflectances are obtained on an identical area of the specimen. Charts are available (13) relating the reflectances $R_o$, $R_{oo}$ and $R_{0.89}$ or an appropriately programmed computer can be used to calculate the $R_{0.89}$ value.

Paper opacity standards calibrated for use with the opacimeter are now also available. These are convenient to use and will eliminate some of the difficulties associated with the opal glass calibration standards.

Magnesium oxide powder with an assigned absolute reflectance value is also available for use in calibrating the opacimeter for the measurement of reflectance on the absolute scale.

PRINTING OPACITY

While the choice of spectral response for the measurement of opacity was excellent, the choice of the ratio $R_o/R_{0.89}$ as opposed to $R_o/R_{oo}$ was not. Printing opacity ($R_o/R_{oo}$) more nearly relates to the end use of the product and would eliminate the problem of adjusting the white body (14). The fact that a single sheet is required for the measurement of TAPPI Opacity whereas an opaque pad is required for printing opacity appears to be a factor in the reluctance of the industry to change. It is more convenient to determine the opacity of the single sheet using the white body.

COLOR

Spectrophotometers and filter colorimeters are the two main classes of instruments employed in the measurement of color. The spectrophotometer provides basic reflectivity information as a function of wavelength over the entire visible spectrum. The reflectivity ($R_{oo}$), obtained on the thick pads of paper, with the values based on the absolute scale is basic to color measurement. The reflectivity curve contains the essential information regarding the color of the object, but considerable computation is required to derive the desired colorimetric specifications.

Spectral

In the numerical specification of color, it is necessary to specify the spectral characteristics of the illuminant and the spectral response of the observer. The CIE system (7) gives the spectral power distribution for various illuminants and the spectral response of the standard observer. Illuminant C has been used almost exclusively in the past in the specification of color, however, the use of Illuminant $D_{6500}$ (15) is now being considered. The specifications for Illuminant $D_{6500}$ include the ultraviolet region of the spectrum. The ultraviolet region for Illuminant C was not specified.

For color definition in the CIE system, the psychophysical response of the "standard observer" to the spectral distribution of light reflected from a specimen (as provided by the spectral power distribution of the illuminant and the spectral reflectivity curve) is matched by a combination of three standard stimuli, each of appropriate power. The relative levels for the three separate stimuli are the tristimulus values which together constitute the chromaticity of a color. It is more useful to compute the fraction each stimulus has to their sum since only two of the three fractions need be specified for chromaticity definition. It then becomes possible to restate the chromaticity of the measured color, for a given illuminant, in terms of "dominant wavelength" and "purity." To complete this specification of color, the luminous reflectance of the specimen is provided directly in the CIE system by the tristimulus value Y.

Geometry

Four illumination and viewing conditions are recommended for use in the CIE system. These include illumination at 45° and viewing normal to the surface (0°), normal illumination with 45° viewing, diffuse illumination with normal viewing and normal illumination with diffuse viewing. Various advantages and disadvantages relate to each of these geometries from the viewpoint of best representing visual estimates of color. Generally, the geometry employed for visual inspection is more nearly 45°–0° or 0°–45°. Thus, an instrument equipped with this geometry would be expected to agree more closely with visual estimates than an instrument equipped with diffuse--normal geometry. It can be clearly demonstrated that a colorimetric evaluation using an instrument equipped with diffuse-normal geometry does not correlate closely with visual estimates for certain surfaces. Also, it is difficult to maintain a constant integrating cavity lining reflectance for long periods. The diffuse-normal geometry, however, is less sensititve to surface roughness and will give more reproducible results when specimens having an irregular surface are evaluated.

Control of the sizes, shapes and relative positions of the illuminated and viewed areas is also required for proper accounting of specimen translucency effects.

Photometry

Photometric accuracy of better than 0.1 point (0–100 scale) is desired.

FILTER COLORIMETERS

Though the spectrophotometric approach to color measurement is the most basic and rigorous, its greater cost and computational demands have led to the development of filter colorimetry. One approach involves the use of suitable lamp, filters and photodetector combinations chosen to match the spectral functions of the CIE system (x, y, z). Thus, the instrument output may be in the form of the tristimulus values of the CIE system. Althgough the y and z functions can be matched quite well, the double peak of the x function precludes the use of a single filter-photocell combination. Recourse is made either to the computation of the blue contribution to the x function from the z function (three-filter colorimeter) (16) or to the use of two filters with properly weighted combined output (four-filter colorimeter) for the $x$ function. The latter gives a more accurate measure of the X tristimulus value particularly for specimens having spectral reflectivity curves with a steep slope through the blue region of the Spectrum. For color matching, particularly in control applications, the three or four-filter colorimeter may prove useful for many colors of commercial interest. However, it is subject to many limitations such as basic accuracy and the fact that colorimetric data are obtained for a single illuminant. For instance, the match may be metameric and under another illuminant there could be a serious mismatch.

Another form of colorimeter involves the use of a larger number of narrow-band filters with transmittance peaks distributed across the visible spectrum. If the filter transmittances are confined to sufficiently narrow ranges of wavelength and an adequate number are used, one may approach the utility of an abridged spectrophotometer. For many purposes of control, the abridged spectrophotometer can have important advantages over the three or four-filter colorimeter.

If a specimen exhibits fluorescence, the best spectrophotometer or filter colorimeter design utilizes illuminants with broad spectral power distribution, including appropriate intensities in the ultraviolet, with viewing through a monochromator for the spectrophotometer and through appropriate filters for the colorimeter. Thus, the fluorescent radiation will be excited in accordance with the spectral power distribution of the illuminant and the photodetector will view the reflected light and fluorescent radiation properly.

ON-MACHINE MEASUREMENT OF OPTICAL PROPERTIES

The optical information which can be acquired on the moving web of a paper machine is limited essentially to that which can be obtined using a single sheet. Reflectances can be obtained for various conditions of illumination of the single sheet and for different backings. The backing can be black body or established at various reflectance levels. Ordinarily the backing would consist of ceramic or glass placed either at a specific distance from the sheet surface or in contact with the sheet. In addition to such reflectivity measurements as can be obtained, it is often possible to obtain useful transmittance information (except for very opaque sheets). Of course, where the transmittance is very low, the reflectance of a single sheet will approach the true $R_{oo}$ value.

Optical specifications which properly apply to thick pad reflectances, $R_{oo}$, are not readily abandoned in favor of specifications based on single sheet reflectances. Hence, the question of correlation of such on-machine data as can be obtained with actual experimentally determined $R_{oo}$ data is of interest. The most useful approach is to utilize to the fullest possible extent the existing theory which permits calculation of $R_{oo}$ from on-machine optical data. To the extent that such calculated values are not in agreement with the experimental data, empirical correlations could then be applied to bridge the remaining gap. Such an approach is more desirable than is dependence on empirical correlations alone especially if the calculated result is in close agreement with off-machine determinations.

The equations, based on the Kubelka-Munk theory, which interrelate various reflection and transmittance measurements are of principal interest in obtaining estimates of the reflectivity, $R_{oo}$, from on-machine measurements. It is always necessary to obtain two different optical parameters preferably on the same areas of single sheets for the calculation of $R_{oo}$ using these equations. The two measurements can take many forms. For example, the reflectance of paper with black body backing ($R_o$) along with transmittance (T) is both appropriate and experimentally desirable. It is also possible to employ any two reflectances, obtained with different backings, but this introduces problems, particularly with the backing reflectance color. Through the appropriate measurement of two optical parameters, it is also possible to characterize papers in terms of their scattering and absorption powers--not possible with single reflectance measurements.

The theoretical relationship between $R_{oo}$, $R_o$ and T is given in equations 1 and 2. This relationship would be applied as far as possible for various desired spectral power distributions, such as are employed in standard brightness, TAPPI Opacity, and the various spectral functions associated with color measurement.

$$a = (1 + R_o^2 - T^2)/R_o \quad (1)$$

$$R_{oo} = (a/2) - \sqrt{(a/2)^2 - 1} \quad (2)$$

Where the $R_{oo}$ values are determined with appropriate filters, the tristimulus values (Illuminant C) can be calculated as shown.

$$X(\text{blue}) = 0.1973 \, R_{oo} \quad (3)$$

$$X(\text{red}) = 0.7831 \, R_{oo} \quad (4)$$

$$X = X(\text{red}) + X(\text{blue}) \quad (5)$$

$$Y = R_{oo} \quad (6)$$

$$Z = 1.1812 \, R_{oo} \quad (7)$$

TAPPI Opacity can be calculated using equations 8 and 9 where R' is equal to 0.89.

$$R_R' = R_o + R'T^2/1 - R_oR' \quad (8)$$

$$C_{0.89} = 100 \, R_o/R_R' \quad (9)$$

Although it has often been demonstrated that the "balance of energy" equations and the Kubelka-Munk theory are very useful in interrelating the optical properties of paper determined under many different conditions of geometry and spectral power distributions, it is important to recall that some of the conditions required by theory are not met in practice. Among these, the specimen should be illuminated and viewed with diffuse light, monochromatic light should be employed and the optical properties of the material should conform to the requirement that the absorption and scattering of light be independent of each other and occur at numerous discrete sites spaced randomly throughout the substance. All reflectance and transmittance values should be determined on the absolute basis. The fact that these conditions are seldom met requires experimental testing of the theory for each intended use.

Experimental data were acquired to test the validity of this use of the theory for a number of "white" as well as more strongly colored papers. The extent of agreement which might be expected between the calculated reflectivity, $R_{oo}$, using equations 1 and 2 and experimentally determined $R_o$ and T values, and actually measured $R_{oo}$ values was examined for two different optical systems. Neither system would likely be used in making optical measurements on moving webs, but both serve the purpose of testing the relationships in actual use situations.

In the first set of experiments, handsheets were prepared from bleached hardwood pulp, refined to 450 ml C.S.F., at basis weights of 32, 64, 96 and 127 g/m². The optical properties of these samples were determined using the General Electric Recording Spectrophotometer with "reversed" optics (GERS-RF). The specimen was illuminated diffusely with the spectral power distribution of a tungsten filament source modified by the integrating cavity lining. Viewing of the specimen was at 6° to the normal. Four filters were interposed separately in the reflected beam to give the spectral response for the overall system of the $E_c\bar{x}$, $E_c\bar{y}$ and the $E_c\bar{z}$ functions of the CIE system. Two filters were utilized to obtain the $E_c\bar{x}$ function. The $R_{oo}$ values, calculated from the measured $R_o$ and T values using equations 1 and 2, are compared with the $R_{oo}$ values measured directly with the GERS-RF. The data given in Table 1 are averages for five different specimens at each basis weight.

The calculated and measured tristimulus values are in good agreement for the white and blue bond paper with rather poor agreement for the pink bond paper. The color differences based on the differences in the calculated and measured tristimulus values are given in Table IV.

Table IV

Color Differences ($\Delta E$) Related to the Differences Between the Calculated and Measured Tristimulus Values for Five Commercial Papers

| Commercial Papers | $\Delta E$ |
|---|---|
| White Bond | 0.6 |
| Tracing Paper | 1.6 |
| Pink Bond | 8.9 |
| Coated Paper | 2.1 |
| Blue Bond | 0.9 |

Where the color differences are very large, it is probably attributable to the broad bandwidth of the spectral functions used to determine the tristimulus values and the substantial changes in reflectance with wavelength for the more highly colored papers. This can lead to error in the calculation of $R_{oo}$ from $R_o$ and T. Such error would likely be eliminated if a reflectivity ($R_{oo}$) curve were first calculated from the curves for $R_o$ and T (appropriate number of points should be used to give an accurate $R_{oo}$ curve) before the integration leading to the tristimulus values is performed. But, of course, this is not the means by which data are likely to be obtained and treated in an on-machine color measurement system, at least at present. The results indicate that, for many papers, the theoretical relationships will give excellent estimates of $R_{oo}$ from $R_o$ and T acquired for single sheets. Where the discrepancies are greater than desirable, it is probable that useful empirical relationships may be established.

The estimation of $R_{oo}$ from measurements of black body backed reflectance and transmittance of single sheets using theoretical relationships is subject to less error than are estimates obtained using two reflectances obtained with different backing reflectances, for example. A further approach to the design of on-machine color measuring instrumentation involves reflectances determined on single sheets backed by a body having a selected reflectance. Obviously, such reflectances will be equal to $R_{oo}$ for any paper only if the effective reflectance of the backing is also equal to $R_{oo}$ for that paper. Also, the backing will not ordinarily have the color of the paper. Hence, recourse must be made to empirical relationships between the measured reflectance values and the color of the samples as would be determined directly using opaque pads. Further, since it is often desirable to employ a spacing of some magnitude between the moving web and the backing surface, variations in the spacing which would likely occur in practice would be another source of discrepancy.

The following experiments were conducted to explore the differences in the color of paper when backed by a translucent opal glass and an opaque, enameled plaque. The spectral reflectivity curves for both backings was determined with the GERS and are given in FIG. 1. It should be noted that these reflectivity curves cannot be used to determine the effective reflectances of the backings when employed against paper and, particularly for the translucent opal glass would be at different levels if determined with different geometry. Reflectance data on the paper specimens were obtained with both GERS-RF and with the Automatic Color-Brightness Tester (ACBT). The latter employs 45° illumination and normal viewing. Both instruments were equipped with appropriate filters so that the tristimulus values could be determined from four reflectance measurements (Illuminant C). Six commercial papers were evaluated with the white body backings at different spacings from the sheet.

WEB FACTORS WHICH INFLUENCE THE MEASUREMENT OF OPTICAL PROPERTIES

Basis Weight and Sheet Formation Variability

Basis weight variability, of which sheet formation represents a rapidly varying form, is a matter of interest in the on-machine measurement of optical properties. All optical properties are basis weight dependent in some degree. The dependence may arise because of changes in sheet structure with basis weight or may be a consequence of the simple change in mass per unit area for constant sheet structure. Thus, whereas the reflectance of a thick pad of paper may prove to be relatively independent of basis weight, the reflectance of a single sheet with black body or other designated backing and transmittance are expected to show basis weight effects. If the basis weight is known, it is possible to apply first-approximation corrections for departures in basis weight from a target value. However, such corrections would be different for different papers, would need to be developed experimentally and would best be applied to the longer-range basis weight variations.

Rapid changes in basis weight on the scale involved in sheet formation effects will result in rapidly changing optical properties as the moving sheet is scanned by an instrument in fixed position. The true time-varying signal might well be averaged by the on-machine instrument unlike the arithmetic averaging of the same optical property values determined statically off-machine. Whether the two averages are significantly different would depend both on the nature of the time-varying signal and the time-response characteristics of the on-machine instrument.

Where two optical measurements are made simultaneously at one position on a moving web, each would be averaged instrumentally. Values of $R_{oo}$ calculated from such averages may differ from an average of $R_{oo}$ values calculated from various pairs of optical values (for example, $R_o$ and T). Though such an error would be small for small basis weight variations, it could be of importance for some papers.

If sets of data are acquired on moving webs by interposing different filters in time sequence, for example, the particular values within a set would be obtained on different areas of the web and each could relate to a slightly different basis weight. Obviously if such values are affected by basis weight, the optical property described by the set (color, for example) would be in error if the basis weight were not constant. One could in such an instance, resort to the repetitive collection of sets of values with an averaging of the art results over a longer time period. It would be desirable to avoid the collection of data such that any particular value within a set is always obtained at the same unique web position or time cycle.

Fiber Orientation

Machine-made papers usually have some degree of fiber orientation which causes a difference in reflectance if the sheet is illuminated in the "in-machine" or "across-machine" direction. Generally, the reflectance is lower when the specimen is illuminated in the "in machine" direction. Fiber orientation is usually less pronounced on the felt side; hence, optical data are usually obtained on that side. Standard brightness is measured on the felt side and the "in-machine" direction. On-machine measurements can of course, be performed in the same way.

Polarization of light occurs to some extent when a paper surface is illuminated at an angle such as 45° and the extent of polarization depends upon the kind of surface and to some degree upon fiber orientation. For this reason, the on-machine instrumentation should have the same response to polarized light as the off-machine instrument.

Two-Sidedness

Most papers have different spectral reflectivities for the felt and wire sides with the effect being more pronounced for very light basis weights and for coated papers. This affects the relationship between $R_o$, T and $R_{oo}$ causing an error in the calculation of $R_\infty$. This effect is not large if the measurements of $R_o$, T, and $R_{oo}$ are all made with the same side of the sheet facing the light beam on the on-machine as well as the off-machine instrument.

Moisture Content

In on-machine testing of paper, the moisture content may be at a level different from that employed in off-machine testing. Also, the intensity of the light incident on the specimen in some off-machine colorimeters is of a sufficiently high level to cause an appreciable change in temperature moisture content of the specimen during the course of performing a reflectance measurement.

Reflectance data have been obtained for "white" and dyed paper samples using the GERS and ACBT, as these instruments employ a very low level of illumination thus minimizing departure from established laboratory environmental conditions. The GERS employs 6°-diffuse geometry with the specular component partially included and the ACBT employs 45 −0° geometry with the specular component excluded. Using both systems, one should be able to deduce if the change in reflectance of the specimen is due to changes in absorption, scattering, or surface structure. Changes in absorption and scattering would influence the data from both instruments in about the same way whereas changes in the specimen surface would influence the data differently. Changes in absorption could be more pronounced in selected portions of the spectrum whereas changes in scattering or surface should have a minor dependence on wavelength.

In the case of the GERS, air at different levels of relative humidity was passed through the integrating cavity. Thus, the area of the specimen measured by the instrument was exposed to the conditions air while the measurement was being performed. The same was true for the ACBT except that the air was passed through the cylindrical opening in the instrument directly beneath the specimen opening.

The data show small changes for the "white" papers while the dyed papers and the newsprint show more significant changes. The effects were generally greater with the ACBT than with the GERS suggesting that changes in surface characteristics with changing relative humidity is principally involved. It is interesting to note that the reflectance of the red paper increased at 450 nm with increasing moisture content and decreased at 550 and 500 nm. This effect was noted with both instrument and is probably attributable to changes in light absorption.

Colorimetric data obtained with the ACBT at the several levels of relative humidity are given in Table XIII. The E value represents the color difference between the first determination at 5% relative humidity and the subsequent results. Several samples show a E value greater than one with sample H over two.

Sample A (fluorescent) has a reflectance of 85.0% for the GERS at 400 nm and 55.8 for the ACBT. This large difference is related to the erroneous evaluation of the fluorescent component by the GERS.

It appears that reflectance of paper, especially dyed papers, is significantly affected by changes in moisture content. Indications for the samples tested are that changes in moisture content resulting from exposure to levels of relative humidity from 5 to 50% represent a reasonable limiting range for good accuracy.

Temperature

The web temperature would be higher for on-machine than off-machine testing. A study was performed to determine the effects of changing temperature on the reflectance of paper. The same paper samples (different specimens) evaluated in the moisture study were evaluated at four different temperatures. The GERS and the ACBT were employed because of their low level of illumination. Temperature at the surface of the specimen in the area exposed to the incident beam was determined with a 0.004-inch diameter wire chromel-alumel thermocouple. The junction was placed in contact with the paper surface. It is understood that differences in the absorption characteristics of the thermocouple and paper preclude the assumption that the paper surface and the junction temperature are the same when exposed to the incident radiation. However, when the temperature measurements were made, paper sample B was placed over the specimen opening in every case so that the relationship between junction and paper temperature should be fairly consistent for the different instruments.

A reasonable upper limit on temperature, as indicated by these data would be about 40° C. If on-machine measurements are made at higher temperatures, the potential effects of temperature may need to be considered for comparison with off-machine optical data.

Fluorescence

Widespread use of fluorescent dyes has made the matter of fluorescence an important factor in the measurement of optical properties of paper. The fluorescent "whitening" agents used in the paper industry generally absorb strongly in the violet and ultraviolet regions of the spectrum and emit light at somewhat longer wavelengths in the violet and in the blue regions of the spectrum. For fluorescent dyes, in general, the region of absorption may extend from the short wavelengths (ultraviolet) to the region where light is emitted by the dye. Actually, there may be some overlapping of the absorption and emittance regions.

In the case of the fluorescent "whitening" agents, the ultraviolet light needed to excite dye is largely absorbed in the surface layers of the sheet. Thus, with fluorescence present, reflectance would be most influenced whereas transmittance would be only minimally affected. This has a pronounced effect on the calculation of $R_{oo}$ from $R_o$ and T.

Properly designed instrumentation should be employed where fluorescence is a factor (19).

WEB POSITION

In all optical instruments, the position of the web must be fixed at the appropriate design point. In the calibration of an instrument with paper or other material, a web position will be indicated. The moving web should, of course, be at the calibration position. This is best accomplished by ensuring that the web is in contact with a reference surface. Through establishing such contact, it is possible to have the optical instrumentation on one side of the web properly placed with respect to web position. The other side, however, must be maintained at the proper spacing. Changes in instrument to web distance can introduce errors of significant magnitude. Two options are available; the apparatus to web spacing may be fixed, or the spacing may be measured and corrections of the results made for changes from the desired spacing. The former method is preferred whenever possible.

Web flutter is obviously undesirable. If web flutter, exists web position is not known. Similarly, vibration of the optical apparatus may influence the results.

Web Speed

Potential effects due to web speed depend on the nature of the time constants of the optical instruments. For a time varying signal, with linear photometric response of the instrument, and with slow response, an appropriate arithmetic average value might be expected. However, if the time varying signal is not symmetrical about the mean value, the instrument may not indicate the mean correctly whereas the off-machine instrument could. Thus, the reading could be speed dependent under some conditions of sheet variability and instrument design.

Calendering

All optical properties of paper are affected by calendering of the sheet. Hence, on-line measurements of final paper properties must be made after calendering. In the usual application of optical apparatus between the calender and the reel, the measurements would be obtained only a fraction of a second after the sheet leaves the calender. It seems likely that the sheet would be undergoing compression recovery during this period and for some time after calendering with the result that changes in the sheet thickness and surface smoothness would occur between the time the on-line optical measurements are and some later time when off-machine optical measurements are made. The possible importance of such effects is not known. The fact that they may occur is recognized as one of the possible factors leading to lack of agreement between on-line and off-machine measured optical properties.

Stray Light

It is usually possible to design optical instrumentation with proper shielding from stray light. Obviously, such shielding is required, since appreciable error may occur if stray light is permitted to enter the measurement zone.

Dust and Dirt

All on-machine optical instrumentation should be designed to eliminate or minimize dust or dirt accumulations. Some contamination cannot be avoided and compensation for its effect must be developed through frequent calibration of the on-machine apparatus.

Instrument Temperature

The optical as well as electronic components of optical devices are temperature sensitive. Best design involves control of instrument temperature to values above the ambient temperature of the machine room with the web in running position. Compensation for temperature is also possible, but less desirable.

LITERATURE CITED

1. Van der Akker, J. A., Nolan, Phillip, and Wink, W. A., The Physical Basis of Standardization of Brightness Measurement, Paper Trade Journal, 114, No. 5: 34–40 Jan. 29, 1942).
2. Van den Akker, J. A., Dearth, L. R. and Shillcox, W. M., Evaluation of Absolute Reflectance for Standardization Purposes, J. Opt. Soc. Am., Vol. 56, No. 2, 250–252, February 1966. D. G. Goebel, B. P. Caldwell and H. K. Hammond, III, Use of an Auxiliary Sphere with a Spectrophotometer to Obtain Absolute Reflectance, J. Opt. Soc. Am., 56, 783 (1966).
3. Van der Akker, J. A., Standard Brightness, Color and Spectrophotometry with Emphasis on Recent Information, Tappi Vol. 48, No. 12 (December, 1965).
4. Report No. 8 of the American Paper and Pulp Association. Parts I and II. Adaptability of the G.E. Reflection Meter as a Color Analyzer. Part III. The Effect of Infrared Fluorescence Radiation upon "Brightness" Measurements obtained with the G.E. Reflection Meter. Instrumentation Studies XIII. Paper Trade Journal 104, No. 18:47–53; No. 19:51–63; No. 20:45–49 (May 6, 13, 20, 1937).
5. Hofert, H. J. and Loff, H., Calibration of the Photometric Scale of a Reflectance Photometer, Zeitschrift fur Instrumentenkunde, Bol. 72 (1964) No. 5.
6. Davis, M. N., A simple and Reliable Photo-Opacity Tester, Tech. Assoc. (TAPPI) Papers, Ser. 16, 16,277 (1933).

7. Hardy, A. C., Handbook of Colorimetry, The Technology Press, Massachusetts Institute of Technology, Cambridge, Mass. (1936).
8. Report No. 22TO: American Paper Institute Instrumentation Program, Part VI. Comparison of TAPPI and Printing Opacity Determined with Five Instruments, May 8, 1971.
9. Stokes, G.G. On the Intensity of the Light Reflected from or Transmitted through a Pile of Plates. Proc. Roy. Soc. London, 11, 545 (1860–1862).
10. Kubelka, P., and Munk, F., A. Tech. Physik 12:593–601 (1931).
11. Kubelka, P., New Contributions to the Optics of Intensely Light-Scattering Materials. JOSA, Vol. 38, No. 5 (May, 1948); errata, ibid, 38, 1067 (1948); ibid, 44, 330 (1954).
12. Van der Akker, J.A., Tappi 32, No. 11:498–501 (November, 1949).
13. Reflectance-Opacity Chart for White Backing of 0.89. (Judd, 1937).
14. Van der Akker, J.A., Tappi 50, No. 5:41A (*May*, 1967).
15. Officical Recommendations of the International Commission on Illumination Publication CIE No. 15 (E-1.3.1) 1971.
16. Van der Akker, J.A., Chromaticity Limitations of the Best Physically Realizable Three-Filter Photoelectric Colorimeter. J. Opt. Soc. Am. 27, No. 12:401–407 (December, 1937).
17. McAdam, David L. "Color Measurement and Tolerances." Official Digest (Federation of Societies for Paint Technology). 37, 1487–1531 (1965). Chickering, JOSA, 57, 537 (1967).
18. Van der Akker, J.A. A Mechanical Integrator for Evaluating the Integral of the Product of Two Functions and its Application to the Computation of I.C.I. Color Specifications from Spectrophotometric Curves. J. Opt. Soc. Am. 29, No. 9:364–369 (September, 1939).
19 Grum, F. Instrumentation in Fluorescence Measurement, Journal of Color and Appearance, Vol. 1, No. 5:18–27 (April/May, 1972).

DISCUSSION OF THE CLAIMED SUBJECT MATTER

A basic conception of the present disclosure is crucially concerned with the art of paper manufacture wherein numerous grades and weights of paper are to be manufactured, and wherein access to the paper web for measurement of paper optical properties during the manufacturing process is restricted to a section between the calendering stack and the reel. The environment at this location has been detailed in the preceding section. By measuring two essentially independent optical parameters, for example measuring both the reflectance and transmittance with respect to incident light of the necessary spectral distribution, it is possible to calculate paper optical properties on the basis of existing theory with an essential independence of basis weight. The feasibility and effectiveness of this approach is confirmed in the preceding section.

Closely related to the foregoing is the conception of utilizing as nearly as practicable the optical response characteristics and geometry of existing istruments used in the paper industry, so as to achieve as close a correlation as possible with present off-line measurements of color and brightness, for example. Also of substantial significance is the conception of providing a rugged and compact temperature-stabilized instrument capable of reliable and accurate on-machine measurement of color, brightness and opacity.

The reduction to practice of these basic conceptions has included several sponsored projects at the Institute of Paper Chemistry as reflected by the preceding section and has included laboratory testing of a prototype device for accuracy and reliability on a wide range of paper samples, with careful comparison being made with corresponding measurements using standard laboratory instruments. Details of the life testing of the prototype unit over a ten-month period and the adaption of the device to reliable and stable operation on the paper machine have been included herein to document the practical implementation of the present invention. Because of the critical need for rapid calculation of paper optical properties in an on-machine device, the necessary computer programming has been developed and is fully disclosed herein. In spite of the substantial investments which have been made to secure expert assistance in implementing the conceptions, a period of time of over two years has been required to reach the stage of reduction to practice disclosed herein.

An important aspect of the disclosure relates to the measurement of the basis weight of the moving paper web concurrently with the simultaneous measurement of reflectance and transmittance values for essentially a common region of the web. Using the calculated value of infinite reflectance $R_{oo}$ (including the grade correction factor) and the value of transmittance T, for example, for the same sample region, along with a concurrently obtained, average value for basis weight, essentially accurate values of scattering coefficient $s$ and the absorption coefficient $k$ are obtained. Such coefficients will exhibit essential independence of any variations in the basis weight of the paper sheet material under these circumstances.

The measurement of both a refelectance and a transmittance value for a common sample region has an advantage over the measurement of two reflectance parameters under conditions such as found in the paper manufacturing process since the transmittance measurement is relatively insensitive to misalignment or tilting of the optical axis 515 of the backing assembly or lower sensing head 12, FIG. 3, relative to the optical axis 15 of the sensing head 11. This advantage is especially important for sheet material of relatively high opacity where two reflectance paramters would tend to be relatively close in value.

Generally the results of laboratory tests dicussed herein are expected to be applicable to the on-line system. Thus the spread between values of $R_{oo}FC$ (See Table 3) obtained by the illustrated on-line system and the corresponding values of $AR_{oo}FC$ taken as standard should not differ by more than about plus or minus two points on a scale of zero to one hundred, prior to any grade correction, for a wide range of paper sheet materials of different color and basis weight.

The samples for which such accuracy was obtained in the laboratory included a range of basis weights of from 60 grams per square meter to 178 grams per square meter for white paper. Without the use of a correction factor, calculated $R_{oo}$ values which fell within two points of the measured value included samples of paper colored white (several tints), green, blue, canary, russett, ivory, gray and buff. Colors including pink, gold, salmon, and cherry required a significant correction factor for the $X_R$, $Y_C$, and $Y_A$ functions. All of the calculated $R_{oo}$ values involving the $X_B$ and Z functions fell within 0.77 units of the measured value on a scale of zero to 100, again without the use of any correction factor and regardless of color or basis weight.

DISCUSSION OF THE CLAIMED SUBJECT MATTER

The term quantitative measure of paper optical properties as used in the claims refers to output quantities of a numerical nature such as supplied by the on-line digital computer system 996, FIG. 6, programmed as explained herein with reference to FIGS. 7–20. Examples of such quantities are those indicated in block 990, FIG. 20; these quantities are identified with the corresponding conventional paper optical properties in Table 21.

The term on-machine optical monitoring device is intended generically and refers to the device 10, FIGS. 1 and 2, and other comparable devices for sensing two essentially independent optical response parameters such that a paper optical property is characterized prior to use of any correction factors with substantially improved accuracy in comparison to any characterization (prior to correction factors) of such paper optical property from either of such optical response parameters taken by itself. Such a monitoring device may be used as an aid to manual control of the paper making process or may be used as part of a closed loop automatic control system. Thus "monitoring" does not exclude active control in response to the output signals from the monitoring device.

Within the scope of the present subject matter, one or more of the following paper optical properties may be sensed: brightness, color, flurorescence, and/or opacity. Control of brightness and fluorescence offers a very substantial potential for cost reduction in the production of a significant range of paper types. Color control, on the other hand, may have important consequences regarding flexiblity of manufacture, product uniformity, and grade change flexibility.

The value of on-line opacity control has already been demonstrated to a large degree in a prior closed loop analog opacity controller. In this installation, the average opactiy across the web is controlled almost exactly at any given desired value. In previous manually controlled operations, the PKT (Pigmentary Potassium Titamate, $K_2O\text{-}6T_iO_2$ by du Pont) flow was set to some value chosen by the beater engineer and usually held to such value for the duration of the run of a given grade and weight. In the meantime, the paper opacity varied up and down, depending on process conditions at the time. Since the installation of the analog opacity controller, the opacity set point is adjusted rather than the PKT flow, thus holding opacity constant at the desired level. Instead of opacity, the PKT flow now varies up and down to compensate for other presently unavoidable process upsets resulting from variations in broke richness, PKT solids, dye usage, save-all efficiency, and other machine retention conditions. For a complete discussion of the installation of the analog opacity controller, reference is made to F.P. Lodzinski article "Experience With a Transmittance-Type On-Line Opacimeter for Monitoring and Controlling Opacity," Tappi, The Journal of The Technical Association of The Pulp and Paper Industry, Vol 56, No. 2, Feb. 1973. This article of February, 1973 is incorporated herein by reference.

Existing on-line color meters have two serious disadvantages as follows:

1. Each measures a reflectance value ($R_g$) which is decidedly different from that necessary for actual color and brightness characterizations. Off-line instruments, which adequately measure these properties, require that a pad of several thicknesses ($R_{oo}$) of the same paper be exposed to the light source aperture. Obviously, this is impossible with an on-line instrument, unless the far more inaccessible reel itself is tested. The use of $R_g$ instead of $R_{oo}$ requires very frequent off-line testing, and constant updating of an empirical calibration procedure to maintain adequate accuracy. A separate set of calibration parameters for each grade and weight is also required. Only in instances of extremely high opacity such as heavily coated, or heavily dyed colors where $R_g$ approaches $R_{oo}$, can the above problems be minimized to the point where accuracy becomes sufficient for control purposes.

2. Existing color instruments are not equipped to measure transmitted light which is much more sensitive to differences and, so far, the only commercially proven method for the continuous monitoring of opacity.

To assist in indicating the scope of the present disclosure, the substance of excerpts from an early conception record with respect to the present subject matter are set forth in following paragraphs, headed "Proposal" and "Porposed Instrument Design" having reference to the defects of existing on-line color meters just discussed:

Proposal:

An instrument built to the general specifications disclosed in the following section headed "Proposed Instrument Design" avoids the above described defects and, at the same time, provides for a concise, but extremely versatile, nearly total optical property monitor and controller. Highly trained specialists in all fields required here, including paper optics, color theory, photometry, computers, and others, if needed are available. As an example, exact specifications for the filters, photocells, and light sources are essentially ready for manufacture now. Such specialists are also aware of factors important to optical characterization frequently ignored by commercial producers of optical instruments.

PROPOSED INSTRUMENT DESIGN:

An instrument made up of two scanning sensing heads, one above and one below the moving paper web, and a dedicated computer with appropriate couplers for input and output, is envisioned. The bottom head would receive light transmitted through the sheet and subsequently analyzed for its X, Y, and Z tristimulus components. It would also contain a backing of some specified effective reflectance (possibly a black body of zero, or near zero, reflectance) located just ahead or behind (machine direction) of the transmitted light receptor compartments (s).

The upper head could contain the light source, as well as a reflected light receptor. The latter occurs after reflection from the moving web at a point just above the backing, on the bottom head and would also be analyzed for its X, Y, and Z tristimulus components. Both light receivers and, for that matter, the light source itself could be integrating cavities of a type. This would be one way to insure the uniform distribution of emitted, transmitted, and reflected light in the X-direction in addition to providing identical samples of light going to each photoelectric cell installed with filters within the cavities themselves. Thermostatically controlled heaters or coolers would likely be desirable for temperature control. The flux of the light source could be monitored or controlled by a third partial, or full, set of filter-photocell combinations The availability of both the transmitted (T) and reflected ($R_g$) light signals described above allows for precise computation of the reflectance with an infinite backing ($R_{\infty}$). It is the latter, $R_{\infty}$, value, which is required to characterize color, brightness, and an index of fluorescence. In addition, it would eliminate the need for any grade corrections in measuring either printing or TAPPI opacity, both of which could be made available if desired.

A small, rather low-cost, dedicated computer with appropriate interface equipment, could be used to receive all signals, compute all pertinent optical properties, and determine the signal for direct, closed loop control of:
  a. 2–5 separeate conventional dye additions;
  b. fluorescent dye feed to the size press; and
  c. PKT, $TiO_2$, or other slurry flow;
so that brightness, opacity, color (L, a, b) and fluorescence could be maintained almost exactly as chosen by, perhaps even a master computer, if desired.

Kubelka-Munk equations, quantitative color descriptions, and their inter-relationships, recently acquired wet end mathematical models, along with existing control theory, are all presently available in some form or other to convert the input signals from the scanning heads to optical measurements and flow feeds with which paper manufacturers are familiar. The combined mathematical technology above is also sufficient for adequate decoupling of this otherwise complicated information so that overlapped control is avoided.

Use of a dedicated computer would eliminate most of the electronics now associated with optical measuring equiment. It could also be used to integrate results across the web and simplify and/or maintain calibration. The package would lend itself to rather universal application and minimize the time and effort on the part of the purchaser.

The key feature of this proposed instrument, which distinguishes it from existing on-line optical testers, is that it calls for the measurement of both transmitted and reflected light without undue complications. This, in turn, can cause a great deal of improvements regarding sensitivity, accuracy, flexibility, and thoroughness of a continuous optical property measuring device.

The following Table will serve to identify the computer symbols used in FIGS. 17–20 with the corresponding conventional symbols and terminology sued in the text.

Table 21

| Identification of Computer Symbols Used in FIGS. 17–20 | | |
|---|---|---|
| Computer Symbol | Conventional Symbol | Conventional Term for Symbol |
| SGCF | GC(Table 3) | specific grade correction factor |
| RG | RD(Table 3) | Nominal reflectance of the diffuser window 135 |
| TD | $T_d$ | Nominal transmittance of the diffuser window 135 |
| RZERO (RZTABL) | $R_0$(Table 3) | reflectance with black body backing for each filter wheel position I equals zero through five. |
| T (TTABL) | T(Table 3) | Transmittance with black body backing for each filter wheel position I equals zero through five. |
| RINF (RITABL) | $R_{\infty}$ (Table 3) | infinite backing reflectance for filter wheel positions I equals zero to five. |
| S (STABL) | S | scatter coefficient for each filter wheel position I equals zero through five. |
| K (KTABL) | K | absorption coefficient for each filter wheel position I equals zero through five. |
| ZFLUOR | — | fluorescent contribution to tristimulus Z reflectance |
| ZRINF | — | tristimulus Z infinite backing reflectance with fluorescence |
| XBRINF | — | tristimulus $X_B$ infinite backing reflectance with fluorescence |
| BRRINF | — | TAPPI brightness (see Table I in the first section of this Topic for spectral distribution of the first filter wheel position) |
| POPAC | $R_0/R_{\infty}$ | printing opacity |
| YAR89 | $R_0.89$ | tristimulus Y reflectance with .89 backing |
| TOPAC | $R_0/R_0.89$ | TAPPI opacity |
| XTRI | X | C.I.E. tristimulus coordinate X |
| YTRI | Y | C.I.E. tristimulus coordinate Y |
| ZTRI | Z | C.I.E. tristimulus coordinate Z |
| LH | L | Hunter coordinate L |
| AH, BH | a,b | Hunter coordinates a, b. |

SCOPE OF THE EARLY CONCEPTION OF THIS INVENTION

Given the foregoing conception, it is considered that many modifications and variations will be apparent to those skilled in the art. The basic conception claimed herein is the sensing of two essentially independent optical response parameters of a single thickness relatively homogeneous sheet material such that any other desired parameter or paper optical property can be accurately calculated.

For the case of opacity measurement, for example, the present invention is particularly applicable to an optical system wherein system spectral response essentially simulates the C.I.E. tristimulus Y filter with either illuminant A or C and to near-white papers as explained in the Lodzinski Article of February, 1973 incorporated herein by reference.

DISCUSSION OF FURTHER OR ANTICIPATED MODIFICATIONS AND FURTHER INFORMATION RELATIVE TO THE PREFERRED EMBODIMENT

Changes Made to the On-machine System of FIGS. 1–6.

1. Light source lamp terminals were connected to test tip jacks so that lamp voltage (at the lamp) can now be quickly measured without opening the case.

2. An easily removable doorway was cut from the top of the upper head case so that the photocell and amplifier gain circuits are much more accessible now. The photocell can now be easily removed and its 3/16 inch diameter aperture viewed directly from above without removing the case. This permits a quick check to see whether the two heads are properly aligned. The diffuser 276, FIG. 3, in the photocell aperture will be uniformly lighted when alignment is correct. Non-uniform illumination of this diffuser is quite apparent when the heads are improperly aligned.

3. A temperature sensitive resistor is located in the upper head adjacent to the photocell. Conductors are connected to lugs on the power supply panel so that such resistance measurements are easy to acquire. An empirically prepared chart is used to convert the resistance to temperature. Thus, an upper head temperature can be monitored from the remote power supply panel. (This temperature measuring device has been on the OMOD since it was first constructed.)

4. The upper head weighs 20 lbs. and the lower head 9 ¾ lbs. The weight of the mounting brackets are 7 and 5 lbs., respectively. (The compact size and light weight of these heads is an important advantage when it comes to providing means of installing and traversing across the web).

5. The reason we choose the 45°–0° geometry is because this geometry is used in the standard TAPPI brightness measurement. There is no standard TAPPI color test geometry at this time. It is considered that the 45°–0° geometry with the light plane in the machine direction is the proper geometry for color measurement as well. The reason for this is that most of our paper products where brightness and color are important are eventually used for written communications purposes. Consequently, they are viewed on a table top or desk with the human eye and light source approximating the 45°–0° geometry as employed in the OMOD. Moreover, the grain direction of the paper (grain long 8 ½ × 11 letterhead for example) is such that this directional effect is also simulated by the OMOD. Diffuse viewing is impossible by the human eye and diffuse illumination is quite unlikely in most offices or places of paper use.

ANTICIPATED COMPUTER PROGRAM CHANGES

1. We plan to test each individual reading of transmittance and reflectance (T and R) and compare it to the previously smoothed values. The latest individual readings will not be used to update the smoothed average whenever a difference between the two is greater than X %. The value of X will remain flexible, but likely in the neighborhood of 5–10 %. This subprogram will reject and flag bad data since the paper optical properties could hardly change faster than this between readings. An exception is the very beginning of a run; however, the heads are not put on sheet until the operation has settled down somewhat anyway. Only the startup of a run will need to be manual or feed forward as far as color, brightness, and opacity control is concerned.

2. Initialization of the smoothing algorithm of R and T will be made to occur only when a grade change occurs; i.e., whenever a new set of specific grade correction factors are entered into the computer memory. There should not be any need for re-initialization for any other reason. Even basis weight changes occur gradually enough to permit the use of the previously stored smoothed averages without serious difficulty. We may, however, consider the use of an operator command to re-initialize such algorithms if found desirable.

3. For the No. 6 paper machine (shown in FIGS. 1 and 2), the OMOD heads will be pushed completely off the web on the front side to allow the basis weight gauge (mounted side of the OMOD) to measure right up to the front edge. The program will, therefore, need to be modified to reject data acquired whenever this occurs. Since the head position will be known, from the basis weight profile monitoring system, such data can be left unused wherever the position Y or greater is reached.

It turns out that this particular situation provides a convenient means of servicing the OMOD. The traversing mechanism can be stopped when the OMOD heads are pushed beyond the web edge where they are quite acessible for examination, checking of standardization, etc.

CURRENT PROGRAM LISTING

GE-PAC 4020 Program Listing Characteristics

The following program listings are considered to be in conformity with the flow charts of FIGS. 8–20. The listing is provided by the General Electric PAC 4020 process control computer, and the following general discussion explains the GE-PAC 4020 program listing characteristics.

I. The first page contains the following unique information:
  A. Line 1-control statement, with time of day and activity.
  B. Lines 2 and 3 contain program identification numbers.
II. The remaining information is broken into three parts as follows:
  A. The three left-most columns of numbers consist of assembler-generated machine coding:
    1. The first column of numbers consists of the octal location, relative to the beginning of the program.

2. The second column of numbers consists of the contents of the octal location in absolute form--the first two numbers signify the operation code; the third number signifies the index register, if any; and the remaining five numbers signify the absolute operand of the instruction.
3. The third column of numbers consists of the contents of the octal location in relative form---it is identical to (2), except the five right-most numbers signify the relative operand from the location of the instruction.

B. The next eighty columns correspond to the symbolic instructions from which the assembler generated the machine coding.
1. Statements beginning with an asterisk or C are comments only, with respectively a 6 or 7 in column seventy.
2. Other statements are divided as follows: label, if any; symbolic operation code; symbolic operand, if any; index register preceded by a comma, if any; comment, if any; and 6, 7 or 1 in column seventy.
3. The 6 in column seventy indicates a programmer-defined assembly language statement. The 7 in column seventy indicates a programmer-defined Fortran language statement. The 1 in column seventy indicates an assembler-defined assembly language statement, such as symbolic coding generated from a programmer-defined Fortran statement.

c. The right-most column contains the line sequence number of the printout.

PROGRAM LISTING FOR PROGRAM FOURTEEN (FIGS. 8–16)

The following listing is presented to illustrate the extent of the programming effort to implement the flow charts of FIGS. 8–16. It will be observed that the implementation of these flow charts together with the changes previously indicated herein and any necessary debugging is within the routine skill of the art.

```
101014  COMPILE
        814030060   814030060              IDN 000000                                                              1
        814030060   814030060                                                                                      1
                                            CTABL  EQL 12                                                          6
                                            STTABL EQL 28                                                          6
                                            RGTABL EQL 44                                                          6
                                            VTABL  EQL 60                                                          6
                                            SGTABL EQL 76                                                          6
                                            OUTABL EQL 92                                                          6
                                            STABL  EQL 102                                                         6
                                            KTABL  EQL 110                                                         6
                                            RSTABL EQL 118                                                         6
                                            MPAR   EQL 134                                                         6

*PROG 14                                                                6

*TURNED ON INITALLY BY TYPER-THEREAFTER ON 1 SEC. BY AUXTIMER =5         6
000000   00002100    00002100              E014  LDA TIME                                                          6
000001   32002707    32002707                    STA AUXTM+3                                                       6

*LOAD FILEX STARTING ADDR, INTO INDEX REGISTER                          6
000002   16300414    16340412              EVERYL LDX FILEX,3                                                      6

*LOAD PCW ADD OF LOOPS P+Q FROM P.F., X4>P REFLECT.CELL X5>Q TRANS.      6
000003   00300001    00300001                    LDA 1,3                                                           6
000004   32000004    32000004                    STA 4            P                                                6
000005   00300002    00300002                    LDA 2,3                                                           6
000006   32000005    32000005                    STA 5            Q                                                6

*LOAD PCW:S OF LOOPS P+Q + CHECK IF OFF SCAN                            6
000007   00400000    00400000                    LDA 0,4          P                                                6
000010   05004727    05004727                    TOD 23                                                            6
000011   30000647    30040636                    BTR TRNOFF                                                        6
000012   00500000    00500000                    LDA 0,5                                                           6
000013   05004727    05004727                    TOD 23                                                            6
000014   30000647    30040633                    BTR TRNOFF                                                        6

*SET UP AUXTIMER TO RE-RUN IN 1 SECOND                                  6
000015   25030000    25030000                    IAI                                                               6
000016   00002707    00002707                    LDA AUXTM+3                                                       6
000017   11000406    11040367                    ADD DLYTIM                                                        6
000020   32002707    32002707                    STA AUXTM+3                                                       6
000021   25020000    25020000                    PAI                                                               6

*LOAD SLOWDOWN CTR.FROM X3 DECRIMENT IT BY ONE                          6
000022   00300004    00300004                    LDA 4,3                                                           6
000023   31002025    31002025                    SUB ONE                                                           6
000024   66000027    66040003                    BZE RESTOR                                                        6

*STORE NEW COUNT BACK IN FILE X + RTN.TO RTMOS                          6

000025   32300004    32300004                    STA 4,3                                                           6
000026   14000375    14040347                    BRU RTNRTM                                                        6

*RESTORE                                                                6

*RESTOR SLOWDOWN COUNT TO INITAL VALUE                                  6
000027   00300005    00300005              RESTOR LDA 5,3                                                          6
000030   32300004    32300004                    STA 4,3                                                           6
```

```
                              *READ FILTER POSITION INDEX FROM FILE + INDEX BY 1      6
000031   00300006    00300006          LDA 6,3                                        6
000032   60000001    60000001          AKA 1                                          6
000033   32300006    32300006          STA 6,3                                        6

*IS INC >OR LESS THAN 6                                 6
000034   50000007    50000007          SKA 7                                          6
000035   05004727    05004727          TOD 23                                         6
000036   34000066    34040030          BTS LDDIDG              YES                    6

*SET LOST INDEX REFERENCE TEMP FLAG                     6
000037   40000001    40000001          LDK 1                                          6
000040   32000413    32040353          STA LIRFLG                                     6

*OUTPUT AN ALARM FOR STUCK FILTER                       6

*TEST IF DISK IS DOWN                                   6
000041   00002777    00002777          LDA DISCOF                                     6
000042   05004700    05004700          TOD 0                                          6
000043   34000061    34040016          BTS NOALRM                                     6

*PRINT MSG.                                             6

PRINT 10                                       7
000044   40000051    40040005          LDK $10                                        1
000045   45004330    45004330          MAQ                                            1
000046   33000561    33000561          SPB $PRINT                                     1
000047   33000564    33000564          SPB $HLOUT                                     1

10 FORMAT ($ OMOD FILTER STUCK$)                  7
000050   14000061    14040011          BRU $M0                                        1
000051   40220000    40220000      $10 CON 0,40220000                                 1
000052   10047515    10047515          CON A,3, OM                                    1
000053   23642040    23642040          CON A,3,OD                                     1
000054   21444514    21444514          CON A,3,FIL                                    1
000055   25042522    25042522          CON A,3,TER                                    1
000056   10051524    10051524          CON A,3, ST                                    1
000057   25241513    25241513          CON A,3,UCK                                    1
000060   60077770    60077770          CON 0,60077770                                 1

000061   300000000   300000000     $M0 BSS 0                                          1
000061   16300414    16340333      NOALRM LDX FILEX,3                                 6

*REINITILIZE SMOOTHED DATA K>7                          6
000062   40000007    40000007          LDK 7                                          6
000063   32300011    32300011          STA 9,3                                        6

*SET UP CYCLE COUNTER FOR 1 DUMMY DATA SET              6
000064   40000001    40000001          LDK 1                                          6
000065   32300012    32300012          STA 10,3                                       6

*LOAD DIGITAL INPUT STATUS WORK FOR GROUP /1400         6
000066   25051400    25051400          LDDIDG IN /1400                                6

*IS FILTER IN POSITION ZERO!                            6
000067   05004726    05004726          TOD 22                                         6
000070   30000123    30040033          BTR LOSTIX                                     6

*I>7 !                                                  6
000071   00300006    00300006          LDA 6,3                                        6
000072   50000007    50000007          SKA 7                                          6
000073   05004727    05004727          TOD 23                                         6
000074   30000120    30040024          BTR REFILT                                     6

*REINITILIZE SMOOTHED DATA K>7                          6
000075   40000007    40000007          LDK 7                                          6
000076   32300011    32300011          STA 9,3                                        6

*SET UP DUMMY CYCLE >1                                  6
000077   40000001    40000001          LDK 1                                          6
000100   32300012    32300012          STA 10,3                                       6

*OUTPUT SKIPPED FILTER MSG                              6

PRINT 20                                       7
000101   40000106    40040005          LDK $20                                        1
000102   45004330    45004330          MAQ                                            1
000103   33000561    33000561          SPB $PRINT                                     1
000104   33000564    33000564          SPB $HLOUT                                     1

20 FORMAT ($ OMOD SKIPPED FILTER $)               7
000105   14000117    14040012          BRU $M1                                        1
000106   40250000    40250000      $20 CON 0,40250000                                 1
000107   10047515    10047515          CON A,3, OM                                    1
000110   23642040    23642040          CON A,3,OD                                     1
000111   24645511    24645511          CON A,3,SKI                                    1
000112   24050105    24050105          CON A,3,PPE                                    1
000113   21020106    21020106          CON A,3,D F                                    1
000114   22246124    22246124          CON A,3,ILT                                    1
000115   21251040    21251040          CON A,3,ER                                     1
```

```
000116  60077767   60077767            CON 0,60077767                                          1
                                       CONTINUE                                                 7
000117  300000000  300000000   $M1     BSS 0                                                    1
000117  16300414   16340275            LDX FILEX,3                                              6

*REINITILIZE FILTER INDEX >0                                6
000120  77300006   77300006   REFILT   STZ 6,3                                                  6

*RESET LOST INDEX FLAG                                      6
000121  77000413   77040272            STZ LIRFLG                                               6
000122  14000125   14040003            BRU SAVEIB                                               6

*IS LOST INDEX FLAG SET                                     6
000123  00000413   00040270   LOSTIX   LDA LIRFLG                                               6
000124  67000372   67040246            BNZ BENTER            YES                                6

*NO-LOAD HEAD POSITION SCAN ONLY FILE ADD (129) FROM FILE INTO X7   6
000125  00300003   00300003   SAVEIB   LDA 3,3                                                  6
000126  32000007   32000007            STA 7                                                    6

*IS HEAD STZ BIT 4 GROUP 1400 CLOSED!                       6
000127  25051400   25051400            IN /1400                                                 6
000130  05004704   05004704            TOD 4                                                    6
000131  30000246   30040115            BTR CHKSTZ                                               6

*IS HPOS LESS THAN MIN.POS.                                 6
000132  00700001   00700001            LDA 1,7                                                  6
000133  31300010   31300010            SUB 8,3                                                  6
000134  05004727   05004727            TOD 23                                                   6
000135  34000154   34040017            BTS STDPRG                                               6

*IS STANDARDIZE IN PROG SET                                 6
000136  00300000   00300000            LDA 0,3                                                  6
000137  05004727   05004727            TOD 23                                                   6
000140  30000143   30040003            BTR CHKMIN            NO                                 6

*RESET STDZ IN PROGRESS                                     6
000141  05046027   05046027            SBK 23                                                   6
000142  32300000   32300000            STA 0,3                                                  6

*IS HPOS LESS THAN MIN.POS.                                 6
000143  00700001   00700001   CHKMIN   LDA 1,7                                                  6
000144  31300010   31300010            SUB 8,3                                                  6
000145  05004727   05004727            TOD 23                                                   6
000146  30000165   30040017            BTR CKIEQ6                                               6

*INITILIZE FILTERED TABLE INITILIZATION INDEX K>7 IN FILE X  6
000147  40000007   40000007            LDK 7                                                    6
000150  32300011   32300011            STA 9,3                                                  6

*INITILIZE TEMP FILTER CYCLE   CYCLE>1 SAVE IN FILE X       6
000151  40000001   40000001            LDK 1                                                    6
000152  32300012   32300012            STA 10,3                                                 6
000153  14000372   14040217            BRU BENTER                                               6

*IS STANDARDIZE IN PROGRESS BIT 23 SET!                     6
000154  00300000   00300000   STDPRG   LDA 0,3                                                  6
000155  05004727   05004727            TOD 23                                                   6
000156  34000165   34040007            BTS CKIEQ6            YES                                6

*NO-SET STDZ IN PROGRESS                                    6
000157  05046027   05046027            SBK 23                                                   6
000160  32300000   32300000            STA 0,3                                                  6

*INITILIZE TEMP. FILTER CYCLE INDEX TO 1 IN FILE X          6
000161  40000001   40000001            LDK 1                                                    6
000162  32300012   32300012            STA 10,3                                                 6

*INITILIZE FILTERED TABLE INITILIZATION INDEX K>7          '6
000163  40000007   40000007            LDK 7                                                    6
000164  32300011   32300011            STA 9,3                                                  6

*IS THE INITILIZATION INDEX GREATER THAN 6 !                6
000165  00300011   00300011   CKIEQ6   LDA 9,3                                                  6
000166  50000006   50000006            SKA 6                                                    6
000167  05004727   05004727            TOD 23                                                   6
000170  30000372   30040202            BTR BENTER                                               6

*NO-IS IT EQUAL TO 6                                        6
000171  67000200   67040007            BNZ LDALPH                                               6

*IS THE CYCLE 0! OR MINUS                                   6
000172  00300012   00300012            LDA 10,3                                                 6
000173  66000200   66040005            BZE LDALPH                                               6
000174  05004727   05004727            TOD 23                                                   6
000175  34000200   34040003            BTS LDALPH                                               6
```

```
                                     *NO-DECRIMENT CYCLE INDEX + SAVE BACK IN FILEX                        6
000176   50000001   50000001          SKA 1                                                                 6
000177   32300012   32300012          STA 10,3                                                              6
                                                                                                            6
                                     *LOAD SMOOTHING CONSTANT FROM FILE                                     6
000200   00300013   00300013         LDALPH LDA 11,3                                                        6
000201   32000456   32040455          STA ALPHA                                                             6

*LOAD BASIS WT. FILE ADD + PUT FLOATED PV IN FILEX<122                 6
000202   00300007   00300007          LDA 7,3                                                               6
000203   32000006   32000006          STA 6                                                                 6
000204   00600002   00600002          LDA 2,6                                                               6

000205   74020010   74020010          FLO 8                                                                 6
000206   32300172   32300172          STA 122,3                                                             6
                                     *INITILIZE LOOP INDEX J>0                                              6
000207   77000412   77040203          STZ JINX                                                              6

*IS LOOP J ON SCAN                                                     6
000210   00400000   00400000         LOOPJ LDA 0,4                                                          6
000211   05004727   05004727          TOD 23                                                                6
000212   30000275   30040063          BTR CHK2ND                                                            6

*YES-LOAD STDZ. CORRECTION FACTOR FROM FILEX INTO C                    6
000213   00000412   00040177          LDA JINX                                                              6
000214   11000003   11000003          ADD 3                                                                 6
000215   32000006   32000006          STA 6                                                                 6
000216   00600014   00600014          LDA CTABL,6                                                           6
000217   32000654   32040435          STA CTABLE                                                            6

*LOAD PV FROM SCAN ONLY FILE(J)                                        6
000220   00400001   00400001          LDA 1,4                                                               6
000221   32000007   32000007          STA 7                                                                 6
000222   00700001   00700001          LDA 1,7                                                               6

*CONVERT TO ENGINEERING UNITS B1                                       6
000223   31000410   31040165          SUB EIGHTH                                                            6
000224   45004414   45004414          DRA 12                                                                6
000225   65000407   65040162          DVD THRTY2                                                            6
000226   00000010   00000010          LDA /10                                                               6
000227   74020001   74020001          FLO 1                                                                 6
000230   32000653   32040423          STA NCELL                                                             6
                                            REAL NCELL,NFCELL                                               7
                                     CCALC CORRECT INPUT                                                    7
                                            NCELL=NCELL*CTABLE                                              7
000231   00000653   00040422          LDA NCELL                                                             1
000232   72000654   72040422          FMP CTABLE                                                            1
000233   32000653   32040420          STA NCELL                                                             1
                                            CONTINUE                                                        7
000234   16300414   16340160          LDX FILEX,3                                                           6
000235   00000412   00040155          LDA JINX                                                              6
000236   11000003   11000003          ADD 3                                                                 6
000237   32000006   32000006          STA 6                                                                 6

*K GREATER THAN ZERO                                                   6
000240   00300011   00300011          LDA 9,3                                                               6
000241   66000243   66040002          BZE LDPREV                                                            6
000242   76000246   76040004          BNM CHKSTZ                                                            6

*LD.PREV SMOOTHED VALUE FROM FILEX INTO TEMP PFCELL                    6
000243   00600074   00600074         LDPREV LDA VTABL,6                                                     6
000244   32000657   32040413          STA PFCELL                                                            6
000245   14000253   14040006          BRU SMOALG                                                            6

*IS STANDARDIZE IN PROGRESS BIT SET                                    6
000246   00300000   00300000         CHKSTZ LDA 0,3                                                         6
000247   05004727   05004727          TOD 23                                                                6
000250   34000272   34040022          BTS LDPVJ                                                             6

*NO-MAKE PREV. SMOOTHED VALUE EQUAL TO NEW UNSMOOTHED INPUT            6
000251   00000653   00040402          LDA NCELL                                                             6
000252   32000657   32040405          STA PFCELL                                                            6
```

```
                                    *SMOOTHING ALGORITHM                                            6
000253  300000000  300000000        SMOALG BSS 0                                                    6
                                           NFCELL=ALPHA*NCELL+(1.-ALPHA)*PFCELL                     7
000253  00000656   00040403                LDA ALPHA                                                1
000254  72000653   72040377                FMP NCELL                                                1
000255  32000652   32040375                STA $TEMP                                                1
000256  00000651   00040373                LDA $FLCON                                               1
000257  71000656   71040377                FSU ALPHA                                                1
000260  72000657   72040377                FMP PFCELL                                               1
000261  70000652   70040371                FAD $TEMP                                                1
000262  32000655   32040373                STA NFCELL                                               1
                                           CONTINUE                                                 7
000263  16300414   16340131                LDX FILEX,3                                              6
000264  00000412   00040126                LDA JINX                                                 6
000265  11000003   11000003                ADD 3                                                    6
000266  32000006   32000006                STA 6                                                    6
                                    *SAVE NEW SMOOTHED VALUE BACK IN FILEX                          6
000267  00000655   00040366                LDA NFCELL                                               6
000270  32600074   32600074                STA VTABL,6                                              6
000271  14000275   14040004                BRU CHK2ND                                               6
                                    *LOAD PV FROM SCAN ONLY LOOP J FILE STORE IN FILEX STTABL(I,J)  6
000272  00700002   00700002        LDPVJ  LDA 2,7                                                   6
000273  74020001   74020001                FLO 1                                                    6
000274  32600034   32600034                STA STTABL,6                                             6
                                    *HAS SECOND INPUT BEEN PROCESSED                                6
000275  00000412   00040115        CHK2ND LDA JINX                                                  6
000276  67000304   67040006                BNZ KZERO                                                6
                                    *LOAD LOOP Q PCW PUT IN X4 + SET J INDEX TO ONE +RELOOP         6
000277  00300002   00300002                LDA 2,3                                                  6
000300  32000004   32000004                STA 4                                                    6

000301  40000001   40000001                LDK 1                                                    6
000302  32000412   32040110                STA JINX                                                 6
000303  14000210   14077705                BRU LOOPJ                                                6
                                    *IS K > TO ZERO                                                 6
000304  00300011   00300011        KZERO  LDA 9,3                                                   6
000305  66000313   66040006                BZE ISTAND                                               6
                                    *NO-IS IT LESS THAN 0                                           6
000306  05004727   05004727                TOD 23                                                   6
000307  34000372   34040063                BTS BENTER                                               6
                                    *NO-DECRIMENT INITILIZATION COUNT + SAVE IN FILE X              6
000310  50000001   50000001                SKA 1                                                    6
000311  32300011   32300011                STA 9,3                                                   6
000312  14000372   14040060                BRU BENTER                                               6
                                    *IS STANDARDIZE IN PROG SET                                     6
000313  00300000   00300000        ISTAND LDA 0,3                                                   6
000314  05004727   05004727                TOD 23                                                   6
000315  30000372   30040055                BTR BENTER                                               6
                                    *RESET STDZ BIT + SAVE IN FILEX                                 6
000316  05045027   05045027                RBK 23                                                   6
000317  32300000   32300000                STA 0,3                                                  6
                                    *INITIALIZE TEMP JCOUNT 0                                       6
000320  77000411   77040071                STZ JCOUNT                                               6
                                    *INITIALIZE TEMP.COUNT ICOUNT>0                                 6
000321  77002660   77002660        INITIO STZ ICOUNT                                                6
                                    *LOAD CORR.CONST.FROM FILEX STTABL(ICOUNT,JCOUNT)INTO TEMP RG   6
000322  00000411   00040067        LDCORR LDA JCOUNT                                                6
000323  11002660   11002660                ADD ICOUNT                                               6
000324  11000003   11000003                ADD 3                                                    6
000325  32000004   32000004                STA 4                                                    6
000326  00400166   00400166                LDA RSTABL,4                                             6
000327  32000661   32040332                STA RG                                                   6
                                    *LOAD OFF SHEET VALUES FROM FILEX STTABL(ICOUNT,JCOUNT)INTO TEMP ST  6
000330  00400034   00400034                LDA STTABL,4                                             6
000331  32000662   32040331                STA ST                                                   6
                                    *CALC CORR. FACTOR                                              6
```

```
000332   00000661   00040327               C=RG/ST
000333   73000662   73040327               LDA RG
000334   32000660   32040324               FDV ST
                                           STA C

CONTINUE

* IF REFL.(JCOUNT>0) MULT CTABL(I,J) BY EMPIRICAL CORR. CONSTANT IN
                              * MPAR<5, IF TRANSMITTANCE (JCOUNT>1), MULT. BY MPAR<6.
000335   00000411   00040054               LDA JCOUNT
000336   31002026   31002026               SUB TWO
000337   05004727   05004727               TOD 23
000340   30000375   30040035               BTR RTNRTM
000341   00000411   00040050               LDA JCOUNT
000342   32000004   32000004               STA 4
000343   04400417   04440054               XEC CORCAL,4
000344   32000663   32040317               STA CORR

C=C*CORR
000345   00000660   00040313               LDA C
000346   72000663   72040315               FMP CORR
000347   32000660   32040311               STA C

CONTINUE
000350   16300414   16340044               LDX FILEX,3
000351   00000411   00040040               LDA JCOUNT
000352   11002660   11002660               ADD ICOUNT
000353   32000004   32000004               STA 4

*SAVE CORR FACTOR IN FILEX CTABL(ICOUNT,JCOUNT)>C
000354   00000660   00040304               LDA C
000355   32400014   32400014               STA CTABL,4

*IS ICOUNT LESS THAN SIX!
000356   00002660   00002660               LDA ICOUNT
000357   50000005   50000005               SKA 5
000360   05004727   05004727               TOD 23
000361   30000365   30040004               BTR CKJCNT

*INX,ICOUNT BY 1
000362   60000001   60000001               AKA 1
000363   32002660   32002660               STA ICOUNT
000364   14000322   14077736               BRU LDCORR

*IS JCOUNT GREATER THAN ZERO
000365   00000411   00040024        CKJCNT LDA JCOUNT
000366   67000372   67040004               BNZ BENTER
000367   60000001   60000001               AKA 1
000370   32000411   32040021               STA JCOUNT
000371   14000321   14077730               BRU INITIO

*CLOSE FILTER ADVANCE SOLENOID DRIVE CONTACTS MOMENTARILY

*CALL TIMED OUTPUT RTMOS TIMED OUTPUT FOR .5 SEC.
000372   00000416   00040024        BENTER LDA AREG
000373   42000415   42040022               LDQ TIMEQ
000374   33000445   33000445               SPB MORC04

*SET UP FOR AUXTIME TURNON IN ONE SEC.
000375   00002707   00002707        RTNRTM LDA AUXTM+3
000376   31002100   31002100               SUB TIME
000377   05004527   05004527               SOD 23
000400   34000002   34077402               BTS EVERYL
000401   05046027   05046027               SBK 23
000402   32000404   32040002               STA *+2
000403   33000401   33000401               SPB DELC01
000404   300000001  300000001              BSS 1
000405   14000002   14077375               BRU EVERYL
000406   00000020   00000020        DLYTIM CON C,SECND*4
                                    DISCOF EQL /2777         TEMP-T1L-RE-ASSEMBLY
000407   00006200   00006200        THRTY2 CON D,3200
000410   06200000   06200000        EIGHTH CON D,800B12
000411   00000000   00000000        JCOUNT CON 0,0
000412   00000000   00000000        JINX   CON 0,0
000413   00000000   00000000        LIRFLG CON 0,0
000414   00063200   00063200        FILEX  CON 0,63200
000415   00017000   00017000        TIMEQ  CON D,30B15
000416   00000000   00000000        AREG   CON 0,0
000417   00000213   00000213        CORCAL LDA MPAR+5
000420   00000214   00000214               LDA MPAR+6
```

```
000421   300000226   300000226       FILEX1  BSS  150                                                    6
000647    33000404    33000404       TRNOFF  SPB  OFFC01           TURN PROG OFF                         6
000650    10000000    10077130               PRG  0,1,0,E014,0                                           6

END                                                         7
000651   300000000   300000000               BSS  0                                                      1
000651   300000000   300000000       $FXCON  BSS  0                                                      1
000651    20600000    20600000       $FLCON  CON  0,20600000                                             1
000652   300000000   300000000       $STBRU  BSS  0                                                      1
000652   300000001   300000001       $TEMP   BSS  1                                                      1
000653   300000001   300000001       NCELL   BSS  1                                                      1
000654   300000001   300000001       CTABLE  BSS  1                                                      1
000655   300000001   300000001       NFCELL  BSS  1                                                      1
000656   300000001   300000001       ALPHA   BSS  1                                                      1
000657   300000001   300000001       PFCELL  BSS  1                                                      1
000660   300000001   300000001       C       BSS  1                                                      1
000661   300000001   300000001       RG      BSS  1                                                      1
000662   300000001   300000001       ST      BSS  1                                                      1
000663   300000001   300000001       CORR    BSS  1                                                      1

*                                                           1

*PROGRAM END.   0 FORTRAN ERRORS                            1
```

Program Listing For Program Forty-Two (FIGS. 17-20)

The following listing is presented to illustrate the extent of the programming effort to implement the flow charts of FIGS. 17–20. It will be observed that the implementation of these flow charts together with the changes previously indicated herein and any necessary debugging is within the routine skill of the art.

```
103756 COMPILE
         814030060   814030060               IDN  000000                                                 1
         814030060   814030060                                                                           1

EQUIVALENCE(POPAC,OUTABL(1)),(YAR89,OUTABL(2)),(CYCLE,      7
                                            1FILEX (11)),(BW,    MPAR(5)),                               7
                                            1(TOPAC,OUTABL(3)),(XTRI,OUTABL(4)),(YTRI,OUTABL(5)),        7
                                            2(ZTRI,OUTABL(6)),(LH,OUTABL(7)),(AH,OUTABL(8)),             7
                                            3(BH,OUTABL(9)),(BRRINF,OUTABL(10))                          7
                                             INTEGER CYCLE                                               7
                                             REAL K,LNAX,KTABL,MPAR,LH                                   7
                                             NX = 0                                                      7
000000    00001527    00041527               LDA  $FXCON                                                 1
000001    32001560    32041557               STA  NX                                                     1
                                             DIMENSION TMPSAV (128)                                      7
                                             DIMENSION FILEX(0/11)                                       7
                                             DIMENSION RZTABL(0/7),TTABL(0/7),RITABL(0/7)                7
                                             DIMENSION STABL(0/7),KTABL(0/7),MPAR(0/6)                   7
                                            1,STTABL(0/7,0/1),RGTABL(0/7,0/1),VTABL(0/7,0/1),SGTABL(0/7,0/1)7
                                            2,OUTABL(0/9),RSTABL(0/7,0/1)                                7
                                             GO TO 5                                                     7
000002    14000071    14040067               BRU  $5                                                     1
                                             C GET TABLE OF SPECIFIC GRADE CORR. FACTORS FROM BULK TABLE. 7

*00000000   *00000000               END                                                         1
                                             0 ASSEMBLY ERRORS.
                                             000664 PROGRAM OCTAL SIZE.
                                             000314 EQL TABLE OCTAL SIZE.

CALL GET TABLE (NX,TMPSAV,IRR)                              7
000003    33000514    33000514               SPB  GETTAB                                                 1
000004    07301560    07341554               LXK  NX,3                                                   1
000005    07301606    07341601               LXK  TMPSAV,3                                               1
000006    07301561    07341553               LXK  IRR,3                                                  1

IF (IRR) 11,20,11                                           7
000007    00001561    00041552               LDA  IRR                                                    1
000010    05004727    05004727               TOD  23                                                     1
000011    34000015    34040004               BTS  $11                                                    1
000012    05004670    05004670               TZE                                                         1
```

```
000013   34000032   34040017              BTS $20                                                           1
000014   14000015   14040001              BRU $11                                                           1

11   PRINT (1)31                                                      7
000015   40000023   40040006         $11  LDK $31                                                           1
000016   45004330   45004330              MAQ                                                               1
000017   00001530   00041511              LDA $FXCON+1                                                      1
000020   33000561   33000561              SPB $PRINT                                                        1
000021   33000564   33000564              SPB $HLOUT                                                        1

31   FORMAT ($ OMOD DT $)                                             7
000022   14000030   14040006              BRU $M0                                                           1
000023   40110000   40110000         $31  CON 0,40110000                                                    1
000024   10047515   10047515              CON A,3, OM                                                       1
000025   23642040   23642040              CON A,3,OD                                                        1
000026   21052040   21052040              CON A,3,DT                                                        1
000027   60077773   60077773              CON 0,60077773                                                    1

STOP                                                             7
000030   33000405   33000405         $M0  SPB OFFC02                                                        1
000031   10000000   10000000              PRG 0,1,0,0,0                                                     1

20   CONTINUE                                                         7
000032   300000000  300000000        $20  BSS 0                                                             1

C COPY PERM. CORE FILE AT /63200 INTO PROG. WORKING AREA AT FILEX1    7
000032   16301526   16341474              LDX FILADD,3                                                      6
000033   40000226   40000226              LDK 150                                                           6
000034   32000005   32000005              STA 5                                                             6
000035   00002023   00002023              LDA ZERO                                                          6
000036   32000004   32000004              STA 4                                                             6
000037   00300000   00300000       NOTDON LDA 0,3                                                           6
000040   32401102   32441042              STA FILEX1,4                                                      6
000041   26300001   26300001              INX 1,3                                                           6
000042   26400001   26400001              INX 1,4                                                           6
000043   06000005   06000005              DMT 5                                                             6
000044   34000037   34077773              BTS NOTDON                                                        6

*GET INC TO CONSTANT TABLE FROM OPERATOR ENTERED MOD FILE             6
000045   16401331   16441264              LDX MOD,4                                                         6
000046   00400001   00400001              LDA 1,4                                                           6
000047   50000010   50000010              SKA 8               TEST FOR GRADE INCREMENT IN LIMITS            6
000050   05004727   05004727              TOD 23                                                            6
000051   30000054   30040003              BTR *+3                                                           6
000052   05000000   05000000              LDZ                                                               6
000053   14000055   14040002              BRU *+2                                                           6
000054   00400001   00400001              LDA 1,4                                                           6

*MULTIPLY BY 16 TO GET INCRIMENT                                      6
000055   05014047   05014047              SRA 7                                                             6

000056   32000004   32000004              STA 4                                                             6

C OVERLAY SPECIFIC GRADE CORR. FACTOR TABLE IN WORKING AREA           7
                                     C AT FILEX1<76 WITH 16 WORD TABLE SELECTED BY OPERATOR ENTERED NO.    7
000057   00025177   00025177              LDA FIFTEN                                                        6
000060   32000003   32000003              STA 3                                                             6
000061   00002023   00002023              LDA ZERO                                                          6
000062   32000005   32000005              STA 5                                                             6
000063   00401606   00441523       RELOOP LDA TMPSAV,4                                                      6
000064   32501216   32541132              STA SGTABL,5                                                      6
000065   26400001   26400001              INX 1,4                                                           6
000066   26500001   26500001              INX 1,5                                                           6
000067   06000003   06000003              DMT 3                                                             6
000070   34000063   34077773              BTS RELOOP                                                        6

5    CONTINUE                                                         7
000071   300000000  300000000        $5   BSS 0                                                             1

C CHECK IF CYCLE(NO. OF FILTER WHEEL REV. REQUIRED FOR NEW CALC.)     7

CHAS BEEN COUNTED DOWN TO ZERO BY PROG. 14.                     7

IF(CYCLE)10,10,120                                              7
000071   00001114   00041023              LDA CYCLE                                                         1
000072   05004727   05004727              TOD 23                                                            1
000073   34000077   34040004              BTS $10                                                           1
```

```
000074   05004670   05004670                 TZE                                              1
000075   34000077   34040002                 BTS $10                                          1
000076   14001100   14041002                 BRU $120                                         1

C SET UP J>1 TO INDEX TRANS. PARAMETERS.                             7

10      J=1                                             7
000077   00001530   00041431              $10 LDA $FXCON+1                                    1
000100   32001562   32041462                  STA J                                           1

I=0                                             7
000101   00001527   00041426                  LDA $FXCON                                      1
000102   32001563   32041461                  STA I                                           1

C LOAD TRANSMITTANCE SPECIFIC GRADE CORR. FOR ITH FILTER.            7

15      SGCF=SGTABL(I,J)                                7
000103   00001562   00041457              $15 LDA J                                           1
000104   45004330   45004330                  MAQ                                             1
000105   11001563   11041456                  ADD I                                           1
000106   55001531   55041423                  MPY $FXCON+2                                    1
000107   45006467   45006467                  DLA 23                                          1
000110   32001555   32041445                  STA $TEMP                                       1

000111   16301555   16341444                  LDX $TEMP,3                                     1
000112   00301216   00341104                  LDA SGTABL,3                                    1
000113   32001564   32041451                  STA SGCF                                        1

C LOAD DIFFUSOR TRANS. CONST. FROM RGTABL FOR ITH FILTER INTO TD.    7

TD=RGTABL(I,J)                                  7
000114   00001562   00041446                  LDA J                                           1
000115   45004330   45004330                  MAQ                                             1
000116   11001563   11041445                  ADD I                                           1
000117   55001531   55041412                  MPY $FXCON+2                                    1
000120   45006467   45006467                  DLA 23                                          1
000121   32001555   32041434                  STA $TEMP                                       1
000122   16401555   16441433                  LDX $TEMP,4                                     1
000123   00401156   00441033                  LDA RGTABL,4                                    1
000124   32001565   32041441                  STA TD                                          1

C LOAD SMOOTHED AND STANDARDIZE CORRECTED TRANS. RATIO INTO TDP.     7

TDP=VTABL(I,J)                                  7
000125   00001562   00041435                  LDA J                                           1
000126   45004330   45004330                  MAQ                                             1
000127   11001563   11041434                  ADD I                                           1
000130   55001531   55041401                  MPY $FXCON+2                                    1
000131   45006467   45006467                  DLA 23                                          1
000132   32001555   32041423                  STA $TEMP                                       1
000133   16501555   16541422                  LDX $TEMP,5                                     1
000134   00501176   00541042                  LDA VTABL,5                                     1
000135   32001566   32041431                  STA TDP                                         1

C CORRECT TDP FOR SPECIFIC GRADE.                                    7

TDP=TDP*SGCF                                    7
000136   00001566   00041430                  LDA TDP                                         1
000137   72001564   72041425                  FMP SGCF                                        1
000140   32001566   32041426                  STA TDP                                         1

C SET UP J>0 FOR REFLECTANCE PARAMETERS.                             7

J=0                                             7
000141   00001527   00041366                  LDA $FXCON                                      1
000142   32001562   32041420                  STA J                                           1

C LOAD BACKING PLATE REFLECTANCE FROM RGTABL INTO RG FOR ITH FILTER. 7

RG=RGTABL(I,J)                                  7
000143   00001562   00041417                  LDA J                                           1
000144   45004330   45004330                  MAQ                                             1
000145   11001563   11041416                  ADD I                                           1
000146   55001531   55041363                  MPY $FXCON+2                                    1
```

```
000147  45006467  45006467           DLA 23                                          1
000150  32001555  32041405           STA $TEMP                                       1
000151  16601555  16641404           LDX $TEMP,6                                     1
000152  00601156  00641004            LDA RGTABL,6                                   1
000153  32001567  32041414           STA RG                                          1
              C LOAD REFLECTANCE SPECIFIC GRADE CORR. FACTOR FOR ITH FILTER.         7

SGCF=SGTABL(I,J)                                                7
000154  00001562  00041406           LDA J                                           1
000155  45004330  45004330           MAQ                                             1
000156  11001563  11041405           ADD I                                           1

000157  55001531  55041352           MPY $FXCON+2                                    1
000160  45006467  45006467           DLA 23                                          1
000161  32001555  32041374           STA $TEMP                                       1
000162  16301555  16341373           LDX $TEMP,3                                     1
000163  00301216  00341033           LDA SGTABL,3                                    1
000164  32001564  32041400           STA SGCF                                        1
              C LOAD SMOOTHED AND STANDARDIZE CORRECTED REFLEC. RATIO INTO R.        7
                                                                                     7
                     R=VTABL(I,J)                                                    
000165  00001562  00041375           LDA J                                           1
000166  45004330  45004330           MAQ                                             1
000167  11001563  11041374           ADD I                                           1
000170  55001531  55041341           MPY $FXCON+2                                    1
000171  45006467  45006467           DLA 23                                          1
000172  32001555  32041363           STA $TEMP                                       1
000173  16401555  16441362           LDX $TEMP,4                                     1
000174  00401176  00441002           LDA VTABL,4                                     1
000175  32001570  32041373           STA R                                           1
              C CORRECT R FOR SPECIFIC GRADE.                                        7

R=R*SGCF                                                        7
000176  00001570  00041372           LDA R                                           1
000177  72001564  72041365           FMP SGCF                                        1
000200  32001570  32041370           STA R                                           1
              C CALC. RZERO FOR ITH FILTER.                                          7
                     RZERO=(R-RG*(TDP/TD)**2)/(1.-(RG*TDP/TD)**2)                    7
000201  00001566  00041365           LDA TDP                                         1
000202  73001565  73041363           FDV TD                                          1
000203  32001555  32041352           STA $TEMP                                       1
000204  00001567  00041363           LDA RG                                          1
000205  72001566  72041361           FMP TDP                                         1
000206  73001565  73041357           FDV TD                                          1
000207  32001556  32041347           STA $TEMP+1                                     1
000210  00001532  00041322           LDA $FXCON+3                                    1

000211  74020027  74020027           FLO 23                                          1
000212  33002036  33041624           SPB XXXEXP                                      1
000213  00001556  00041343           LDA $TEMP+1                                     1
000214  71001542  71041326           FSU $FLCON                                      1
000215  32001557  32041314           STA $TEMP+2                                     1
000216  00001532  00041314           LDA $FXCON+3                                    1
000217  74020027  74020027           FLO 23                                          1
000220  33002036  33041616           SPB XXXEXP                                      1
000221  00001555  00041334           LDA $TEMP                                       1
000222  72001567  72041345           FMP RG                                          1
000223  71001570  71041345           FSU R                                           1
000224  73001557  73041333           FDV $TEMP+2                                     1
000225  32001571  32041344           STA RZERO                                       1
              C CALC. TRANSMITTANCE T FOR ITH FILTER.                                7
                     T=(TDP*(1.-RG*R))/(TD*(1.-(RG*TDP/TD)**2))                      7
000226  00001567  00041341           LDA RG                                          1
000227  72001566  72041337           FMP TDP                                         1
000230  73001565  73041337           FDV TD                                          1
000231  32001555  32041324           STA $TEMP                                       1
000232  00001532  00041300           LDA $FXCON+3                                    1
000233  74020027  74020027           FLO 23                                          1
000234  33002036  33041602           SPB XXXEXP                                      1
000235  00001555  00041320           LDA $TEMP                                       1
000236  71001542  71041304           FSU $FLCON                                      1
000237  72001565  72041326           FMP TD                                          1
000240  32001556  32041316           STA $TEMP+1                                     1
000241  00001567  00041326           LDA RG                                          1
000242  72001570  72041326           FMP R                                           1
000243  71001542  71041277           FSU $FLCON                                      1
000244  72001566  72041322           FMP TDP                                         1
000245  73001556  73041311           FDV $TEMP+1                                     1
000246  32001572  32041324           STA T                                           1
              C CALC. INTERM. VARIABLE AI                                            7
```

```
                                AI=(1.0+RZERO**2-T**2)/(2.0*RZERO)                        7
000247  00001543   00041274         LDA  $FLCON+1                                          1
000250  72001571   72041321         FMP  RZERO                                             1
000251  32001555   32041304         STA  $TEMP                                             1
000252  00001532   00041260         LDA  $FXCON+3                                          1
000253  74020027   74020027         FLO  23                                                1
000254  33002036   33041562         SPB  XXXEXP                                            1
000255  00001571   00041314         LDA  RZERO                                             1
000256  70001542   70041264         FAD  $FLCON                                            1
000257  32001556   32041277         STA  $TEMP+1                                           1
000260  00001532   00041252         LDA  $FXCON+3                                          1
000261  74020027   74020027         FLO  23                                                1
000262  33002036   33041554         SPB  XXXEXP                                            1

000263  00001572   00041307         LDA  T                                                 1
000264  71001556   71041272         FSU  $TEMP+1                                           1
000265  73001555   73041270         FDV  $TEMP                                             1
000266  05004670   05004670         TZE                                                    1
000267  34000271   34040002         BTS  *+2                                               1
000270  05047027   05047027         CBK  23                                                1
000271  32001573   32041302         STA  AI                                                1
                              C CALC. INTERM. VARIABLE BI                                  7

BI=SQRTF(AI**2-1)                                          7
000272  00001532   00041240         LDA  $FXCON+3                                          1
000273  74020027   74020027         FLO  23                                                1
000274  33002036   33041542         SPB  XXXEXP                                            1
000275  00001573   00041276         LDA  AI                                                1
000276  32001555   32041257         STA  $TEMP                                             1
000277  00001530   00041231         LDA  $FXCON+1                                          1
000300  74020027   74020027         FLO  23                                                1
000301  71001555   71041254         FSU  $TEMP                                             1
000302  05004670   05004670         TZE                                                    1
000303  34000305   34040002         BTS  *+2                                               1
000304  05047027   05047027         CBK  23                                                1
000305  33002037   33041532         SPB  SQRTF                                             1
000306  32001574   32041266         STA  BI                                                1
                              C CALC. REFLECTANCE WITH INFINITE BACKING RINF>AI-BI         7

RINF=AI-BI                                                 7
000307  00001573   00041264         LDA  AI                                                1
000310  71001574   71041264         FSU  BI                                                1
000311  32001575   32041264         STA  RINF                                              1
                              C CALC. ARG. OF LOG FUNCTION, AX                             7

AX=(BI+SQRTF(BI*BI+T*T))/(T*(BI+AI))                       7
000312  00001574   00041262         LDA  BI                                                1
000313  72001574   72041261         FMP  BI                                                1
000314  32001555   32041241         STA  $TEMP                                             1
000315  00001572   00041255         LDA  T                                                 1
000316  72001572   72041254         FMP  T                                                 1
000317  70001555   70041236         FAD  $TEMP                                             1
000320  33002037   33041517         SPB  SQRTF                                             1
000321  32001556   32041235         STA  $TEMP+1                                           1
000322  00001574   00041252         LDA  BI                                                1
000323  70001573   70041250         FAD  AI                                                1
000324  72001572   72041246         FMP  T                                                 1
000325  32001557   32041232         STA  $TEMP+2                                           1
000326  00001574   00041246         LDA  BI                                                1
000327  70001556   70041227         FAD  $TEMP+1                                           1
000330  73001557   73041227         FDV  $TEMP+2                                           1

000331  32001576   32041245         STA  AX                                                1
                              C CALC. NAT. LOG OF AX                                       7

LNAX=LOGF(AX)                                              7
000332  00001576   00041244         LDA  AX                                                1
```

```
000333  33002040  33041505              SPB LOGF                                      1
000334  32001577  32041243              STA LNAX                                      1
000335  16601111  16640554              LDX FILEX1+7,6                                6
000336  00600001  00600001              LDA 1,6                                       6
000337  74020010  74020010              FLO 8                                         6
000340  32001314  32040754              STA BW                                        6
                          C CALC. SCATTER COEF S PER LB. BASIS WT.                    7
                                                                                      7
                                        S=LNAX/(BI*BW)                                7
000341  00001574  00041233              LDA BI                                        1
000342  72001314  72040752              FMP BW                                        1
000343  32001555  32041212              STA $TEMP                                     1
000344  00001577  00041233              LDA LNAX                                      1
000345  73001555  73041210              FDV $TEMP                                     1
000346  32001600  32041232              STA S                                         1
                          C CALC. ABSORPTION COEF. K PER LB. BASIS WT.                7
                                        K=S*(AI-1.)                                   7
000347  00001573  00041224              LDA AI                                        1
000350  71001542  71041172              FSU $FLCON                                    1
000351  72001600  72041227              FMP S                                         1
000352  32001601  32041227              STA K                                         1
                          C SAVE RZERO, T, RINF IN TEMPORARY ARRAYS.                  7
                                                                                      7
                                        RZTABL(I)=RZERO                               7
000353  00001571  00041216              LDA RZERO                                     1
000354  16501563  16541207              LDX I,5                                       1
000355  32502006  32541431              STA RZTABL,5                                  1
                                        TTABL(I)=T                                    7
000356  00001572  00041214              LDA T                                         1
000357  32502016  32541437              STA TTABL,5                                   1
                                        RITABL(I)=RINF                                7
000360  00001575  00041215              LDA RINF                                      1
000361  32502026  32541445              STA RITABL,5                                  1
                          C SAVE S AND K IN FILEX1 TABLES                             7
                                        STABL(I)=S                                    7
000362  00001600  00041216              LDA S                                         1
000363  32501250  32540665              STA STABL,5                                   1
                                        KTABL(I)=K                                    7
000364  00001601  00041215              LDA K                                         1
000365  32501260  32540673              STA KTABL,5                                   1
                                        IF(I-6)30,60,60                               7
000366  00001563  00041175              LDA I                                         1
000367  31001533  31041144              SUB $FXCON+4                                  1
000370  05004727  05004727              TOD 23                                        1
000371  34000375  34040004              BTS $30                                       1
000372  05004670  05004670              TZE                                           1
000373  34000403  34040010              BTS $60                                       1
000374  14000403  14040007              BRU $60                                       1
                                                                                      7
                                  30    J=1                                           
                                  $30   LDA $FXCON+1                                  1
000375  00001530  00041133                                                            
000376  32001562  32041164              STA J                                         1
                                        I=I+1                                         7
000377  00001563  00041164              LDA I                                         1
000400  11001530  11041130              ADD $FXCON+1                                  1
000401  32001563  32041162              STA I                                         1
                                        GO TO 15                                      7
000402  14000103  14077501              BRU $15                                       1
                          C CALC DIFF. IN Z REFLECT. WITH AND WITHOUT FLUOR + MULT. BY IMP.CON. 7
                                  60    ZFLUOR=(VTABL(6,0)-VTABL(3,0))*MPAR(0)        7
000403  00001204  00040601        $60   LDA VTABL+6                                   1
000404  71001201  71040575              FSU VTABL+3                                   1
000405  72001310  72040703              FMP MPAR                                      1
000406  32001602  32041174              STA ZFLUOR                                    1
                          C ADD DIFF. TO RINF FOR Z FILTER WITHOUT FLUOR. TO GET Z WITH FLUOR. 7
```

```
                                    ZRINF=RITABL(3)+ZFLUOR                                  7
000407    00002031    00041422      LDA RITABL+3                                            1
000410    70001602    70041172      FAD ZFLUOR                                              1
000411    32001603    32041172      STA ZRINF                                               1

C CALC. TRI STIM. XSUBG REFLECTANCE WITH FLUORECENCE BY ADDING              7
                C EMPIRICAL FRACT OF CHANGE IN Z REFL INPUTS DUE TO FLUOR                   7

XBRINF=RITABL(1)+ZFLUOR*MPAR(1)                         7
000412    00001602    00041170      LDA ZFLUOR                                              1
000413    72001311    72040676      FMP MPAR+1                                              1
000414    70002027    70041413      FAD RITABL+1                                            1

C CALC. TAPPI OPACITY                                                       7

TOPAC=RZTABL(5)/YAR89                                   7
000442    00002013    00041351      LDA RZTABL+5                                            1
000443    73001237    73040574      FDV YAR89                                               1
000444    32001240    32040574      STA TOPAC                                               1

C CALC. TRI-STIM X WITH XSUBB INCLUDING FLUOR.                              7

XTRI=.196*XBRINF+.784*RITABL(2)                         7
000445    00001545    00041100      LDA $FLCON+3                                            1
000446    72001604    72041136      FMP XBRINF                                              1

000447    32001555    32041106      STA $TEMP                                               1
000450    00001546    00041076      LDA $FLCON+4                                            1
000451    72002030    72041357      FMP RITABL+2                                            1
000452    70001555    70041103      FAD $TEMP                                               1
000453    32001241    32040566      STA XTRI                                                1

C CALC. TRI-STIM Y WITH ILLUM. C                                            7

YTRI=RITABL(4)                                          7
000454    00002032    00041356      LDA RITABL+4                                            1
000455    32001242    32040565      STA YTRI                                                1

000415    32001604    32041167      STA XBRINF                                              1

C CALC BRIGHTNESS FILTER REFLECTANCE WITH FLUOR BY ADDING                   7
                C EMPIRICAL FRACT OF CHANGEIN Z REFL INPUTS DUE T FLUOR.                    7

BRRINF=RITABL(0)+ZFLUOR*MPAR(2)                         7
000416    00001602    00041164      LDA ZFLUOR                                              1
000417    72001312    72040673      FMP MPAR+2                                              1
000420    70002026    70041406      FAD RITABL                                              1
000421    32001247    32040626      STA BRRINF                                              1

C CALC. PRINTING OPACITY AS RATIO OF RZERO/RINF FOR YSUBC FILTER.           7

POPAC=RZTABL(4)/RITABL(4)                               7
000422    00002012    00041370      LDA RZTABL+4                                            1
000423    73002032    73041407      FDV RITABL+4                                            1
000424    32001236    32040612      STA POPAC                                               1

C CALC. TRI-STIM Y REFL. WITH ILLUM. A + .89 BACKING.                       7

YAR89=RZTABL(5)+(.89*TTABL(5)*TTABL(5))                 7
                                    1/(1.-.89*RZTABL(5))                                    7
000425    00001544    00041117      LDA $FLCON+2                                            1
000426    72002013    72041365      FMP RZTABL+5                                            1
000427    71001542    71041113      FSU $FLCON                                              1
000430    32001555    32041125      STA $TEMP                                               1
000431    00001544    00041113      LDA $FLCON+2                                            1
000432    72002023    72041371      FMP TTABL+5                                             1
000433    72002023    72041370      FMP TTABL+5                                             1
000434    73001555    73041121      FDV $TEMP                                               1
000435    71002013    71041356      FSU RZTABL+5                                            1
000436    05004670    05004670      TZE                                                     1
000437    34000441    34000002      BTS *+2                                                 1
000440    05047027    05047027      CBK 23                                                  1
000441    32001237    32040576      STA YAR89                                               1
```

```
                                C CALC. TRI-STIM Z WITH FLUOR.
                                        ZTRI=1.18*ZRINF
000456    00001547    00041071            LDA $FLCON+5
000457    72001603    72041124            FMP ZRINF
000460    32001243    32040563            STA ZTRI

C CALC. HUNTER L COORD.
                                        LH=100.0*SQRTF(YTRI)
000461    00001242    00040561            LDA YTRI
000462    33002037    33041355            SPB SQRTF
000463    32001555    32041072            STA $TEMP
000464    00001550    00041064            LDA $FLCON+6
000465    72001555    72041070            FMP $TEMP
000466    32001244    32040556            STA LH

C CALC. HUNTER SMALL A.
                                        AH=175.*(1.02*XTRI-YTRI)/LH
000467    00001552    00041063            LDA $FLCON+8
000470    72001241    72040551            FMP XTRI
000471    71001242    71040551            FSU YTRI
000472    72001551    72041057            FMP $FLCON+7
000473    73001244    73040551            FDV LH
000474    32001245    32040551            STA AH

C CALC. HUNTER SMALL B.
                                        BH=70.*(YTRI-.847*ZTRI)/LH
000475    00001554    00041057            LDA $FLCON+10
000476    72001243    72040545            FMP ZTRI
000477    71001242    71040543            FSU YTRI
000500    72001553    72041053            FMP $FLCON+9
000501    73001244    73040543            FDV LH
000502    05004670    05004670            TZE
000503    34000505    34040002            BTS *+2
000504    05047027    05047027            CBK 23

000505    32001246    32040541            STA BH
                                C RESET FILTER CYCLE SLOWDOWN INDEX TO INITIAL VALUE IN MPAR<3
                                CAND STORE IN PERM. CORE FILE AT /63200<10 BASE 10
                                        FILEX(10)=MPAR(3)
000506    00001313    00040605            LDA MPAR+3
000507    32001114    32040405            STA FILEX+10
                                        CONTINUE
000510    16301526    16341016            LDX FILADD,3           SAVE WORKING CYCLE COUNT IN PERM CORE
000511    00001114    00040403            LDA FILEX1+10
000512    32300012    32300012            STA 10,3
                                        PRINT 600,(RZTABL(M),M=0,7)
000513    40000756    40040243            LDK $600
000514    45004330    45004330            MAQ
000515    33000561    33000561            SPB $PRINT
000516    00001527    00041011            LDA $FXCON
000517    32001605    32041066            STA M
000520    16601605    16641016     $M1    LDX M,6
000521    40602006    40641265            LDK RZTABL,6
000522    32001555    32041033            STA $TEMP
000523    33000563    33000563            SPB $OUTRP
000524    16701555    16741031            LDX $TEMP,7
000525    05003000    05003000            LDO 0
000526    11001605    11041057            ADD M
000527    32001605    32041056            STA M
000530    31001540    31041010            SUB $FXCON+9
000531    05004670    05004670            TZE
000532    05004527    05004527            SOD 23
000533    34000520    34077765            BTS $M1
000534    33000564    33000564            SPB $HLOUT

PRINT 600,(TTABL(M),M=0,7)
000535    40000756    40040221            LDK $600
000536    45004330    45004330            MAQ
000537    33000561    33000561            SPB $PRINT
000540    00001527    00040767            LDA $FXCON
000541    32001605    32041044            STA M
000542    16301605    16341043     $M2    LDX M,3
000543    40302016    40341253            LDK TTABL,3
000544    32001555    32041032            STA $TEMP
000545    33000563    33000563            SPB $OUTRP
000546    16701555    16741007            LDX $TEMP,7
000547    05003000    05003000            LDO 0
000550    11001605    11041035            ADD M
000551    32001605    32041034            STA M
000552    31001540    31040766            SUB $FXCON+9
```

```
000553    05004670   05004670              TZE                        1
000554    05004527   05004527              SOD 23                     1
000555    34000542   34077765              BTS $M2                    1
000556    33000564   33000564              SPB $HLOUT                 1
                                 PRINT 600,(RITABL(M),M=0,7)          7
000557    40000756   40040177              LDK $600                   1
000560    45004330   45004330              MAQ                        1
000561    33000561   33000561              SPB $PRINT                 1
000562    00001527   00040745              LDA $FXCON                 1
000563    32001605   32041022              STA M                      1
000564    16401605   16441021      $M3     LDX M,4                    1
000565    40402026   40441241              LDK RITABL,4               1
000566    32001555   32040767              STA $TEMP                  1
000567    33000563   33000563              SPB $OUTRP                 1
000570    16701555   16740765              LDX $TEMP,7                1
000571    05003000   05003000              LDO 0                      1
000572    11001605   11041013              ADD M                      1
000573    32001605   32041012              STA M                      1
000574    31001540   31040744              SUB $FXCON+9               1
000575    05004670   05004670              TZE                        1
000576    05004527   05004527              SOD 23                     1
000577    34000564   34077765              BTS $M3                    1
000600    33000564   33000564              SPB $HLOUT                 1
                                 PRINT 600,(STABL(M),M=0,7)           7
000601    40000756   40040155              LDK $600                   1
000602    45004330   45004330              MAQ                        1
000603    33000561   33000561              SPB $PRINT                 1
000604    00001527   00040723              LDA $FXCON                 1
000605    32001605   32041000              STA M                      1
000606    16501605   16540777      $M4     LDX M,5                    1
000607    40501250   40540441              LDK STABL,5                1
000610    32001555   32040745              STA $TEMP                  1
000611    33000563   33000563              SPB $OUTRP                 1
000612    16701555   16740743              LDX $TEMP,7                1
000613    05003000   05003000              LDO 0                      1
000614    11001605   11040771              ADD M                      1
000615    32001605   32040770              STA M                      1
000616    31001540   31040722              SUB $FXCON+9               1
000617    05004670   05004670              TZE                        1
000620    05004527   05004527              SOD 23                     1
000621    34000606   34077765              BTS $M4                    1
000622    33000564   33000564              SPB $HLOUT                 1
                                 PRINT 600,(KTABL(M),M=0,7)           7
000623    40000756   40040133              LDK $600                   1
000624    45004330   45004330              MAQ                        1
000625    33000561   33000561              SPB $PRINT                 1
000626    00001527   00040701              LDA $FXCON                 1
000627    32001605   32040756              STA M                      1
000630    16601605   16640755      $M5     LDX M,6                    1
000631    40601260   40640427              LDK KTABL,6                1
000632    32001555   32040723              STA $TEMP                  1
000633    33000563   33000563              SPB $OUTRP                 1
000634    16701555   16740721              LDX $TEMP,7                1
000635    05003000   05003000              LDO 0                      1
000636    11001605   11040747              ADD M                      1
000637    32001605   32040746              STA M                      1
000640    31001540   31040700              SUB $FXCON+9               1
000641    05004670   05004670              TZE                        1
000642    05004527   05004527              SOD 23                     1
000643    34000630   34077765              BTS $M5                    1
000644    33000564   33000564              SPB $HLOUT                 1
                                 PRINT 600,(STTABL(M,0),M=0,7)        7
000645    40000756   40040111              LDK $600                   1
000646    45004330   45004330              MAQ                        1
000647    33000561   33000561              SPB $PRINT                 1
000650    00001527   00040657              LDA $FXCON                 1
000651    32001605   32040734              STA M                      1
000652    16301605   16340733      $M6     LDX M,3                    1
000653    40301136   40340263              LDK STTABL,3               1
000654    32001555   32040701              STA $TEMP                  1
000655    33000563   33000563              SPB $OUTRP                 1
000656    16701555   16740677              LDX $TEMP,7                1
000657    05003000   05003000              LDO 0                      1
```

```
000660  11001605  11040725              ADD M                                              1
000661  32001605  32040724              STA M                                              1
000662  31001540  31040656              SUB $FXCON+9                                       1
000663  05004670  05004670              TZE                                                1
000664  05004527  05004527              SOD 23                                             1
000665  34000652  34077765              BTS $M6                                            1
000666  33000564  33000564              SPB $HLOUT                                         1
                                        PRINT 600,(STTABL(M,1),M=0,7)                      7
000667  40000756  40040067              LDK $600                                           1
000670  45004330  45004330              MAQ                                                1
000671  33000561  33000561              SPB $PRINT                                         1
000672  00001527  00040635              LDA $FXCON                                         1
000673  32001605  32040712              STA M                                              1
000674  16401605  16440711      $M7     LDX M,4                                            1
000675  40401146  40440251              LDK STTABL+8,4                                     1
000676  32001555  32040657              STA $TEMP                                          1
000677  33000563  33000563              SPB $OUTRP                                         1
000700  16701555  16740655              LDX $TEMP,7                                        1
000701  05003000  05003000              LDO 0                                              1
000702  11001605  11040703              ADD M                                              1
000703  32001605  32040702              STA M                                              1
000704  31001540  31040634              SUB $FXCON+9                                       1

000705  05004670  05004670              TZE                                                1
000706  05004527  05004527              SOD 23                                             1
000707  34000674  34077765              BTS $M7                                            1
000710  33000564  33000564              SPB $HLOUT                                         1
                                        PRINT 600,(RGTABL(M,0),M=0,7)                      7
000711  40000756  40040045              LDK $600                                           1
000712  45004330  45004330              MAQ                                                1
000713  33000561  33000561              SPB $PRINT                                         1
000714  00001527  00040613              LDA $FXCON                                         1
000715  32001605  32040670              STA M                                              1
000716  16501605  16540667      $M8     LDX M,5                                            1
000717  40501156  40540237              LDK RGTABL,5                                       1
000720  32001555  32040635              STA $TEMP                                          1
000721  33000563  33000563              SPB $OUTRP                                         1
000722  16701555  16740633              LDX $TEMP,7                                        1
000723  05003000  05003000              LDO 0                                              1
000724  11001605  11040661              ADD M                                              1
000725  32001605  32040660              STA M                                              1
000726  31001540  31040612              SUB $FXCON+9                                       1
000727  05004670  05004670              TZE                                                1
000730  05004527  05004527              SOD 23                                             1
000731  34000716  34077765              BTS $M8                                            1
000732  33000564  33000564              SPB $HLOUT                                         1
                                        PRINT 600,(RGTABL(M,1),M=0,7)                      7
000733  40000756  40040023              LDK $600                                           1
000734  45004330  45004330              MAQ                                                1
000735  33000561  33000561              SPB $PRINT                                         1
000736  00001527  00040571              LDA $FXCON                                         1
000737  32001605  32040646              STA M                                              1
000740  16601605  16640645      $M9     LDX M,6                                            1
000741  40601166  40640225              LDK RGTABL+8,6                                     1
000742  32001555  32040613              STA $TEMP                                          1
000743  33000563  33000563              SPB $OUTRP                                         1
000744  16701555  16740611              LDX $TEMP,7                                        1
000745  05003000  05003000              LDO 0                                              1
000746  11001605  11040637              ADD M                                              1
000747  32001605  32040636              STA M                                              1
000750  31001540  31040570              SUB $FXCON+9                                       1
000751  05004670  05004670              TZE                                                1
000752  05004527  05004527              SOD 23                                             1
000753  34000740  34077765              BTS $M9                                            1
000754  33000564  33000564              SPB $HLOUT                                         1
                                    600 FORMAT(8F10.5)                                     7
000755  14000760  14040003              BRU $M10                                           1
000756  02470056  02470056      $600    CON 0,02470056                                     1
000757  60077776  60077776              CON 0,60077776                                     1
```

```
                                          PRINT 600,(VTABL(M,0),M=0,7)                              7
000760   40000756   40077776        $M10  LDK $600                                                  1
000761   45004330   45004330              MAQ                                                       1
000762   33000561   33000561              SPB $PRINT                                                1
000763   00001527   00040544              LDA $FXCON                                                1
000764   32001605   32040621              STA M                                                     1
000765   16301605   16340620        $M11  LDX M,3                                                   1
000766   40301176   40340210              LDK VTABL,3                                               1
000767   32001555   32040566              STA $TEMP                                                 1
000770   33000563   33000563              SPB $OUTRP                                                1
000771   16701555   16740564              LDX $TEMP,7                                               1
000772   05003000   05003000              LDO 0                                                     1
000773   11001605   11040612              ADD M                                                     1
000774   32001605   32040611              STA M                                                     1
000775   31001540   31040543              SUB $FXCON+9                                              1
000776   05004670   05004670              TZE                                                       1
000777   05004527   05004527              SOD 23                                                    1
001000   34000765   34077765              BTS $M11                                                  1
001001   33000564   33000564              SPB $HLOUT                                                1

PRINT 600,(VTABL(M,1),M=0,7)                              7
001002   40000756   40077754              LDK $600                                                  1
001003   45004330   45004330              MAQ                                                       1
001004   33000561   33000561              SPB $PRINT                                                1
001005   00001527   00040522              LDA $FXCON                                                1
001006   32001605   32040577              STA M                                                     1
001007   16401605   16440576        $M12  LDX M,4                                                   1
001010   40401206   40440176              LDK VTABL+8,4                                             1
001011   32001555   32040544              STA $TEMP                                                 1
001012   33000563   33000563              SPB $OUTRP                                                1
001013   16701555   16740542              LDX $TEMP,7                                               1
001014   05003000   05003000              LDO 0                                                     1
001015   11001605   11040570              ADD M                                                     1
001016   32001605   32040567              STA M                                                     1
001017   31001540   31040521              SUB $FXCON+9                                              1
001020   05004670   05004670              TZE                                                       1
001021   05004527   05004527              SOD 23                                                    1
001022   34001007   34077765              BTS $M12                                                  1
001023   33000564   33000564              SPB $HLOUT                                                1

PRINT 700,(MPAR(M),M=0,6)                                 7
001024   40001047   40040023              LDK $700                                                  1
001025   45004330   45004330              MAQ                                                       1
001026   33000561   33000561              SPB $PRINT                                                1
001027   00001527   00040500              LDA $FXCON                                                1
001030   32001605   32040555              STA M                                                     1
001031   16501605   16540554        $M13  LDX M,5                                                   1
001032   40501310   40540256              LDK MPAR,5                                                1
001033   32001555   32040522              STA $TEMP                                                 1
001034   33000563   33000563              SPB $OUTRP                                                1

001035   16701555   16740520              LDX $TEMP,7                                               1
001036   05003000   05003000              LDO 0                                                     1
001037   11001605   11040546              ADD M                                                     1
001040   32001605   32040545              STA M                                                     1
001041   31001533   31040472              SUB $FXCON+4                                              1
001042   05004670   05004670              TZE                                                       1
001043   05004527   05004527              SOD 23                                                    1
001044   34001031   34077765              BTS $M13                                                  1
001045   33000564   33000564              SPB $HLOUT                                                1

700   FORMAT(3F10.5,I10,3F10.5)                                7
001046   14001053   14040005              BRU $M14                                                  1
001047   02420056   02420056        $700  CON 0,02420056                                           1
001050   22401602   22401602              CON 0,22401602                                            1
001051   02420056   02420056              CON 0,02420056                                            1
001052   60077774   60077774              CON 0,60077774                                            1

PRINT 500,(OUTABL(M),M=0,9)                               7
001053   40001076   40040023        $M14  LDK $500                                                  1
001054   45004330   45004330              MAQ                                                       1
001055   33000561   33000561              SPB $PRINT                                                1
001056   00001527   00040451              LDA $FXCON                                                1
001057   32001605   32040526              STA M                                                     1
001060   16601605   16640525        $M15  LDX M,6                                                   1
001061   40601236   40640155              LDK OUTABL,6                                              1
001062   32001555   32040473              STA $TEMP                                                 1
001063   33000563   33000563              SPB $OUTRP                                                1
001064   16701555   16740471              LDX $TEMP,7                                               1
001065   05003000   05003000              LDO 0                                                     1
001066   11001605   11040517              ADD M                                                     1
001067   32001605   32040516              STA M                                                     1
001070   31001541   31040451              SUB $FXCON+10                                             1
001071   05004670   05004670              TZE                                                       1
001072   05004527   05004527              SOD 23                                                    1
001073   34001060   34077765              BTS $M15                                                  1
001074   33000564   33000564              SPB $HLOUT                                                1
```

```
                                    500  FORMAT(10F10.5)                        7
001075  14001100   14040003              BRU  $M16                               1
001076  02510056   02510056         $500 CON  0,02510056                         1
001077  60077776   60077776              CON  0,60077776                         1

120  CONTINUE                                7
001100  300000000  300000000        $M16 BSS  0                                  1
001100  300000000  300000000        $120 BSS  0                                  1

C TURN PROG. 42 OFF. WILL BE TURNED ON BY PROG. 14   7

STOP                                    7
001100  33000405   33000405              SPB  OFFC02                             1

001101  10000000   10000000              PRG  0,1,0,0,0                          1
001102  300000014  300000014        FILEX1 BSS 12                                6
001116  300000020  300000020        CTABL1 BSS 16                                6
001136  300000020  300000020        STTAB1 BSS 16                                6
001156  300000020  300000020        RGTAB1 BSS 16                                6
001176  300000020  300000020        VTABL1 BSS 16                                6
001216  300000020  300000020        SGTAB1 BSS 16                                6
001236  300000012  300000012        OUTAB1 BSS 10                                6
001250  300000010  300000010        STABL1 BSS 8                                 6
001260  300000010  300000010        KTABL1 BSS 8                                 6
001270  300000020  300000020        RSTAB1 BSS 16                                6
001310  300000020  300000020        MPAR1  BSS 16                                6
001330  00070632   00070632         BWPFA  CON  0,70632                          6
001331  00073261   00073261         MOD    CON  0,73261                          6
                                    CON    EQL  *                                6
001332  300000174  300000174               BSS  124                              6
001526  00063200   00063200         FILADD CON  0,63200                          6

DEFINE CTABL(CTABL1),FILEX(FILEX1)      7
                                    CTABL EQL CTABL1                             1
                                    FILEX EQL FILEX1                             1

DEFINE STTABL(STTAB1),RGTABL(RGTAB1)    7
                                    1,VTABL(VTABL1),SGTABL(SGTAB1),OUTABL(OUTAB1),STABL(STABL1),   7
                                    2KTABL(KTABL1),RSTABL(RSTAB1)                7
                                    STTABL EQL STTAB1                            1
                                    RGTABL EQL RGTAB1                            1
                                    VTABL  EQL VTABL1                            1
                                    SGTABL EQL SGTAB1                            1
                                    OUTABL EQL OUTAB1                            1
                                    STABL  EQL STABL1                            1
                                    KTABL  EQL KTABL1                            1
                                    RSTABL EQL RSTAB1                            1

DEFINE MPAR(MPAR1)                      7
                                    MPAR  EQL MPAR1                              1

END                                     7
001527  300000000  300000000              BSS  0                                 1
001527  00000000   00000000         $FXCON CON  0,00000000                       1
001530  00000001   00000001               CON  0,00000001                        1
001531  00000010   00000010               CON  0,00000010                        1
001532  00000002   00000002               CON  0,00000002                        1
001533  00000006   00000006               CON  0,00000006                        1
001534  00000003   00000003               CON  0,00000003                        1
001535  00000004   00000004               CON  0,00000004                        1
001536  00000005   00000005               CON  0,00000005                        1
001537  00000012   00000012               CON  0,00000012                        1
```

```
001540  00000007   00000007              CON  0,00000007                       1
001541  00000011   00000011              CON  0,00000011                       1
001542  20600000   20600000      $FLCON  CON  0,20600000                       1
001543  21200000   21200000              CON  0,21200000                       1
001544  20343656   20343656              CON  0,20343656                       1
001545  17310550   17310550              CON  0,17310550                       1
001546  20310550   20310550              CON  0,20310550                       1
001547  20627024   20627024              CON  0,20627024                       1
001550  23710000   23710000              CON  0,23710000                       1
001551  24257000   24257000              CON  0,24257000                       1
001552  20602437   20602437              CON  0,20602437                       1
001553  23614000   23614000              CON  0,23614000                       1
001554  20330652   20330652              CON  0,20330652                       1
001555  300000000  300000000     $STBRU  BSS  0                                1
001555  300000003  300000003     $TEMP   BSS  3                                1
                                 POPAC   EQL  CUTABL                           1
                                 YARB9   EQL  OUTABL+1                         1
                                 CYCLE   EQL  FILEX+10                         1
                                 BW      EQL  MPAR+4                           1
                                 TOPAC   EQL  OUTABL+2                         1
                                 XTRI    EQL  OUTABL+3                         1
                                 YTRI    EQL  OUTABL+4                         1
                                 ZTRI    EQL  OUTABL+5                         1
                                 LH      EQL  OUTABL+6                         1
                                 AH      EQL  OUTABL+7                         1
                                 BH      EQL  OUTABL+8                         1
                                 BRRINF  EQL  OUTABL+9                         1
001560  300000001  300000001     NX      BSS  1                                1
001561  300000001  300000001     IRR     BSS  1                                1
001562  300000001  300000001     J       BSS  1                                1
001563  300000001  300000001     I       BSS  1                                1
001564  300000001  300000001     SGCF    BSS  1                                1
001565  300000001  300000001     TD      BSS  1                                1
001566  300000001  300000001     TOP     BSS  1                                1
001567  300000001  300000001     RG      BSS  1                                1
001570  300000001  300000001     R       BSS  1                                1
001571  300000001  300000001     RZERO   BSS  1                                1
001572  300000001  300000001     T       BSS  1                                1
001573  300000001  300000001     AI      BSS  1                                1
001574  300000001  300000001     BI      BSS  1                                1
001575  300000001  300000001     RINF    BSS  1                                1
001576  300000001  300000001     AX      BSS  1                                1
001577  300000001  300000001     LNAX    BSS  1                                1
001600  300000001  300000001     S       BSS  1                                1
001601  300000001  300000001     K       BSS  1                                1
001602  300000001  300000001     ZFLUOR  BSS  1                                1
001603  300000001  300000001     ZRINF   BSS  1                                1
001604  300000001  300000001     XBRINF  BSS  1                                1
001605  300000001  300000001     M       BSS  1                                1
001606  300000200  300000200     TMPSAV  BSS  128                              1

002006  300000010  300000010     RZTABL  BSS  8                                1
002016  300000010  300000010     TTABL   BSS  8                                1
002026  300000010  300000010     RITABL  BSS  8                                1
002036  926054130  926054130     XXXEXP  LIB                                   1
        921254120  921254120                                                   1
002037  924650522  924650522     SQRTF   LIB                                   1
        925043040  925043040                                                   1
002040  923047507  923047507     LOGF    LIB                                   1
        921420040  921420040                                                   1
                                 *                                             1
                                 *PROGRAM END.    0 FORTRAN ERRORS             1
        *00000000  *00000000             END                                   1
                                                  0 ASSEMBLY ERRORS            1
                                        002342  PROGRAM OCTAL SIZE.
                                        000470  EQL TABLE OCTAL SIZE.
```

PROPOSED OPTICAL CONTROL STRATEGY

While the on-line automatic control of paper optical properties is an ultimate objective of the work reported herein, the claimed subject matter relates to on-machine monitoring of paper optical properties whether used as an aid to conventional manual control or for other purposes. Nevertheless, in order to provide a disclosure of the best mode presently contemplated for automatic control as a separate but related area of endeavor, the following discussion is presented.

The optical properties of a sheet of paper are dependent upon all of the materials of which it is made but primarily upon the furnished pulp, fillers, pigments, dyes, and some additives. It is often very difficult to maintain the optical attributes of the pulp, fillers and additives constant within a given production run. Such variation is even greater between runs. The optical properties of the finished paper may, however, be reasonably controlled to specified standards by varying the additions of dyes and fillers and pigments until the desired compensations are achieved. The problem is that each furnished ingredient affects each of the resulting paper optical properties in a rather complicated manner. Indeed the intuition of experienced papermakers has essentially been the sole method of optical property control. Unfortunately, this approach is inefficient, resulting in considerable off-standard paper and/or waste of costly materials. Accordingly, a dire need exists within the paper industry for a highly reliable and continuous optical property monitor coupled with a closed loop computer control system.

The value of such closed loop control, based on a feedback color detector, has already been demonstrated for the continuous addition of two and sometimes three dyes. (1) (2) Target dye concentrations changes of up to three dyes can be determines by solving three simultaneous equations containing three unknowns. (1) One disadvantage of such control is that accurate color monitoring is not presently available unless large and frequent empirically determined correction factors are applied to the original output results. A second disadvantage arises when opacity and the fluorescence must also be simultaneously controlled. In this case the number of independently controlled continuous additions increases from three to five. An optical brightener and an opacifying pigment constitute the two additional factors.

An object of this invention is to demonstrate a method by which fluorescence can be continuously monitored. A means by which the optical brightener addition can be separately and independently controlled is inherently implied. The paper color is also analyzed without the fluorescent contribution. It is, of course, this latter characterization (without fluorescence) which should be, but which has not in the past been, used to determine the required addition of the conventional dyes. In other words, the effect of the optical brightened is decoupled from the three conventional dyes making possible the simultaneous control of all four dyes.

Another portion of this invention demonstrates a means of continuously determining the scatting coefficient of the moving web for each of the six available light spectrums. It is possible to determine the scattering coefficient required to achieve a given opacity specification whenever the basis weight and absorption coefficient are known. When the latter are set equal to a given set of product specifications, then the calculated scattering coefficient becomes the target scattering coefficent. (The absorption coefficient can be acquired by off-line testing of a sample of the standard color to be matched. In reality, this becomes a target absorption coefficient as well). The dyes have little, if any, effect on the scattering coefficient but the effect of the slurry pigment is very large. Thus the target scattering coefficient is used as the sole feedback variable to control the slurry pigment feed. This will insure that the opacity is at or near the specification as long, as the absorption coefficient and basis weight are also on target. The absorption coefficient should, of course, be on target by virtue of the independent color control. A completely independent system controls the basis weight.

A method by which the decoupling of three conventional dyes, one optical brightener and one opacifying pigment has hereby been explained. Heretofore, such decoupling as revealed in the prior art has been limited to three absorptive dyes and thereby neglecting the need to also achieve a specified degree of fluorescence and opacity.

REFERENCES

1. The development of dynamic color control on a paper machine by H. Chao and W. Wickstrom; Automatica, Vol. 6 PP 5–18, Pergamon Press, 1970.
2. Another consideration for color and formation by Henry H. Chao and Warren A. Wickstrom, color engineering, Sept/Oct. 1971.

DISCUSSION OF THE CLAIM TERMINOLOGY AND SCOPE

The present invention is for the purpose of obtaining a quantitative measure of an optical property such as brightness, color, opacity or fluorescence of single thickness sheet material.

The sheet material is substantially homogeneous in its thickness dimension such that the optical property of interest can be reliably calculated from reflectance and transmittance measurements on the basis of existing theory. Thus the present invention is not applicable to the sensing of localized surface effects (such as due to surface migration of light absorbing powder particles, for example). To the contrary the present invention is concerned with the average or bulk optical characteristics of the sheet material considered as a whole, and especially is concerned with the characteristics of paper sheet material as it is delivered from a paper machine after completion of the paper manufacturing process.

The present invention in its broader aspect does not require strictly homogeneous material since empirical correction factors can be applied for cases where theory is less effective. For example, the paper optical properties of calendered and coated papers may be effectively measured by the system of the present invention using grade correction factors to correlate on-machine results with the measurements obtained by standard off-line instruments.

The optical system of the monitoring device includes components such as those shown in FIG. 3 which define or optically affect the incident, reflected and transmitted light paths such as indicated at 133, 137 and 141–143 in FIG. 3. For the case of a filter wheel as indicated in FIG. 4, each filter wheel position may be considered to define a separate light energy path with its own predetermined spectral response characteristics.

In each filter wheel position, there are two distinct light energy paths for measuring a reflectance value and a transmittance value, respectively. In the illustrated embodiment each such light energy path includes a common incident light path 133, but the paths diverge, one coinciding with the reflectance sensing light path 137 and the other including the transmittance sensing light path. The photometric sensors 203 and 260 thus provide simultaneous reflectance and transmittance output signals with respect to essentially a common region of the web. The reflectance sensing light path collects light from a circular region with a diameter of about 3/16 inch, and the transmittance sensing light path collects light from a total elliptical region which includes substantially the same circular region as mentioned above. Because of sheet formation effects and other localized variations in web characteristics it is considered valuable that the reflectance and transmittance output signals are based on readings from essentially a common region of the web.

By taking at least one reading in each traverse of the web, and taking such readings at different points along the width in successive traverses, it is considered that accuracies equal to or superior to those of an off-line sampling of a finished reel can be achieved, while at the same time the readings are available immediately instead of after completion of a manufacturing run.

By way of example, in the illustrated system a traversal of the web by the sensing head takes about forty-five seconds, so that the sensing head operates at a rate of at least one traversal of the width of the web per minute in the time intervals between the hourly off-sheet standardizing operations.

In accordance with the teachings of an improvement to the present invention, the optical window 135 is itself selected as to its optical characteristics so as to provide the basis for off-sheet standardization. To this end it is advantageous that the optical window exhibit an absolute reflectance value as measured by the standard automatic color-brightness tester of at least about 35%. The corresponding absolute transmittance value as measured on the G.E. Recording Spectrophotometer with conventional optics is about 56%. With the illustrated embodiment, once the system is properly adjusted with respect to the zero reflectance readings (as by the use of a black sheet of known minimal reflectance) the system maintains such zero adjustment quite stably; accordingly the higher the reflectance value of the optical window, the more effective is the reflectance standardization by means of the optical window. On the other hand a transmittance value which is of a reasonable magnitude is also desirable, so that the provision of an optical window with substantial values of absolute reflectance and transmittance is advantageous.

With the illustrated embodiment, the transmittance readings for the moving web are relatively more nearly independent of misalignment of the upper and lower sensing heads than the reflectance readings. Further it is considered that tilting of the lower sensing head relative to the optical axis of the upper sensing head has less effect on transmittance readings than on reflectance readings. Thus it is considered that it would be advantageous to have an optical window such as 135 with an absolute reflectance value of 70% or more. A value of reflectance as high as 90% would not be unreasonable and would generally still permit a transmittance value of a substantial magnitude to give reasonably comparable accuracy of reflectance and transmittance readings for on-line operation as herein described.

While separate photometric sensing means for the reflectance and transmittance readings have been shown, it is possible with the use of fiber optics, for example, to use a common photometric sensor and alternately supply light energy from the reflectance and transmittance light paths thereto, providing the response time of the sensor enables reflectance and transmittance readings to be obtained for essentially the same region of the moving web. Generally the possibility of such time multiplexing of reflectance and transmittance readings will depend on the speed of movement of the web and the degree of uniformity of sheet formation and the like.

It is very desirable that the system of the present invention be applicable to sheet materials having a wide range of characteristics such as basis weight and sheet formation, and operable at high speeds of movement such as 100 to 3000 feet per minute. Further, for maximum accuracy, it is necessary that a region of the sheet material being sampled have substantially uniform opacity. Accordingly, especially for sheet material of relatively low basis weight and relatively poor sheet formation, greater accuracy can be expected when the response of the photometric sensor is relatively fast, and when reflectance and transmittance readings are taken simultaneously and are a measure of the characteristics of a common sampling region of minimum area (consistent with adequate signal to noise ratios). Thus multiplexing of reflectance and transmittance readings is not preferred for the case of high speed paper machinery and comparable environments, nor is it desirable to use reflectance and transmittance light paths which intersect the web at spacially offset regions.

With respect to speed of response of the photometric sensing means, substantial improvements over the previously described components are deemed presently available. If the spectral response and other necessary characteristics are suitable, a sensor with such a higher speed of response is preferred for the illustrated embodiment. Good experience has been had with a silicon photocell presently considered as having an appropriate spectral response characteristics for color and other measurements in accordance with the present invention. The specific silicon cell referred to is identified as a Schottky Planar Diffuse Silicon Pin 10 DP photodiode of a standard series supplied by United Detector Technology Incorporated, Santa Monica, California.

In place of rotatable filter wheel arrangement as shown in FIGS. 3 and 4, a set of twelve fiber optic light paths may define six simultaneously operative reflectance light paths in upper sensing head 11 and six simultaneously operative transmittance light paths in lower sensing head 12. The six reflectance fiber optic paths would include respective filters corresponding to filters 281–286 and respective individual photocells and would be located to receive respective portions of the reflected light which is reflected generally along path 137 in FIG. 3. The six transmittance fiber optic paths would also include respective filters corresponding to filters 281–286 and respective individual photocells, and would be located to receive respective portions of the transmitted light which is transmitted generally along paths such as 141–143 in FIG. 3. The filter means in the incident light path such as indicated at 133 in FIG. 3 might include a filter in series with filters 271 and 272 for filtering out the ultraviolet component from the incident beam, so that the twelve simultaneous photocell readings corresponding to those designated RSD1 through RSD6, and TSD1 through TSD6 (when the device is off-sheet), and corresponding to those designated RSP1 through RSP6, and TSP1 through TSP6 (when the device is on-sheet) will exclude a flourescent contribution. (See Table 3 where this notation is introduced.)

If a reflectance reading corresponding to RSD7 (when the device is off-sheet) and corresponding to RSP7 (when the device is on-sheet) is desired so as to enable computation of flourescent contribution to brightness, it would be necessary to mechanically remove the ultraviolet filter from the incident light path, or otherwise introduce an ultraviolet component of proper magnitude, and obtain another brightness (Z) reading, for example from the number four reflectance photocell.

As an alternative to the above fiber optic system with a common incident light path, seven fiber optical tubes incorporating filters corresponding to 281–287 of FIGS. 3 and 4, respectively, at say the light exit points of the tubes, could be used to supply the incident light to seven different points on the paper web. The reflected light from each of these seven points could be monitored by seven different systems, each involving lenses and a photocell, and the number seven reflected light path including also a filter corresponding to filter 288, FIG. 4. The transmitted light from the first six points would also need to be kept separately, and this could be accomplished by six integrating cavities and six photocells.

As a further alternative the seven fiber optical tubes defining the seven incident light paths could have a second set of seven fiber optical tubes and photocells respectively disposed to receive reflected light from the respective illuminated points. Another set of six fiber optical tubes and photocells could be associated with the first six illuminated points for receiving transmitted light. This could eliminate the need for the light collecting lenses in the upper sensing head and the integrating cavities in the lower sensing head.

The last two mentioned alternatives with seven fiber optical tubes defining the incident light paths appear to be rather complicated systems, but they do offer means of eliminating both mechanical filter wheel as well as any mechanical device to control the presence of ultraviolet light in the incident beam.

Still another alternative is to use "screens" in addition to the filters in the embodiment of FIGS. 1–5. The new photodiodes are considered sensitive enough to measure reduced light intensites so that the screens with different transmittance values could be used with six of the incident beam filters so that the net photocell output for each reflectance light path, and for each transmittance light path, would be similar enough so that separate and individual pre-amplification for the respective reflectance outputs would not be necessary, and so that separate and individual preamplification for each transmittance output would not be necessary. This means that reed switches 314–347 and 351–357, and relays $K_1$ through $K_7$ in FIG. 6 could be eliminated, and that the feeback paths for amplifiers 361 and 429 could have the same resistance value in each filter wheel position. A means of sensing filter wheel position would still be necessary, but this could be done in a number of simple ways, one of which would be a single reed switch such as reed switch 358 shown in FIG. 6. The number of necessary conductors in the cables 51 and 52, FIG. 5, would, of course, be reduced in this modification.

The term "screen" is understood in the art as referring to a network of completely opaque regions and intervening openings or completely translucent regions, such that light energy is uniformly attenuated over the entire spectrum by an amount dependent on the proportion of opaque to transmitting area.

The device of FIGS. 1 and 2 has been tested on a machine operating at about 1000 feet per minute, and no problems have appeared in maintaining the necessary uniform and stable contact geometry between the head and the moving web.

It will be apparent that many further modifications and variations may be effected without departing from the scope of the novel concepts of the present invention.

DESCRIPTION OF THE OFF-THE-MACHINE OPTICAL DEVICE OF FIGS. 21-23

FIGS. 21–23 illustrate an instrument for use off the paper machine. It is contemplates that this instrument will enable the development of the relationships between off-machine specification and the on-line instrument of FIGS. 1–20. These relationships would include the "grade-correction" factors to be used in the on-line system of FIGS. 1–20 relative to off-machine optical specifications. The instrument is shown as including a specimen support 1000 having an aperture 1001 which may conform with the aperture 130, FIG. 3, in diameter. The web support 1000 is of extended area so as to be capable of conveniently supporting a full-width web and for adjustment of such web to expose successive portions thereof at the aperture 1001. At the same time, the support 1000 will accommodate a small size paper specimen such as indicated at 1002. Generally the housing for the optical components will conform with the housing 11 of the prior embodiment from the standpoint of light proofing and interior finish.

The optical system as diagrammatically indicated includes a light source means 1010 and the lenses 1011–1016 generally having the characteristics of the lenses 202, 273 and 274 of FIG. 3 of the previous embodiment, and such that the spectral response of the system can duplicate that of the prior embodiment. The illustrated optical system further includes a fixed lamp socket 1020 and an iris diaphram 1021 for attenuating the incident light beam.

FIG. 21 illustrates also a transmittance sensing head 1025 which may be hingedly secured to the support 1000 at a single corner so as to minimize the obstruction provided to movement of a paper web over the support surface 1000. The transmittance sensing head 1025 may include an optical window 1026 of the same diameter, thickness and physical composition and characteristics as the window 135 of the prior embodiment. The description with respect to the window 135 is specifically incorporated here with respect to the window 1026 in its entirety. As illustrated, the lower surface of window 1026 may directly contact the paper specimen 1002 which will be in smooth continuous contact therewith over the optical viewing area of the system which may be of the same dimensions as that described with respect to the prior embodiment. The sensing head 1025 may comprise a light integrating cavity 1028 and a transmittance sensing light photocell 1030.

It will be understood that the reflectance and transmittance light paths have the incident path in common, and that in the illustrated embodiment the transmittance light path into the integrating cavity 1028 may conform with those described with respect to FIG. 3. Also, the reflectance light path generally conforms with that of FIG. 3 and includes a reflectance photocell 1032. The photocell 1032 may have a plate 1033 with a ⅜-inch aperture and may conform with the plate 275 of FIG. 3. Thus, a piece of diffusing glass corresponding to the glass 276 of FIG. 3 may be located in the aperture so that the light distribution over the surface of the photocell 1032 will conform to the light distribution with respect to the surface of photocell 203 in FIG. 3.

The instrument of FIG. 21 further includes an incident light filter disk 1040 and a reflectance filter disk 1041. The disks may be provided with low torque motors 1042 and 1043 which may operate essentially as described with respect to the motor 209 of FIG. 3. Both filter wheels 1040 and 1041 are under constant torque from a motor and slip-clutch arrangement. Each is prevented from turning by a stop pin seated in a small hole in the wheel. Each of the twenty-one filters in a wheel has a corresponding hole. The wheel rotates whenever a solenoid pulls the pin clear of the wheel. It stops again after the pin is dropped and a new hole comes under the pin allowing it to seat. Since this arrangement essentially conforms with that shown in FIG. 3, the details are not further illustrated in FIG. 21. It will be apparent that the indexing of the filter wheels 1040 and 1041 may be controlled from an on-line computer in the same manner as generally described with respect to the preceding embodiment, so that further detail with respect to such on-line computer is unnecessary with respect to FIG. 21.

FIGS. 22 and 23 diagrammatically indicate the respective filters 1101–1121 and 1201–1221 of the filter disks 1040 and 1041. The filters 1101–1106 may conform identically to the filters 281–286 of FIG. 4, while filter position 1107 may be open and free of a filter. The filters 281–286 have been designated as a standard filter for measuring TAPPI brightness, standard filters for a four-filter colorimeter and conventionally designated X(blue), X(red), Z and $Y_C$, and a filter required by the TAPPI standard method for opacity measurements, conventionally designated as a $Y_A$ filter. Thus filters 1101 through 1106 may be designated as TAPPI brightness, X(blue), X(red), Z, $Y_C$ and $Y_A$. The filters 287 and 288 were designated Z(blue) and Z(yellow). In this case, the complete number seven filter of the embodiment of FIG. 4 can be located at a position in the reflected beam. The filters 1108 through 1121 and 1208 through 1221 may comprise interference-type narrow-band filters, which together transmit the complete visible spectrum.

By way of example each of the filter diameters may be ¾-inch. The reflectance and transmittance photocells 1032 and 1030 may be of the Schottky Silicon Photodiode type as presently used in a Model S-4 brightness and color tester. Amplifiers for each of the photodiodes can be the Analog 234 K and AD 741 C. Two digital volt meters 1225 and 1226 can be used, one for reflectance and the other for transmittance and these may be 3½ digit, 0–200 millivolt instruments with 8-4-2-1 BCD positive logic output.

As indicated at 1040a, a portion of each of the filter wheels 1040 and 1041 is preferably exposed outside of the case so that the number of the filter in the optical train can be observed directly by the operator. The filter wheel arrangement accommodates a manual placement of both wheels to any position desired. Thus manual means is provided for unlocking the solenoid operated pin for each of the wheels, whereupon the wheels may be manually manipulated at the exposed region such as 1040a and 1041a.

The ability for any operator to test a machine wide strip by moving it either left to right or right to left is desirable and is accommodated by the illustrated arrangement.

By providing at least one open position in the reflectance filter wheel, such as a position 1207, it will be apparent that the filter wheels 1040 and 1041 may provide the seven reflectance measurements and the six transmittance measurements with respect to the paper specimen 1002 in precise conformity with the corresponding measurements of the on-machine device. Reflectance and transmittance values could be obtained by the on-line computer system 1230 from simultaneous readings of the photocells 1030 and 1032, or the readings could be taken separately. Since the sensing head 1025 is conveniently removable, the instrument of FIG. 21 can also measure thickpad reflectivities $R_{oo}$. The basic design consideration is that the reflectivity value determined on a thickpad would be in agreement with the established scale and that the thickpad reflectivity calculated from a reflectance and transmittance measurement made on a single sheet would be in agreement with the directly measured value. To accomplish this objective, fourteen narrow-band filters 1108–1121 and 1208–1221 are employed to obtain data permitting calculation of the thickpad reflectivity through the weighted-ordinate integration approach. Filters of identical kind could be introduced in the incident and reflected beam. Transmittance and reflectance measurements would be performed with the open hole position such as 1207 in the reflected beam and the filter disk 1040 located through its various positions in the incident beam. The open hole 1107 in the incident beam could then be used with filter disk rotation in the reflected beam. In this way, florescence appearing in any part of the spectrum could be handled properly.

The scope of the program presently under way includes construction of the instrument as shown in FIGS. 21–23 and testing of its operation to insure that it performs in accordance with the basic objective predicting thickpad reflectivity via the fourteen narrow-band filter and weighted ordinate integration approach.

The results of a feasibility study conducted at The Institute Of Paper Chemistry in which an Automatic Color-Brightness Tester equipped with sixteen narrow-band filters was employed to obtain $R_o$ and $R_{oo}$ values and the General Electric Recording Spectrophotometer was employed to obtain transmittance data indicate the success of this approach in calculating the thickpad reflectivity compared to the directly measured values. This work was conducted by a joint applicant in the related copending joint application U.S. Ser. No. 438,993, filed Feb. 4, 1974, and is set forth in the following section.

FEASIBILITY STUDY FOR THE DESIGN AND CONSTRUCTION OF A LABORATORY INSTRUMENT BASED ON THE PRINCIPLE OF THE ON-MACHINE DEVICE

The ACBT equipped with the sixteen narrow-band filters was used to obtain $R_o$ and $R_{oo}$ values for six paper samples. Transmittance data for the same specimens were obtained using the conventional GERS. $R_{oo}$ values were calculated using the following formulas.

$$a = (1 + R_o^2 - T^2)/R_o$$

$$R_{oo} = (a/2) - \sqrt{(a/2)^2 - 1}$$

The values for T, $R_o$, $R_{oo}$ measured and $R_{oo}$ calculated, are given in Table A. The data show reasonable agreement between the measured and calculated $R_{oo}$ values. There are several factors which contribute to the differences. Fluorescence was not properly accounted for and some of the samples do fluoresce, particularly Samples 18 and 29. The samples were illuminated with a collimated beam whereas the theoretical relationship is based on diffuse illumination and diffuse viewing. The samples do change somewhat with handling as a large number of readings must be taken on each specimen. The same specimens were evaluated on filters No. 6 and 21 after all the data were collected. The data given in Table C show that some changes occurred as a result of handling during the many tests.

Tristimulus values were calculated from the $R_{oo}$ values obtained from the T and $R_o$ values using the weighting factors given by the CIE system. These tristimulus values were then compared with the directly measured tristimulus values obtained on the ACBT using the "tristimulus filters." The data, given in Table B show good agreement for most of the samples. Here again the same factors discussed earlier are responsible for the differences. In addition, the broad-band tristimulus functions of the ACBT no doubt differ slightly from the theoretical functions. It appears that sample 29 (cherry bond) shows the largest discrepancy.

It appears feasible to design and construct an instrument similar to the on-machine device of FIGS. 1–20 but also equipped with narrow-band filters which would give very nearly the correct tristimulus values in either mode. Perhaps the reasons for the discrepancies noted could be determined and further improvements made.

Table A

| Sample | T | $R_o$ | RINFM | RINFC | RINFM-RINFC |
|---|---|---|---|---|---|
| 6–3 | 0.0940 | 0.6180 | 0.6250 | 0.6270 | −0.0020 |
| 618 | 0.1070 | 0.4730 | 0.4740 | 0.4801 | −0.0061 |
| 620 | 0.1150 | 0.5590 | 0.5700 | 0.5701 | −0.0001 |
| 623 | 0.0420 | 0.4440 | 0.4450 | 0.4450 | 0.0000 |
| 629 | 0.0250 | 0.2940 | 0.2940 | 0.2942 | −0.0002 |
| 630 | 0.0110 | 0.2330 | 0.2340 | 0.2330 | 0.0010 |
| 7–3 | 0.1120 | 0.6920 | 0.7120 | 0.7095 | 0.0025 |
| 718 | 0.1270 | 0.7610 | 0.7880 | 0.7933 | −0.0053 |
| 720 | 0.1350 | 0.5930 | 0.6100 | 0.6104 | −0.0004 |
| 723 | 0.0420 | 0.4440 | 0.4460 | 0.4450 | 0.0010 |
| 729 | 0.0280 | 0.3110 | 0.3110 | 0.3113 | −0.0003 |
| 730 | 0.0090 | 0.2190 | 0.2210 | 0.2190 | 0.0020 |
| 8–3 | 0.1350 | 0.7270 | 0.7580 | 0.7578 | 0.0002 |
| 818 | 0.1460 | 0.8200 | 0.8740 | 0.8903 | −0.0163 |
| 820 | 0.1500 | 0.6160 | 0.6400 | 0.6398 | 0.0002 |
| 823 | 0.0490 | 0.4640 | 0.4660 | 0.4654 | 0.0006 |
| 829 | 0.0350 | 0.3300 | 0.3300 | 0.3305 | −0.0005 |
| 830 | 0.0120 | 0.2390 | 0.2400 | 0.2390 | 0.0010 |
| 9–3 | 0.1480 | 0.7370 | 0.7760 | 0.7768 | −0.0008 |
| 918 | 0.1550 | 0.8050 | 0.8660 | 0.8765 | −0.0105 |
| 920 | 0.1610 | 0.6240 | 0.6530 | 0.6525 | 0.0005 |
| 923 | 0.0630 | 0.4910 | 0.4940 | 0.4936 | 0.0004 |
| 929 | 0.0240 | 0.2810 | 0.2810 | 0.2812 | −0.0002 |
| 930 | 0.0170 | 0.2700 | 0.2710 | 0.2701 | 0.0009 |
| 10–3 | 0.1600 | 0.7460 | 0.7980 | 0.7962 | 0.0018 |
| 1018 | 0.1650 | 0.7980 | 0.8700 | 0.8778 | −0.0078 |
| 1020 | 0.1740 | 0.6380 | 0.6740 | 0.6738 | 0.0002 |
| 1023 | 0.1090 | 0.5820 | 0.5930 | 0.5928 | 0.0002 |
| 1029 | 0.0130 | 0.2090 | 0.2090 | 0.2090 | −0.0000 |
| 1030 | 0.0430 | 0.3650 | 0.3690 | 0.3658 | 0.0032 |
| 11–3 | 0.1660 | 0.7520 | 0.8110 | 0.8089 | 0.0021 |
| 1118 | 0.1680 | 0.7950 | 0.8740 | 0.8766 | −0.0026 |
| 1120 | 0.1750 | 0.6390 | 0.6750 | 0.6754 | −0.0004 |
| 1123 | 0.1310 | 0.6260 | 0.6440 | 0.6445 | −0.0005 |

Table A-continued

| Sample | T | $R_o$ | RINFM | RINFC | RINFM-RINFC |
|---|---|---|---|---|---|
| 1129 | 0.0090 | 0.1590 | 0.1590 | 0.1590 | −0.0000 |
| 1130 | 0.0860 | 0.4700 | 0.4760 | 0.4745 | 0.0015 |
| 12–3 | 0.1680 | 0.7480 | 0.8090 | 0.8051 | 0.0039 |
| 1218 | 0.1730 | 0.7910 | 0.8760 | 0.8766 | −0.0006 |
| 1220 | 0.1670 | 0.6210 | 0.6510 | 0.6515 | −0.0005 |
| 1223 | 0.1300 | 0.6170 | 0.6350 | 0.6346 | 0.0004 |
| 1229 | 0.0100 | 0.1400 | 0.1400 | 0.1400 | −0.0000 |
| 1230 | 0.1220 | 0.5400 | 0.5530 | 0.5517 | 0.0013 |
| 13–3 | 0.1680 | 0.7420 | 0.8000 | 0.7971 | 0.0029 |
| 1318 | 0.1740 | 0.7890 | 0.8760 | 0.8744 | 0.0016 |
| 1320 | 0.1520 | 0.5950 | 0.6170 | 0.6176 | −0.0006 |
| 1323 | 0.1170 | 0.5920 | 0.6040 | 0.6049 | −0.0009 |
| 1329 | 0.0110 | 0.1360 | 0.1360 | 0.1360 | −0.0000 |
| 1330 | 0.1520 | 0.5960 | 0.6200 | 0.6186 | 0.0014 |
| 14–3 | 0.1700 | 0.7350 | 0.7900 | 0.7893 | 0.0007 |
| 1418 | 0.1770 | 0.7880 | 0.8760 | 0.8769 | −0.0009 |
| 1420 | 0.1280 | 0.5480 | 0.5600 | 0.5613 | −0.0013 |
| 1423 | 0.0910 | 0.5400 | 0.5470 | 0.5464 | 0.0006 |
| 1429 | 0.0160 | 0.1510 | 0.1510 | 0.1510 | −0.0000 |
| 1430 | 0.1860 | 0.6450 | 0.6900 | 0.6878 | 0.0022 |
| 15–3 | 0.1680 | 0.7320 | 0.7870 | 0.7839 | 0.0031 |
| 1518 | 0.1800 | 0.7870 | 0.8780 | 0.8796 | −0.0016 |
| 1520 | 0.1000 | 0.5000 | 0.5060 | 0.5068 | <0.0008 |
| 1523 | 0.0690 | 0.4870 | 0.4900 | 0.4901 | −0.0001 |
| 1529 | 0.0470 | 0.3230 | 0.3250 | 0.3238 | 0.0012 |
| 1530 | 0.2290 | 0.7010 | 0.8000 | 0.7952 | 0.0048 |
| 16–3 | 0.1720 | 0.7330 | 0.7910 | 0.7882 | 0.0028 |
| 1618 | 0.1810 | 0.7880 | 0.8840 | 0.8832 | 0.0008 |
| 1620 | 0.0820 | 0.4560 | 0.4600 | 0.4599 | 0.0001 |
| 1623 | 0.0530 | 0.4370 | 0.4380 | 0.4385 | −0.0005 |
| 1629 | 0.1680 | 0.6070 | 0.6400 | 0.6363 | 0.0037 |
| 1630 | 0.2430 | 0.7220 | 0.8610 | 0.8532 | 0.0078 |
| 17–3 | 0.1770 | 0.7400 | 0.8080 | 0.8018 | 0.0062 |
| 1718 | 0.1840 | 0.7880 | 0.8920 | 0.8882 | 0.0038 |
| 1720 | 0.0680 | 0.4220 | 0.4240 | 0.4244 | −0.0004 |
| 1723 | 0.0410 | 0.3960 | 0.3960 | 0.3968 | −0.0008 |
| 1729 | 0.2400 | 0.7140 | 0.8240 | 0.8321 | −0.0081 |
| 1730 | 0.2470 | 0.7240 | 0.8790 | 0.8654 | 0.0136 |
| 18–3 | 0.1870 | 0.7480 | 0.8290 | 0.8228 | 0.0062 |
| 1818 | 0.1880 | 0.7900 | 0.9020 | 0.9001 | 0.0019 |
| 1820 | 0.0660 | 0.4170 | 0.4190 | 0.4192 | −0.0002 |
| 1823 | 0.0380 | 0.3880 | 0.3880 | 0.3887 | −0.0007 |
| 1829 | 0.2520 | 0.7300 | 0.8780 | 0.8928 | −0.0148 |
| 1830 | 0.2510 | 0.7240 | 0.8850 | 0.8739 | 0.0111 |
| 19–3 | 0.1950 | 0.7560 | 0.8530 | 0.8450 | 0.0080 |
| 1918 | 0.1930 | 0.7900 | 0.9140 | 0.9111 | 0.0029 |
| 1920 | 0.0710 | 0.4230 | 0.4250 | 0.4256 | −0.0006 |
| 1923 | 0.0410 | 0.3930 | 0.3940 | 0.3938 | 0.0002 |
| 1929 | 0.2580 | 0.7300 | 0.8980 | 0.9111 | −0.0131 |
| 1930 | 0.2550 | 0.7230 | 0.8900 | 0.8806 | 0.0094 |
| 20–3 | 0.2030 | 0.7640 | 0.8790 | 0.8715 | 0.0075 |
| 2018 | 0.1980 | 0.7930 | 0.9270 | 0.9345 | −0.0075 |
| 2020 | 0.0660 | 0.4110 | 0.4130 | 0.4132 | −0.0002 |
| 2023 | 0.0400 | 0.3840 | 0.3840 | 0.3847 | −0.0007 |
| 2029 | 0.2610 | 0.7280 | 0.9080 | 0.9142 | −0.0062 |
| 2030 | 0.2590 | 0.7240 | 0.8960 | 0.8940 | 0.0020 |
| 21–3 | 0.2110 | 0.7630 | 0.8960 | 0.8838 | 0.0122 |
| 2118 | 0.2020 | 0;.7890 | 0.9340 | 0.9337 | 0.0003 |
| 2120 | 0.0900 | 0.4650 | 0.4770 | 0.4699 | 0.0071 |
| 2123 | 0.0560 | 0.4410 | 0.4480 | 0.4427 | 0.0053 |
| 2129 | 0.2610 | 0.7240 | 0.9110 | 0.8999 | 0.0111 |
| 2130 | 0.2600 | 0.7180 | 0.8980 | 0.8792 | 0.0188 |

T Transmittance measured with GERS
$R_o$ Reflectance with black backing measured on the ACBT
RINFM Reflectance of opaque pad measured on the ACBT
RINFC Reflectance of opaque pad as calculated from $R_o$ and T
RINFM-RINFC Difference between the measured and calculated $R_x$ values
Sample The first number (6 through 21) designates the filter number. The last two characters designate the sample number.

Table B

| Sample | X | | Y | | Z | |
|---|---|---|---|---|---|---|
| | C | M | C | M | C | M |
| 3 | 77.7 | 77.9 | 79.6 | 79.3 | 90.4 | 90.6 |
| 18 | 86.5 | 86.3 | 88.0 | 87.6 | 102.4 | 102.5 |
| 20 | 49.3 | 50.0 | 55.1 | 55.2 | 76.4 | 76.3 |
| 23 | 45.0 | 45.3 | 52.8 | 52.9 | 59.7 | 59.9 |
| 29 | 52.2 | 50.9 | 34.2 | 31.5 | 33.0 | 31.8 |
| 30 | 71.1 | 69.9 | 68.5 | 68.2 | 34.0 | 33.9 |

C Values calculated from narrow-band filter data.
M Values determined using the "tristimulus filters".
Sample Description
3   Advantage offset wave 50 lb.
18  S-20 Nekoosa Bond
20  S-20 Nekoosa Bond Blue
23  S-20 Nekoosa Bond Green
29  S-20 Nekoosa Bond Cherry
30  S-20 Nekoosa Bond Buff Table C Change in the Measured $R_x$ Values with Handling for No. 6 and 21 Filters on the ACBT

| | \multicolumn{6}{c}{No. 6 Filter (401 nm)} |
|---|---|---|---|---|---|---|
| | 3 | 18 | 20 | 23 | 29 | 30 |
| Start of test | 0.625 | 0.474 | 0.570 | 0.445 | 0.294 | 0.234 |
| End of test | 0.623 | 0.465 | 0.570 | 0.445 | 0.293 | 0.234 |

| | \multicolumn{6}{c}{No. 21 Filter (697 nm)} |
|---|---|---|---|---|---|---|
| | 3 | 18 | 20 | 23 | 29 | 30 |
| Start of test | 0.896 | 0.934 | 0.477 | 0.448 | 0.911 | 0.898 |
| End of test | 0.889 | 0.927 | 0.474 | 0.446 | 0.895 | 0.898 |

What I claim is:

1. Apparatus for obtaining a quantitative measure of a paper optical property, said apparatus comprising:
   a. an optical measuring device having a receiving region for receiving in operative relation thereto a single thickness of paper sheet material,
   b. said optical measuring device having an optical system with at least two substantially independent photometric sensors and at least two distinct light energy paths each including at least light source and spectral response filter means and a respective one of said photometric sensors, and each intersecting said receiving region prior to the respective associated photometric sensor,
   c. each of said at least two distinct light energy paths having substantially a common spectral response characteristic sufficient to characterize said paper optical property but being respectively arranged for collecting reflected and transmitted light energy from the receiving region after impingement of the light energy on a single thickness of paper sheet material at said region so as to essentially characterize the reflectance and transmittance of the paper sheet material, whereby the paper optical property is characterized with substantially greater accuracy than any characterization of said paper optical property by either a reflectance or a transmittance measurement taken by itself, and
   d. automatic digital computer means connected on line with said optical measuring device and coupled with the respective photometric sensors of said distinct light energy paths for receiving therefrom respective output signals in accordance with the reflectance and transmittance of the paper sheet material and automatically operable on the basis of said output signals to calculate a quantitative indication of said paper optical property,
   e. said optical system having two distinct light energy paths each having a spectral response characteristic substantially corresponding to the standard brightness spectral distribution of light energy, and said quantitative indication representing the standard brightness of said paper sheet material.

2. Apparatus according to claim 1 with said optical system having two distinct light energy paths each having a spectral response characteristic with an effective wavelength of substantially 457 nanometers and with a wavelength bandwidth and shape essentially in accordance with the standard brightness spectral reponse over a range from about 400 nanometers to about 500 nanometers.

3. Apparatus for obtaining a quantitative measure of paper optical properties, said apparatus comprising:
   a. said optical measuring device having a receiving region for receiving in operative relation thereto a single thickness of paper sheet material,
   b. said optical measuring device having an optical system with at least two substantially independent photometric sensor means and including light source means and filters for controlling the spectrum of light energy transmitted to the photometric sensor means, said light source means and filters together with the respective photometric sensor means providing a plurality of respective common paper optical property measurement spectral response characteristics sufficient to characterize said paper optical properties,
   c. the respective photometric sensor means being arranged at respective opposite sides of said receiving region for collecting respectively reflected and transmitted light energy from the receiving region after impingement of the light energy on a single thickness of paper sheet material at said receiving region, and the optical system having means comprising said light source means, said filters and the respective photometric sensor means providing respective reflectance and transmittance light energy paths each exhibiting said plurality of respective common paper optical property measurement spectral response characteristics, and
   d. the respective photometric sensor means being responsive respectively to the light energy impinging thereon under the control of said filters, from the respective associated reflectance and transmittance light energy paths to provide respective pluralities of reflectance and transmittance output signals for characterizing respective ones of said paper optical properties each on the basis of both a reflectance and a transmittance measurement with respect to the single thickness paper sheet material.

4. Apparatus according to claim 3 with said optical system including said light source means, said filters and said photometric sensor means providing respectively C.I.E. tristimulus $\bar{x}$, $\bar{y}$, $\bar{z}$, and standard opacity spectral response characteristics for each respective one of said reflectance and transmittance light energy paths, said photometric sensor means providing respective pairs of reflectance and transmittance output signals for characterizing the color and opacity of the single thickness paper sheet material.

5. Apparatus according to claim 3, with said optical system including said light source means, said filters and said photometric sensor means providing respectively a standard brightness and a standard opacity spectral reponse characteristic for each respective one of said reflectance and transmittance light energy paths, said photometric sensor means providing respective pairs of reflectance and transmittance output signals for characterizing the standard brightness and opacity of the single thickness paper sheet material.

6. Apparatus according to claim 3 with said optical system including said light source means, said filters and said photometric sensor means providing respectively standard brightness, C.I.E. tristimulus $\bar{X}$, $\bar{Y}$, $\bar{Z}$, and standard opacity spectral response characteristics for each respective one of said reflectance and transmittance light energy paths, said photometric sensor means providing respective pairs of reflectance and transmittance output signals for characterizing standard brightness, the color and opacity of the single thickness paper sheet material.

7. Apparatus for obtaining a quantitative measure of paper optical properties, said apparatus comprising:
   (a) an optical measuring device having a receiving region for receiving in operative relation thereto a single thickness of paper sheet material, b. said optical measuring device having an optical measurement system with at least two substantially independent photometric sensor means and including light source means and filters for controlling the spectrum of light energy transmitted to the photometric sensor means, the optical measurement system having means comprising said light source means, said filters and the respective photometric sensor means providing respective substantially differentiated light energy paths, and providing a plurality of respective common paper optical property measurement spectral response characteristics with respect to said paths sufficient to characterize said paper optical properties, c. the respective photometric sensor means being arranged as part of the respective substantially differentiated paths for collecting light energy from the receiving region after impingement of the light energy on a single thickness of paper sheet material at said receiving region, and d. said optical measurement system having means including said photometric sensor means as energized by the light energy impinging thereon under the control of said filters, from the respective associated light energy paths, for providing respective pairs of output signals for characterizing respective ones of said paper optical properties with respect to the single thickness paper sheet material.

8. Apparatus according to claim 7, with said optical measurement system including said light source means, said filters and said photometric sensor means providing respective C.I.E. tristimulus x, y, z, and standard opacity spectral response characteristics in common for said substantially differentiated light energy paths, said photometric sensor means providing respective pairs of output signals for characterizing the color and opacity of the single thickness paper sheet material.

9. Apparatus according to claim 7, with said optical measurement system including said light source means, said filters and said photometric sensor means providing respectively a standard brightness and a standard opacity spectral response characteristic for said substantially differentiated light energy paths, said photometric sensor means providing respective pairs of output signals for characterizing respectively standard brightness and opacity of the single thickness paper sheet material.

10. Apparatus according to claim 7, with said optical measurement system including said light source means, said filters and said photometric sensor means providing respectively standard brightness, C.I.E. tristimulus $\bar{x}, \bar{y}, \bar{z}$, and standard opacity spectral response characteristics in common for said substantially differentiated light energy paths, said photometric sensor means providing respective pairs of reflectance and transmittance output signals for characterizing standard brightness, the color and opacity of the single thickness paper sheet material.

11. Apparatus for obtaining a quantitative measure of an optical property of substantially homogeneous sheet material, which comprises an optical measuring device having a sheet receiving region for receiving in operative relation thereto a single thickness of substantially homogenous sheet material, said optical measuring device having an optical measuring system with photometric sensor means capable of providing two independent output signals and including automatic digital computer means connected on line with said photometric sensor means, two physically separate light energy paths each including substantially a common area of said sheet receiving region and means comprising each of said two physically separate light energy paths providing substantially a common spectral response characteristic sufficient to characterize said optical property and providing respective independent output signals such as to essentially characterize two essentially independent optical response parameters of the substantially homogeneous sheet material and such as to characterize the optical property with substantially greater accuracy than any characterization of said optical property by either one of such optical response parameters taken by itself, said optical measuring system having a common incident light energy path impinging on said receiving region and having a spectral response characteristic substantially corresponding to the standard brightness spectral distribution of light energy, and said computer means supplying a quantitative indicatiion representing the standard brightness of said sheet material.

12. Apparatus according to claim 11 with said optical measuring system having a common incident light energy path and having a spectral response characteristic common to both said physically separate light energy paths with an effective wavelength of substantially 457 nanometers and with a wavelength bandwidth and shape essentially in accordance with the standard brightness spectral response over a range from about 400 nanometers to about 500 nanometers.

13. The method of sensing a plurality of optical properties which comprises:

a. impinging a broad spectrum of visible light on a substantial area of one surface of a single thickness of substantially homogeneous sheet material by means of an optical measuring system, b. optically viewing the illuminated area of said substantially homogeneous sheet material by means of respective physically separate light energy paths of matched spectral response characteristics, c. independently photometrically sensing the light energy of the respective physically separate light energy paths and generating respective independent output signals, and d. controlling the spectral response characteristics of the optical measuring system to provide matched pairs of spectral response characteristics simulating respective optical property measurement spectral response functions and generating by means of said optical measuring system respective pairs of essentially distinct optical response parameters for characterizing the respective optical properties of said single thickness of substantially homogeneous sheet material more accurately than any characterization by either optical response parameter of the pairs taken alone, and without any need for physically changing of a backing for said sheet material.

14. The method of monitoring brightness of a moving paper web during manufacture thereof, which comprises:

a. impinging on the moving paper web light energy from a source providing a band of visible light, b. respectively collecting from the moving paper web reflected light energy transmitted through the moving paper web along a reflectance light energy path and transmitted light energy transmitted through the moving paper web along a transmittance light energy path, and c. photometrically sensing the reflected light energy and the transmitted light energy under substantially matched spectral response conditions of the reflectance and transmittance light energy paths, each of the spectral response conditions substantially corresponding to a predetermined paper brightness measurement spectral function, and producing by means of the photometrically sensing step respective separate reflectance and transmittance output signals essentially characterizing the brightness of the moving paper web with greater accuracy than any characterization of such brightness by either of the output signals taken by itself.

15. The method of claim 14 with the light from the light source being filtered to produce substantially matched spectral response conditions of the reflectance and transmittance light energy paths and each substantially corresponding to a standard brightness measurement spectral function such that the respective separate reflectance and transmittance output signals essentially characterize the brightness of the moving paper web.

16. The method of claim 14 with the light energy from the source following reflectance and transmittance light energy paths having substantially a common spectral response characteristic with an effective wavelength of substantially 457 nanometers and with a wavelength bandwidth and shape essentially in accordance with the standard brightness spectral function for characterizing TAPPI brightness.

17. Apparatus for measuring optical properties comprising an optical measuring system including photometric sensor means, including light energy path means for supplying respective spectrums of light energy to said photometric sensor means after transmission through a single thickness sheet material for providing respective signal components from the photometric sensor means as measures of transmittance of the sheet material for the respective spectrums of light energy, including a reflectance sensing arrangement operative to provide respective signal components from the photometric sensor means as measures of the reflectance of the sheet material for the respective spectrums of light energy; the light energy path means being operative in conjunction with said photometric sensor means and said reflectance sensing arrangement for characterizing respective optical properties comprising brightness and opacity and each being based on both a transmittance measure and a reflectance measure.

18. In the art of paper manufacture, apparatus for obtaining a quantitative measure of a paper optical property, which comprises: an on-machine optical monitoring device for mounting on a paper machine and having a web receiving region for receiving in operative relation thereto a moving web of paper sheet material being produced by such machine, said on-machine optical monitoring device having an optical system with at least two substantially independent photometric sensors and at least two distinct light energy paths each including at least light source and spectral filter means and a respective one of said photometric sensor, and each intersecting said web receiving region prior to the respective associated photometric sensor, said at least to distinct light energy paths comprising a reflectance light energy path and a transmittance light energy path each having a substantial bandwidth compatible with a paper optical property measurement spectral function for characterizing said paper optical property, said photometric sensors being arranged relative to the web receiving region for collecting respectively reflected and transmitted light energy from a web of paper sheet material at said web receiving region and providing respective reflectance and transmittance output signals essentially characterizing two essentially independent optical response parameters of the paper sheet material with respect to said predetermined paper optical property measurement spectral function, and storage means connected on line with said on-machine optical monitoring device for automatically separately storing respective discrete quantities in accordance with the reflectance and transmittance output signals respectively from said photometric sensor for characterizing at least one of paper brightness and paper color with substantially greater accuracy than any characterization thereof by either one of the respective stored discrete quantities taken by itself.

19. Apparatus according to claim 18 with said reflectance and transmittance light energy paths having a common spectral response characteristic substantially corresponding to a standard brightness measurement spectral function, and said stored discrete quantities characterizing the standard brightness of said paper sheet material with substantially greater accuracy than any characterization thereof by either one of the respective stored discrete quantities taken by itself.

20. Apparatus according to claim 18 with said reflectance and transmittance light energy paths having a common spectral response characteristic with an effective wavelength of substantially 457 nanometes and with a wavelength bandwidth and shape essentially in accordance with the standard brightness spectral distribution for characterizing TAPPI brightness.

21. Apparatus according to claim 18 with said optical system providing at least three spectral response characteristics common to both reflectance and transmittance light energy paths and providing therefrom three sets of reflectance and transmittance output signals for characterizing the color of the web of paper sheet material with substantially greater accuracy than any characterization of said color of said paper sheet material by either one of the reflectance and transmittance output signals of the three sets taken alone.

22. Apparatus according to claim 18 with said optical system providing reflectance and transmittance light energy paths having respectively in common spectral response characteristics for essentially simulating the C.I.E. tristimulus $\bar{x}$, $\bar{y}$ and $\bar{z}$ spectral functions and providing therefrom three sets of reflectance and transmittance output signals for characterizing the color of the web of paper sheet material with substantially greater accuracy than any characterization of said color of said paper sheet material by either one of the reflectance and transmittance output signals of the respective three sets taken aone.

23. The method of monitoring a paper optical property of a moving paper web during manufacture thereof, which comprises:

a. impinging on the moving paper web light energy from a source providing a broad band of visible light, b. respectively collecting from the moving paper web reflected light energy reflected from the moving paper web along a reflectance light energy path and transmitted light energy transmitted through the moving paper web along a transmittance light energy path, and c. filtering the light energy from the souce and photometrically sensing the reflected light energy and the transmitted light energy under substantially matched spectral response conditions of the reflectance and transmittance light energy paths, each of the spectral response conditions substantially corresponding to a predetermined paper optical property measurement spectral function, and producing by means of the photometrically sensing step respective separate reflectance and transmittance output signals essentially characterizing the paper optical property with greater accuracy than any characterization of said paper optical property by either of the output signals taken by itself, d. the light from the light source being filtered to produce substantially matched spectral response conditions of the reflectance and transmittance light energy paths and each substantially corresponding to a standard brightness measurement spectral function such that the respective separate reflectance and transmittance output signals essentially characterize the brightness of the moving paper web.

24. The method of claim 23 with the filtering of the light energy from the source providing reflectance and transmittance light energy paths having substantially a common spectral response characteristic with an effective wavelength of substantially 457 nanometers and with a wavelength bandwidth and shape essentially in accordance with the standard brightness spectral function for characterizing TAPPI brightness.

25. The method of monitoring a paper optical property of a moving paper web during manufacture thereof, which comprises:

a. impinging on the moving paper web light energy from a source providing a broad band of visible light, b. respectively collecting from the moving paper web reflected light energy reflected from the moving paper web along a reflectance light energy path and transmitted light energy transmitted through the moving paper web along a transmittance light energy path, and c. filtering the light energy from the source and photometrically sensing the reflected light energy and the transmitted light energy under substantially matched spectral response conditions of the reflectance and transmittance light energy paths, each of the spectral response conditions substantially corresponding to a predetermined paper optical property measurement spectral function, and producing by means of the photometrically sensing step respective separate reflectance and transmittance, output signals essentially characterizing the paper optical with greater accuracy than any characterization of said paper optical property by either of the output signals taken by itself, d. the filtering of the light energy from the source providing reflectance and transmittance light energy paths each with three respective spectral response characteristics and such that three sets of separate reflectance and transmittance output signals are produced essentially characterizing the color of the moving paper web with substantially greater accuracy than any characterization of said color of said moving paper web by either one of the reflectance and transmittance output signals of the respective three sets taken alone.

26. The method of claim 25 with the filtering of the light energy from the source providing at least three spectral response characteristics for each of the reflectance and transmittance light energy paths substantially corresponding respectively to the C.I.E. tristimulus $\bar{x}$, $\bar{y}$ and $\bar{z}$ spectral response functions and providing three sets of reflectance and transmittance output signals for essentially characterizing the color of the moving paper web with greater accuracy than any characterization of the color of the moving paper web by either one of the reflectance and transmittance output signals of the respective three sets taken alone.

27. Apparatus for obtaining a quantitative measure of the visual brightness of substantially homogeneous sheet material, which comprises an optical measuring device having a sheet receiving region for receiving in operative relation thereto a single thickness of substantially homogeneous sheet material, said optical measuring device having an optical measuring system with photometric sensor means capable of providing two essentially independent output signals and including automatic digital computer means connected on line with said photometric sensor means, two physically separate light energy paths each including said sheet receiving region and said photometric sensor means and means comprising each of said two physically separate light energy paths providing substantially a common brightness spectral response characteristic sufficient to characterize the visual brightness of said sheet material and providing respective essentially independent output signals such as to essentially characterize two essentially independent optical response parameters of the substantially homogenous sheet material and such as to characterize the visual brightness of the sheet material with substantially greater accuracy than any characterization thereof by either one of such optical response parameters taken by itself.

28. Apparatus according to claim 27 with said automatic digital computer means being connected on line with said photometric sensor means for receiving therefrom respective essentially independent output signals in accordance with the reflectance and transmittance of the sheet material and means controlling said digital computer means to calculate a quantitative indication of said visual brightness on the basis of said output signals.

29. Apparatus according to claim 27 with said optical measuring system having a common incident light energy path and a common area of said sheet receiving region both essentially common to said two physicaly separate light energy paths such that said output signals characterize an essentially common portion of said sheet material.

30. Apparatus for obtaining a quantitative measure of a plurality of optical properties of substantially homogeneous sheet material, which comprises an optical measuring device having a sheet receiving region for receiving in operative relation thereto a single thickness of substantially homogenous sheet material, said optical measuring device having an optical measuring system with photometric sensor means capable of providing two essentially independent output signals and including automatic digital computer means connected on line with said photometric sensor means, two physically separate light energy paths each including said sheet receiving region and said photometric sensor means and means comprising each of said two physically separate light energy paths providing respective substantially common spectral response characteristics sufficient to characterize the respective optical properties and providing respective sets of essentially independent output signals such as to essentially characterize respective sets of two essentially independent optical response parameters of the substantially homogeneous sheet material and such as to characterize each of the respctive optical properties with substantially greater accuracy than any characterization of such optical property by either one of such optical response parameters taken by itself.

31. Apparatus according to claim 30 with said automatic digital computer means being connected on line with said photometric sensor means for receiving therefrom sets of respective essentially independent output signals in accordance with the reflectance and transmittance of the sheet material and means controlling said digital computer means to calculate a quantitative indication of said optical properties on the basis of said output signals.

32. Apparatus according to claim 30 with said optical measuring system having a common incident light energy path impinging at a common area of said sheet receiving region common to said two physically separate light energy paths.

33. The method of monitoring paper optical properties during manufacture of a paper web, which comprises: impinging light on the moving web of paper at sample areas thereof such that respective different wavelengths distributions of light can be collected from the sample areas, such wavelength distributions taken together being at least sufficient to characterize the brightness and color of a section of the paper of the moving web instantaneously at a monitoring location, collecting light of the respective wavelength distributions after impingement on the sample areas and separately photometrically sensing the collected light of the respective wavelenth distributions to generate respective output signals, and separately photometrically sensing collected light as to at least certain of said sample areas under respective sufficiently differtiated conditions so as to obtain at least two substantially independent output signals representing substantially independent optical parameters for each of such certain sample areas, and sampling all of the output signals including the substantially independent output signals for the certain sample areas so as to obtain quantitative values reliably characterizing the average brightness and color of the section of the web at the monitoring location with sufficient accuracy so as to enable control of the brightness and color characteristics of the web during the manufacture thereof.

34. In the art of paper manufacture, apparatus for obtaining a quantitative measure of paper optical properties, which comprises an on-machine optical monitoring device for mounting on a paper machine in operative association with a moving web of paper sheet material being produced by such machine, and comprising a light souce and filter assembly for supplying respective different spectral distributions of light energy to a web of paper sheet material sufficient to characterize a plurality of paper optical properties including at least brightness and color, and a light receptor assembly disposed for collecting light energy of the respective different spectral distributions after impingement on a web of paper sheet material and for separately photometrically sensing said light energy to generate respective output signals sufficient to characterize said plurality of paper optical properties including at least brightness and color, means comprising said light receptor assembly of said on-machine optical monitoring device defining at least two distinct light energy collecting paths and including respective substantially independent photometric sensors operaively associated with the respective paths, for collecting and responding to a common one of the respective different spectral distributions of light energy after impingement on a web of paper sheet material, under respective sufficiently differentiated conditions so as to provide at last two substantially independent output signals which together are sufficient to essentially characterize an infinite reflectance value $R_{\infty}$ of the paper sheet material, and means on-line with said on-machine optical monitoring device and connected with said substantially independent photometric sensors for receiving said respective output signals including the two substantially independent output signals responsive to the common spectral distributions of light energy, and for responding to said output signals including said two substantially independent output signals to supply respective quantitative indications of said plurality of paper optical properties including at least brightness and color, and to supply at least one of said quantitative indications on the basis of the two substantially independent output signals which together essentially characterize the infinite reflectance value of said paper sheet material for the common spectral distribution of light energy.

35. Optical property measuring apparatus which comprises: a color sensing device having a material receiving region for receiving a single thickness of sheet material whose color is to be sensed, and comprising an optical assembly and a backing assembly for mounting at respective opposite sides of the material receiving region, said optical assembly having light source means, spectral response filter means and photometric sensor means providing a plurality of reflectance sensing light paths having respective spectral response characteristics such as together to define substantially a standard tristimulus spectral distribution, said reflectance sensing light paths extending from the light source means toward the backing assembly so as to impinge on the material receiving region for reflection from a sheet material in said region and backed by said backing assembly, and extending from the material receiving region to the photometric sensing means so as to provide respective reflectance output signals representing the respective reflectance values of the sheet material in said region in reference to the respective spectral response characteristics of the respective reflectance sensing light paths, wherein the improvement comprises said backing assembly together with said optical assembly further providing respective transmittance sensing light paths including photometric sensor means and having respective spectral response characteristics such as together to define substantially a standard tristimulus spectral distribution, and said transmittance sensing light paths extending from the light source means toward and through sais material receiving region, and said backing assembly having light transmitting aperture means communicating with the material receiving region, the transmittance sensing light paths extending through said aperture means so that light energy is transmitted through sheet material at the material receiving region and through the aperture means of the backing assembly for photometric evaluation by the photometric sensing means, and the transmittance sensing light paths thereby providing respective transmittance output signals representing the respective transmittance output signals representing the respective transmittance values of sheet material in said region in reference to the respective spectral response characteristics of the respective transmittance sensing light paths, and said color sensing device thereby characterizing the color of sheet material in said region by means of both said reflectance and said transmittance values and with an essential independence of basis weight.

36. Apparatus for obtaining a quantitative measure of an optical property of a moving web of substantially homogeneous sheet material, which comprises:
 a. an optical monitoring device having a web receiving region for receiving in operative relation thereto a web of sheet material moving along a web path,
 b. said optical monitoring device having an optical system with photometric sensor means capable of providing two essentially independent output signals and with two distinct light energy paths each including light source means, spectral response filter means and said photometric sensor means, said photometric sensor means being responsive to light energy received from the web receiving region after impingement on sheet material in said region,
 c. each of said two distinct light energy paths having substantially a common spectral response characteristic sufficient to characterize said optical property but being respectively arranged for collecting said light energy from the web receiving region after impingement on said web under respective substantially differentiated conditions so as to provide respective essentially independent output signals from said photometric sensor means such as to essentially characterize two essentially independent optical response parameters of the sheet material and such as to characterize the optical property with substantially greater accuracy than any characterization of said optical property by either one of such optical response parameters taken by itself,
 d. automatic digital computer means connected on line with said optical monitoring device and coupled with said photometric sensor means for receiving therefrom said respective essentially independent optical response parameters and automatically operable on the basis of said output signals to calculate a quantitative indication of said optical property,
 e. said monitoring device including an optical window member disposed on the opposite side of the web receiving region from said light source means,
 f. one of the light energy paths being a reflectance sensing light path for sensing of reflectance of the sheet material as backed by said optical window member and the other of said light energy paths being a transmittance sensing light path for sensing the transmittance of the sheet material and said optical window member in series.

37. Apparatus according to claim 36 with means mounting said monitoring device for movement transversely of the web path to sample the reflectance and transmittance of the web of sheet material at different portions of the width thereof, and mounting said monitoring device for movement to an off-web position to one side of the web path.

38. The method of monitoring paper optical properties during manufacture of a paper web, which comprises:
 a. impinging on the moving paper web light energy frm a source providing a broad band of visible light,
 b. collecting light energy from the source after impingement on the moving paper web under two substantially differentiated sets of optical path conditions such as to essentially characterize two essentially independent optical response parameters of said paper web, and filtering and photometrically sensing the light energy so collected under three respective spectral response conditions each common to both of said optical path conditions such that the color of the paper web can be characterized by three sets of said two substantially independent optical response parameters, and
 c. separately storing quantitative results of the filtering and photometrically sensing of said light energy under said three respective spectral response conditions for said two sets of optical path conditions so as to obtain six substantially independent optical response parameters from which color of the paper web can be calculated with substantially greater accuracy than is possible from the three optical response parameters for either of said sets of optical path conditions taken alone.

39. The method of claim 38 where the filtering and photometrically sensing is with respect to transmittance and reflectance optical paths and the light is collected under respective $E_c\bar{x}$, $E_c\bar{y}$ and $E_c\bar{z}$ spectral response conditions each being common to respective transmittance and reflectance optical paths.

40. In the art of paper manufacture, apparatus for obtaining a quantitative measure of a paper optical property, which comprises:
 a. an on-machine optical monitoring device for mounting on a paper machine and having a web receiving region for receiving in operative relation thereto a moving web of paper sheet material being produced by such machine,
 b. said on-machine optical monitoring device having an optical system with at least two substantially independent photometric sensors and at least two distinct light energy paths each including at least light source and spectral response filter means and a respective one of said photometric sensor, and each intersecting said web receiving region prior to the respective associated photometric sensor,
 c. said at least two distinct light energy paths comprising a reflectance light energy path and a transmittance light energy path having a common spectral response characteristic of substantial bandwidth and of response over such bandwidth for essentially simulating a predetermined paper optical property measurement spectral function such as to characterize said paper optical property, said photometric sensors being arranged on opposite sides of the web receiving region for collecting respectively reflected and transmitted light energy from a web of paper sheet material at said web receiving region and providing respective reflectance and transmittance output signals essentially characterizing two essentially independent optical response parameters of the paper sheet material with respect to said predetermined paper optical property measurement spectral function, and such as to characterize said paper optical property with substantially greater accuracy than any characterization of said paper optical property by either one of such optical response parameters taken by itself, and d. automatically operating digital computer means connected on line with said on-machine optical monitoring device and coupled with the respective photometric sensors and including storage means for automatically separately storing respective reflectance and transmittance signals in accordance with the reflectance and transmittance output signals respectively from said photometric sensors, and means for automatically retrieving said reflectance and transmittance signals from said storage means and for automatically calculating said paper optical property on the basis of a non-linear relationship between such paper optical property and the reflctance and transmittance values of said paper sheet material, thereby to provide a quantitative measure from which at least one of paper brightness and paper color may be controlled during paper manufacture.

41. Apparatus according to claim 40 with said two distinct light energy paths each having a spectral response characteristic substantially corresponding to a standard brightness measurement spectral distribution of light energy, and said digital computer means including means for automatically computing a quantitative indication of the brightness of said paper sheet material.

42. Apparatus according to claim 41 with said two distinct light energy paths each having a spectral response characteristic with an effective wavelength of substantially 457 nanometers and with a wavelength bandwidth and shape essentially in accordance with the standard brightness spectral distribution for characterizing TAPPI brightness.

43. Apparatus according to claim 40 with said two light energy paths each having a spectral response characteristic essentially simulating a C.I.E. tristimulus spectral response function.

44. Apparatus according to claim 40 with said optical system providing at least three spectral response characteristics for each of said two distinct light energy paths and said paths together providing three sets of reflectance and transmittance output signals for a given portion of said web such as to characterize the color of the portion of said web of paper sheet material with substantially greater accuracy than any characterization of said color of said paper sheet material by either one of the reflectance and transmittance output signals of the three sets taken alone.

45. Apparatus according to claim 44 with said reflectance and transmittance light energy paths having respectively in common spectral response characteristics for essentially simulating the C.I.E. tristimulus X, Y and Z spectral functions.

* * * * *